US009688997B2

(12) United States Patent
Yang et al.

(10) Patent No.: US 9,688,997 B2
(45) Date of Patent: Jun. 27, 2017

(54) **GENETICALLY MODIFIED PLANTS WITH RESISTANCE TO *XANTHOMONAS* AND OTHER BACTERIAL PLANT PATHOGENS**

(71) Applicant: IOWA STATE UNIVERSITY RESEARCH FOUNDATION, INC., Ames, IA (US)

(72) Inventors: Bing Yang, Ames, IA (US); Ting Li, Ames, IA (US); Bo Liu, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 74 days.

(21) Appl. No.: 14/362,529

(22) PCT Filed: Dec. 27, 2012

(86) PCT No.: PCT/US2012/071722
§ 371 (c)(1),
(2) Date: Jun. 3, 2014

(87) PCT Pub. No.: WO2013/101877
PCT Pub. Date: Jul. 4, 2013

(65) Prior Publication Data

US 2015/0247162 A1 Sep. 3, 2015

Related U.S. Application Data

(60) Provisional application No. 61/581,356, filed on Dec. 29, 2011.

(51) Int. Cl.

| | |
|---|---|
| ***C12N 15/82*** | (2006.01) |
| ***C07K 14/415*** | (2006.01) |
| ***C12N 9/16*** | (2006.01) |

(52) U.S. Cl.
CPC ........ *C12N 15/8281* (2013.01); *C07K 14/415* (2013.01); *C12N 9/16* (2013.01)

(58) Field of Classification Search
None
See application file for complete search history.

(56) References Cited

U.S. PATENT DOCUMENTS

| | | | | |
|---|---|---|---|---|
| 9,133,467 | B2 * | 9/2015 | Lahaye .............. | C12N 15/1072 |
| 2005/0064474 | A1 | 3/2005 | Urnov et al. | |
| 2009/0068164 | A1 | 3/2009 | Segal et al. | |
| 2009/0305402 | A1 | 12/2009 | Liljedahl et al. | |
| 2010/0111907 | A1 | 5/2010 | Ando et al. | |
| 2010/0162438 | A1 | 6/2010 | Yin et al. | |
| 2011/0145940 | A1 | 6/2011 | Voytas et al. | |
| 2011/0201118 | A1 | 8/2011 | Yang et al. | |
| 2012/0178131 | A1 | 7/2012 | Voytas et al. | |
| 2012/0178169 | A1 | 7/2012 | Voytas et al. | |
| 2012/0214228 | A1 | 8/2012 | Voytas et al. | |
| 2013/0117869 | A1 | 5/2013 | Duchateau et al. | |

FOREIGN PATENT DOCUMENTS

| | | |
|---|---|---|
| DE | 1020090046593 | 1/2009 |
| EP | 2206723 | 7/2010 |
| WO | 2007014275 | 2/2007 |
| WO | 2010079430 | 7/2010 |
| WO | 2011002503 | 1/2011 |
| WO | 2012138927 | 10/2012 |

OTHER PUBLICATIONS

Antony, Ginny, et al., "Rice xa13 Recessive Resistance to Bacterial Blight is Defeated by Induction of the Disease Susceptibility Gene Os-11N3", The Plant Cell, vol. 22, Nov. 2010, pp. 3864-3876.
Beurdeley, Marine, et al., "Compact designer TALENs for efficient genome engineering", Nature Communications, Apr. 2013, pp. 1-8.
Boch, Jens et al., "Breaking the Code of DNA Binding Specificity of TAL-Type III Effectors" Science, vol. 326, Dec. 11, 2009, pp. 1509-1512.
Boch, Jens et al., "Xanthomonas AvrBs3 Family-Type III Effectors: Discovery and Function" 2010, 48:419-436.
Bogdanove et al., "TAL effectors: Finding Plant Genes for Disease and Defense", Curr. Opin. Plant Biol., Epub Jun. 1, 2010, vol. 13, No. 4, pp. 394-401.
Christian, Michelle et al., "Targeting DNA double-strand breaks with TAL effector nucleases", Genetics. Epub Jul. 26, 2010, vol. 86, No. 2, pp. 757-761.
Christian, Michelle L. et al. "Targeting G with TAL Effectors: A comparison of Activities of TALENs Constructed with NN and NK Repeat Variable Di-Residues", Sep. 24, 2012, http://www.ncbi.nlm.nih.gov/pmc/articles/PMC3454392, [retrieved from the Internet on Jul. 1, 2013], 11 pages.
Chu, Zhaohui, et al., "Promoter mutations of an essential gene for pollen development result in disease resistance in rice", Genes & Development vol. 20, 2006, pp. 1250-1255.
Deng, Dong, et al., "Structural Basis for Sequence-Specific Recognition of DNA by TAL Effectors", Sciencexpress, Jan. 2012, pp. 1-9.
Gaj, Thomas, et al., "Targeted gene knockout by direct delivery of zinc-finger nuclease proteins", Nature Methods, vol. 9, No. 8, Aug. 2012, pp. 805-809.
GenBank Accession No. AAT46122, Nov. 12, 2004, 2 pages.
GenBank Acccession No. AY262149, May 17, 2004, 2 pages.

(Continued)

*Primary Examiner* — Medina A Ibrahim
(74) *Attorney, Agent, or Firm* — McKee, Voorhees & Sease, PLC

(57) ABSTRACT

Applicants have successfully generated heritable phenotypes in plants making them resistant to bacterial blight. TAL effector binding elements, (EBEs) of bacterial pathogen disease susceptibility genes are modified to prevent induction of expression associated with disease states caused by the bacterial pathogens. Surprisingly, Applicants have found that modifications may be made in the EBEs of these genes which prevent bacterial pathogen induction, but still allow for normal plant development and seed production. Nucleic acid sequences for generating such plants, amino acid sequences, cells, vectors and expression constructs are included as well as resistant plants, seeds and lines.

27 Claims, 19 Drawing Sheets

(56) References Cited

OTHER PUBLICATIONS

GenBank Accession No. AF158101, Apr. 10, 2006, 102 pages.
Hummel, Poster—"A cipher-like mechanism governs TAL effector-DNA recognition", Jun. 14, 2010. Jun. 14, 2010.
Kleinstiver, Benjamin P., et al., "A unified genetic, computational and experimental framework identifies functionally relevant residues of the homing endonuclease I-Bmol", Nucleic Acids Research, vol. 38, No. 7, pp. 2411-2427.
Li, Ting, et al., "TAL Nucleases (TALN): hybrid proteins composed of TAL effectors and Fokl DNA-cleavage domain", Nucleic Acids Res., Aug. 10, 2010, 39(1) pp. 359-372.
Li, "High-efficiency TALEN-based gene editing produces disease-resistant rice", Nature Biotechnoogy, vol. 30, No. 5, May 2012, pp. 390-392.
Mahfouz, Magdy M., et al., "De novo-engineered transcription activator-like effector (TALE) hybrid nuclease with novel DNA binding specificity creates double-strand breaks", PNAS, vol. 108, No. 6, Feb. 2011, pp. 2623-2628.
Mak, Amanda Nga-Sze, et al., "The Crystal Structure of TAL Effector PthXo1 Bound to Its DNA Target", Sciencexpress, Jan. 2012, pp. 1-14.
Martin-Ortigosa, Susana, et al., "Gold Functionalized Mesoporous Silica Nanoparticle Mediated Protein and DNA Codelivery to Plant Cells Via the Biolistic Method", Advanced Functional Materials, 2012, vol. 22, pp. 3576-3582.
Moscou, "A simple cipher governs DNA recognition by TAL effectors", Scienceexpress.org. Oct. 29, 2009.
Mueller, John E., et al., "Intron-encoded endonuclease I-Tevl binds as a monomer to effect sequential cleavage via conformational changes in the td homing site", The EMBO Journal, vol. 14, No. 22, 1995, pp. 5724-5735.
Romer, Patrick et al., "Promoter elements of rice susceptibility genes are bound and activated by specific TAL effectors from the bacterial blight pathogen, Xanthomonas oryzae pv. oryzae", New Phytol.vol. 187, Mar. 19, 2010, No. 4, pp. 1048-1057.
Sakai, Hiroaki, et al., "Distinct evolutionary patterns of Oryza glaberrima deciphered by genome sequencing and comparative analysis", The Plant Journal (2011), vol. 66, pp. 796-805.
Townsend, Jeffrey A. et al., "High-frequency modification of plant genes using engineered zinc-finger nucleases" Science 2008 pp. 442-445.
Voytas, Daniel F. et al., "DNA Binding Made Easy" Science vol. 326, Dec. 11, 2009, pp. 1491-1492.
Yang, Bing et al., "The virulence factor AvrXa7 of Xanthomonas oryzae pv. oryzae is a type III secretion pathway-dependent nuclear-localized double-stranded DNA-binding protein", PNAS Aug. 15, 2000, vol. 97, No. 17, pp. 9807-9812.
Zhang, Feng, et al., "Efficient construction of sequence-specific TAL effectors for modulating mammalian transcription", Nature Biotechnology, Jan. 2011, pp. 1-6.

* cited by examiner

FIG. 3

| ATAAACCCCTCCAACCAGGTGCTAAgctcatcaagccttcaagcAAAGCAAACTCAAGTAGTAGCTG | WT |
| ATAAACCCCTCCAACCAGGTGCTAAg---------------------------------------- | -49 bp |
| ATAAACCCCTCCAACCAGGTGCTAAgctcatcaagc------AAAGCAAACTCAAGTAGTAGCTG | -8 |
| ATAAACCCCTCCAACCAGGTGCTAAgctcatc-----tcaagcAAAGCAAACTCAAGTAGTAGCTG | -6 |
| ATAAACCCCTCCAACCAGGTGCTAAgctca-----ccttcaagcAAAGCAAACTCAAGTAGTAGCTG | -5 |
| ATAAACCCCTCCAACCAGGTGCTAAgctcatcaagcctt----cAAAGCAAACTCAAGTAGTAGCTG | -4 |
| ATAAACCCCTCCAACCAGGTGCTAAgctcatcaagcAActtcaagcAAAGCAAACTCAAGTAGTAGCTG | +2 |

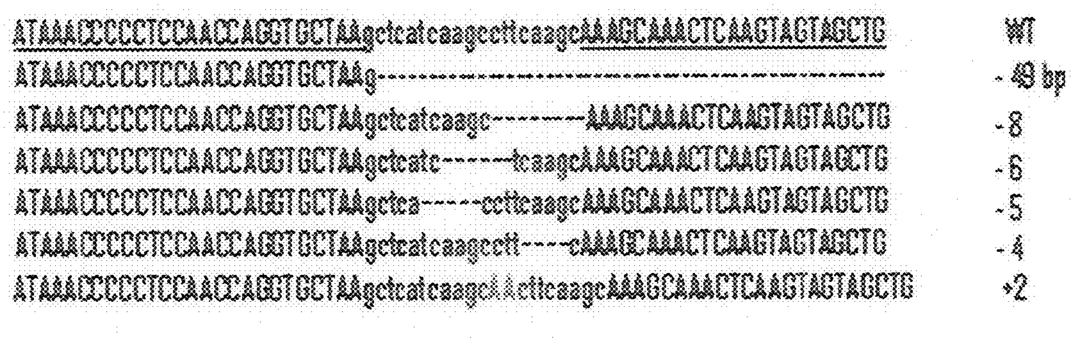

FIG. 4

TALN-L

| | | | | | | | | | | | | | | | | |
|---|---|---|---|---|---|---|---|---|---|---|---|---|---|---|---|---|
| NG | NI | NN | NI | NG | NI | NG | NN | HD | NI | NG | HD | NG | HD | HD | HD | N* |
| T | A | G | A | T | A | T | G | C | A | T | C | T | C | C | C | C |

TALN-R

| | | | | | | | | | | | | | | | | | | | | | |
|---|---|---|---|---|---|---|---|---|---|---|---|---|---|---|---|---|---|---|---|---|---|
| NI | NG | NI | NG | NI | NN | NG | NG | NN | NN | NI | NN | NI | HD | HD | HD | NG | HD | HD | NI | HD | N* |
| A | T | A | T | A | G | T | T | G | G | A | G | A | C | C | C | T | C | C | A | C | T |
| 1 | 2 | 3 | 4 | 5 | 6 | 7 | 8 | 9 | 10 | 11 | 12 | 13 | 14 | 15 | 16 | 17 | 18 | 19 | 20 | 21 | 22 |

1. dTALEN-L1 (SEQ ID NO: 23)

ATGGATCCCATTCGTTCGCGCACGCCAAGTCCTGCCCGCGAGCTTCTGCCCGGACCCCAACCGGAT
AGGGTTCAGCCGACTGCAGATCGGGGGGGGGCTCCGCCTGCTGGCGGCCCCCTGGATGGCTTGCCC
GCTCGGCGGACGATGTCCCGGACCCGGCTGCCATCTCCCCCTGCGCCCTCGCCTGCGTTCTCGGCG
GGCAGCTTCAGCGATCTGCTCCGTCAGTTCGATCCGTCGCTTCTTGATACATCGCTTCTTGATTCG
ATGCCTGCCGTCGGCACGCCGCATACAGCGGCTGCCCCAGCAGAGTGGGATGAGGTGCAATCGGGT
CTGCGTGCAGCCGATGACCCGCCACCCACCGTGCGTGTCGCTGTCACTGCCGCGCGGCCGCCGCGC
GCCAAGCCGGCCCCGCGACGGCGTGCGGCGCAACCCTCCGACGCTTCGCCGGCCGCGCAGGTGGAT
CTACGCACGCTCGGCTACAGTCAGCAGCAGCAAGAGAAGATCAAACCGAAGGTGCGTTCGACAGTG
GCGCAGCACCACGAGGCACTGGTGGGCCATGGGTTTACACACGCGCACATCGTTGCGCTCAGCCAA
CACCCGGCAGCGTTAGGGACCGTCGCTGTCAAGTATCAGCACATAATCACGGCGTTGCCAGAGGCG
ACACACGAAGACATCGTTGGCGTCGGCAAACAGTGGTCCGGCGCACGCGCCCTGGAGGCCTTGCTC
ACGAAGGCGGGGGAGTTGAGAGGTCCGCCGTTACAGTTGGACACAGGCCAACTTCTCAAGATTGCA
AAACGTGGCGGCGTGACCGCAGTGGAGGCAGTGCATGCATCGCGCAATGCACTGACGGGTGCCCCC
CTGAACCTGACCCCGGCACAGGTGGTGGCCATCGCCAGCCACGATGGCGGCAAGCAGGCGCTGGAG
ACGGTGCAGCGGCTGTTGCCGGTGCTGTGCCAGGACCATGGCCTGACCCCGGACCAGGTCGTGGCC
ATCGCCAGCAATGGCGGCGGCAAGCAGGCCTTGGAGACGGTGCAGCGGCTGTTGCCGGTGCTGTGC
CAGGCCCATGGCCTGACCCCGGCCCAAGTGGTGGCCATCGCCAGCAATGGCGGCGGCAAGCAGGCT
CTGGAGACGGTACAGCGGCTGTTGCCGGTGCTGTGCCAGGACCATGGCCTGACCCAGGACCAGGTG
GTGGCCATCGCCAGCCACGATGGCGGCAAGCAGGCGTTGGAGACGGTACAGCGGCTGTTGCCGGTG
CTGTGCCAGGACCATGGCCTGACCCCGGACCAGGTGGTGGCCATCGCCAGCCACGATGGCGGCAAG
CAGGCTTTGGAGACGGTACAGCGGCTGTTGCCGGTGCTGTGCCAGGACCATGGCCTGACCCCGGAC
CAGGTCGTGGCCATCGCCAGCAATGGCGGCGGCAAGCAGGCATTGGAGACGGTACAGCGGCTGTTG
CCGGTGCTGTGCCAGGACCATGGCCTGACCCCGGACCAGGTCGTGGCCATCGCCAGCAATGGCGGC
GGCAAGCAGGCCCTGGAGACGGTACAGCGGCTGTTGCCGGTGCTGTGCCAGGACCATGGCCTGACC
CAGGACCAGGTGGTGGCCATCGCCAGCCACGATGGCGGCAAGCAGGCACTGGAAACACTGCAGCGG
CTGTTGCCGGTGCTGTGCCAGGACCATGGCCTGACCCCGGACCAGGTGGTGGCCATCGCCAGCCAC
GATGGCGGCAAGCAGGCCTTGGAGACGGTGCAGCGGCTGTTGCCGGTGCTGTGCCAGGCCCATGGC
CTGACCCCGGCCCAAGTGGTGGCCATCGCCAGCAATGGCGGCGGCAAGCAGGCTCTGGAGACGGTA
CAGCGGCTGTTGCCGGTGCTGTGCCAGGACCATGGCCTGACCCCGGACCAGGTCGTGGCCATCGCC
AGCAATATTGGCGGCAAGCAGGCGTTGGAGACGGTACAGCGGCTGTTGCCGGTGCTGTGCCAGGAC
CATGGCCTGACCCCGGACCAGGTCGTGGCCATCGCCAACAATAACGGCGGCAAGCAGGCTTTGGAG
ACGGTACAGCGGCTGTTGCCGGTGCTGTGCCAGGGCCATGGCCTGACCCAGGACCAGGTGGTGGCC
ATCGCCAGCCACGATGGCGGCAAGCAGGCATTGGAGACGGTACAGCGGCTGTTGCCGGTGCTGTGC
CAGGACCATGGCCTGACCCCGGACCAGGTGGTGGCCATCGCCAGCAATATTGGCGGCAAGCAGGCC
CTGGAGACGGTACAGCGGCTGTTGCCGGTGCTGTGCCAGGACCATGGCCTGACCCCGGACCAGGTG
GTGGCCATCGCCAGCCACGATGGCGGCAAGCAGGCACTGGAGACTGTACAGCGGCTGTTGCCGGTG
CTGTGCCAGGACCATGGCCTGACCCCGGACCAGGTCGTGGCCATCGCCAGCAATGGCGGCGGCAAG
CAGGCCTTGGAGACGGTGCAGCGGCTGTTGCCGGTGCTGTGCCAGGACCATGGCCTGACCCCGGAC
CAGGTGGTGGCCATCGCCAGCAATATTGGCGGCAAGCAGGCTCTGGAGACGGTACAGCGGCTGTTG
CCGGTGCTGTGCCAGGACCATGGCCTGACCCCGGACCAGGTCGTGGCCATCGCCAGCAATGGCGGC
GGCAAGCAGGCGTTGGAGACGGTACAGCGGCTGTTGCCGGTGCTGTGCCAGGACCATGGCCTGACC
CCGGACCAGGTGGTGGCCATCGCCAGCAATATTGGCGGCAAGCAGGCTTTGGAGACGGTACAGCGG
CTGTTGCCGGTGCTGTGCCAGGACCATGGCCTGACCCCGGACCAGGTCGTGGCCATCGCCAGCAAT
GGCGGCGGCAAGCAGGCATTGGAGACGGTACAGCGGCTGTTGCCGGTGCTGTGCCAGGACCATGGC
CTGACCCCGGACCAGGTGGTGGCCATCGCCAGCAATATTGGCGGCAAGCAGGCCCTGGAGACGGTA
CAGCGGCTGTTGCCGGTGCTGTGCCAGGACCATGGCCTGACCCCGGACCAGGTGGTGGCCATCGCC
AGCAATATTGGCGGCAAGCAGGCACTGGAGACGATTGTTGCCCAGTTATCTCGCCCTGATCCGGCG
TTGGCCGCGTTGACCAACGACCACCTCGTCGCCTTGGCCTGCCTCGGCGGACGTCCTGCCCTGGAT
GCAGTGAAAAAGGGATTGCCGCACGCGCCGGAATTGATCAGAAGAATCAATCGCCGCATTCCCGAA

FIG. 8A-1

CGCACGTCCCATCGCGTTCCCGACCTCGCGCACGTGGTTCGCGTGCTTGGTTTTTTCCAGAGCCAC
TCCCACCCAGCGCAAGCATTCGATGACGCCATGACGCAGTTCGAGATGAGCAGGCACGGCTTGGTA
CAGCTCTTTCGCAGAGTGGGCGTCACCGAATTCGAAGCCCGCTACGGAACGCTCCCCCCAGCCTCG
CAGCGTTGGGACCGTATCCTCCAGGCATCAGGGATGAAAAGGGCCAAACCGTCCCCTACTTCAGCT
CAAACACCGGATCAGGCGTCTTTGCATGCAGATTACAAGGACGACGACGACAAGAAGGATTACAAG
GACGACGACGACAAGAAGGGTCGACCCAGCCCAATGCACGAGGGAGATCAGACAGGGGCAAGCAGC
CGTAAACGGTCCCGATCGGATCGTGCTGTCACCGGCCCCTCCGCACAGCAATCTTTCGAGGTGCGC
GTTCCCGAACAGCGCGATGCGCTGCATTTGCCCCTCAGCTGGAGGGTAAAACGCCCGCGTACCAGG
ATCGGGGGCGGCCTCCCGGATCCTGGTACGCCCATCGCTGCCGACCTGGCAGCGTCCAGCACCGTG
ATCagatccCAGCTAGTGAAATCTGAATTGGAAGAGAAGAAATCTGAACTTAGACATAAATTGAAA
TATGTGCCACATGAATATATTGAATTGATTGAAATCGCAAGAAATTCAACTCAGGATAGAATCCTT
GAAATGAAGGTGATGGAGTTCTTTATGAAGGTTTATGGTTATCGTGGTAAACATTTGGGTGGATCA
AGGAAACCAGACGGAGCAATTTATACTGTCGGATCTCCTATTGATTACGGTGTGATCGTTGATACT
AAGGCATATTCAGGAGGTTATAATCTTCCAATTGGTCAAGCAGATGAAATGCAAAGATATGTCGAA
GAGAATCAAACAAGAAACAAGCATATCAACCCTAATGAATGGTGGAAAGTCTATCCATCTTCAGTA
ACAGAATTTAAGTTCTTGTTTGTGAGTGGTCATTTCAAAGGAAACTACAAAGCTCAGCTTACAAGA
TTGAATCATATCACTAATTGTAATGGAGCTGTTCTTAGTGTAGAAGAGCTTTTGATTGGTGGAGAA
ATGATTAAAGCTGGTACATTGACACTTGAGGAAGTGAGAAGGAAATTTAATAACGGTGAGATAAAC
TTTTAA

FIG. 8A-2 dTALEN-L1 Protein (SEQ ID NO: 26)

MetDPIRSRTPSPARELLPGPQPDRVQPTADRGGAPPAGGPLD
GLPARRTMetSRTRLPSPPAPSPAFSAGSFSDLLRQFDPSLLDT
SLLDSMetPAVGTPHTAAAPAEWDEVQSGLRAADDPPPTVRV
AVTAARPPRAKPAPRRRAAQPSDASPAAQVDLRTLGYSQQQ
QEKIKPKVRSTVAQHHEALVGHGFTHAHIVALSQHPAALGTV
AVKYQHIITALPEATHEDIVGVGKQWSGARALEALLTKAGELR
GPPLQLDTGQLLKIAKRGGVTAVEAVHASRNALTGAPLNLTPA
QVVAIASHDGGKQALETVQRLLPVLCQDHGLTPDQVVAIASN
GGGKQALETVQRLLPVLCQAHGLTPAQVVAIASNGGGKQALE
TVQRLLPVLCQDHGLTQDQVVAIASHDGGKQALETVQRLLPV
LCQDHGLTPDQVVAIASHDGGKQALETVQRLLPVLCQDHGLT
PDQVVAIASNGGGKQALETVQRLLPVLCQDHGLTPDQVVAIA
SNGGGKQALETVQRLLPVLCQDHGLTQDQVVAIASHDGGKQ
ALETLQRLLPVLCQDHGLTPDQVVAIASHDGGKQALETVQRLL
PVLCQAHGLTPAQVVAIASNGGGKQALETVQRLLPVLCQDHG
LTPDQVVAIASNIGGKQALETVQRLLPVLCQDHGLTPDQVVAI
ANNNGGKQALETVQRLLPVLCQGHGLTQDQVVAIASHDGGK
QALETVQRLLPVLCQDHGLTPDQVVAIASNIGGKQALETVQR
LLPVLCQDHGLTPDQVVAIASHDGGKQALETVQRLLPVLCQD
HGLTPDQVVAIASNGGGKQALETVQRLLPVLCQDHGLTPDQV
VAIASNIGGKQALETVQRLLPVLCQDHGLTPDQVVAIASNGG
GKQALETVQRLLPVLCQDHGLTPDQVVAIASNIGGKQALETV
QRLLPVLCQDHGLTPDQVVAIASNGGGKQALETVQRLLPVLC
QDHGLTPDQVVAIASNIGGKQALETVQRLLPVLCQDHGLTPD
QVVAIASNIGGKQALETIVAQLSRPDPALAALTNDHLVALACL
GGRPALDAVKKGLPHAPELIRRINRRIPERTSHRVPDLAHVVR
VLGFFQSHSHPAQAFDDAMetTQFEMetSRHGLVQLFRRVGVT
EFEARYGTLPPASQRWDRILQASGMetKRAKPSPTSAQTPDQA
SLHADYKDDDDKKDYKDDDDKKGRPSPMetHEGDQTGASSRK
RSRSDRAVTGPSAQQSFEVRVPEQRDALHLPLSWRVKRPRTRI
GGGLPDPGTPIAADLAASSTVIRSQLVKSELEEKKSELRHKLKY
VPHEYIELIEIARNSTQDRILEMetKVMetEFFMetKVYGYRGKHL
GGSRKPDGAIYTVGSPIDYGVIVDTKAYSGGYNLPIGQADE
MetQRYVEENQTRNKHINPNEWWKVYPSSVTEFKFLFVSGHF
KGNYKAQLTRLNHITNCNGAVLSVEELLIGGEMetIKAGTLTLE
EVRRKFNNGEINFStop

FIG. 8B

2. dTALEN-R1 (SEQ ID NO: 21)

ATGGATCCCATTCGTTCGCGCACGCCAAGTCCTGCCCGCGAGCTTCTGCCCGGACCCCAACCGGAT
AGGGTTCAGCCGACTGCAGATCGGGGGGGGGCTCCGCCTGCTGGCGGCCCCCTGGATGGCTTGCCC
GCTCGGCGGACGATGTCCCGGACCCGGCTGCCATCTCCCCCTGCGCCCTCGCCTGCGTTCTCGGCG
GGCAGCTTCAGCGATCTGCTCCGTCAGTTCGATCCGTCGCTTCTTGATACATCGCTTCTTGATTCG
ATGCCTGCCGTCGGCACGCCGCATACAGCGGCTGCCCCAGCAGAGTGGGATGAGGTGCAATCGGGT
CTGCGTGCAGCCGATGACCCGCCACCCACCGTGCGTGTCGCTGTCACTGCCGCGCGGCCGCCGCGC
GCCAAGCCGGCCCCGCGACGGCGTGCGGCGCAACCCTCCGACGCTTCGCCGGCCGCGCAGGTGGAT
CTACGCACGCTCGGCTACAGTCAGCAGCAGCAAGAGAAGATCAAACCGAAGGTGCGTTCGACAGTG
GCGCAGCACCACGAGGCACTGGTGGGCCATGGGTTTACACACGCGCACATCGTTGCGCTCAGCCAA
CACCCGGCAGCGTTAGGGACCGTCGCTGTCAAGTATCAGCACATAATCACGGCGTTGCCAGAGGCG
ACACACGAAGACATCGTTGGCGTCGGCAAACAGTGGTCCGGCGCACGCGCCCTGGAGGCCTTGCTC
ACGAAGGCGGGGGAGTTGAGAGGTCCGCCGTTACAGTTGGACACAGGCCAACTTCTCAAGATTGCA
AAACGTGGCGGCGTGACCGCAGTGGAGGCAGTGCATGCATCGCGCAATGCACTGACGGGTGCCCCC
CTGAACCTGACCCCGGCACAGGTGGTGGCCATCGCCAACAATAACGGCGGCAAGCAGGCGCTGGAG
ACGGTGCAGCGGCTGTTGCCGGTGCTGTGCCAGGACCATGGCCTGACCCAGGACCAGGTGGTGGCC
ATCGCCAGCCACGATGGCGGCAAGCAGGCCTTGGAGACGGTGCAGCGGCTGTTGCCGGTGCTGTGC
CAGGCCCATGGCCTGACCCCGGCCCAAGTGGTGGCCATCGCCAGCAATGGCGGCGGCAAGCAGGCT
CTGGAGACGGTACAGCGGCTGTTGCCGGTGCTGTGCCAGGACCATGGCCTGACCCCGGACCAGGTC
GTGGCCATCGCCAGCAATGGCGGCGGCAAGCAGGCGTTGGAGACGGTACAGCGGCTGTTGCCGGTG
CTGTGCCAGGACCATGGCCTGACCCCGGACCAGGTGGTGGCCATCGCCAACAATAACGGCGGCAAG
CAGGCTTTGGAGACGGTACAGCGGCTGTTGCCGGTGCTGTGCCAGGACCATGGCCTGACCCCGGAC
CAGGTGGTGGCCATCGCCAGCAATATTGGCGGCAAGCAGGCATTGGAGACGGTACAGCGGCTGTTG
CCGGTGCTGTGCCAGGACCATGGCCTGACCCCGGACCAGGTCGTGGCCATCGCCAGCAATATTGGC
GGCAAGCAGGCCCTGGAGACGGTACAGCGGCTGTTGCCGGTGCTGTGCCAGGACCATGGCCTGACC
CCGGACCAGGTCGTGGCCATCGCCAACAATAACGGCGGCAAGCAGGCACTGGAAACACTGCAGCGG
CTGTTGCCGGTGCTGTGCCAGGACCATGGCCTGACCCCGGACCAGGTCGTGGCCATCGCCAACAAT
AACGGCGGCAAGCAGGCCTTGGAGACGGTGCAGCGGCTGTTGCCGGTGCTGTGCCAGGACCATGGC
CTGACCCCGGACCAAGTCGTGGCCATCGCCAGCCACGATGGCGGCAAGCAGGCTCTGGAGACGGTA
CAGCGGCTGTTGCCGGTGCTGTGCCAGGACCATGGCCTGACCCCGGACCAGGTCGTGGCCATCGCC
AGCAATGGCGGCGGCAAGCAGGCGTTGGAGACGGTACAGCGGCTGTTGCCGGTGCTGTGCCAGGAC
CATGGCCTGACCCCGGACCAGGTCGTGGCCATCGCCAGCAATGGCGGCGGCAAGCAGGCTTTGGAG
ACGGTACAGCGGCTGTTGCCGGTGCTGTGCCAGGACCATGGCCTGACCCCGGACCAGGTGGTGGCC
ATCGCCAACAATAACGGCGGCAAGCAGGCATTGGAGACGGTACAGCGGCTGTTGCCGGTGCTGTGC
CAGGACCATGGCCTGACCCCGGACCAGGTCGTGGCCATCGCCAGCAATATTGGCGGCAAGCAGGCC
CTGGAGACGGTACAGCGGCTGTTGCCGGTGCTGTGCCAGGACCATGGCCTGACCCCGGACCAGGTC
GTGGCCATCGCCAGCAATGGCGGCGGCAAGCAGGCACTGGAGACTGTACAGCGGCTGTTGCCGGTG
CTGTGCCAGGACCATGGCCTGACCCCGGACCAGGTCGTGGCCATCGCCAACAATAACGGCGGCAAG
CAGGCCTTGGAGACGGTGCAGCGGCTGTTGCCGGTGCTGTGCCAGGACCATGGCCTGACCCCGGAC
CAGGTGGTGGCCATCGCCAGCAATATTGGCGGCAAGCAGGCTCTGGAGACGGTACAGCGGCTGTTG
CCGGTGCTGTGCCAGGACCATGGCCTGACCCCGGACCAGGTGGTGGCCATCGCCAACAATAACGGC
GGCAAGCAGGCGTTGGAGACGGTACAGCGGCTGTTGCCGGTGCTGTGCCAGGACCATGGCCTGACC
CAGGACCAGGTGGTGGCCATCGCCAGCCACGATGGCGGCAAGCAGGCTTTGGAGACGGTACAGCGG
CTGTTGCCGGTGCTGTGCCAGGACCATGGCCTGACCCCGGACCAGGTCGTGGCCACCGCCAGCAAT
GGCGGCGGCAAGCAGGCATTGGAGACGGTACAGCGGCTGTTGCCGGTGCTGTGCCAGGACCATGGC
CTGACCCCGGACCAGGTCGTGGCCATCGCCAGCAATGGCGGCGGCAAGCAGGCCCTGGAGACGGTA
CAGCGGCTGTTGCCGGTGCTGTGCCAGGACCATGGCCTGACCCCGGACCAGGTCGTGGCCATCGCC
AGCAATATTGGCGGCAAGCAGGCACTGGAGACGATTGTTGCCCAGTTATCTCGCCCTGATCCGGCG
TTGGCCGCGTTGACCAACGACCACCTCGTCGCCTTGGCCTGCCTCGGCGGACGTCCTGCCCTGGAT
GCAGTGAAAAAGGGATTGCCGCACGCGCCGGAATTGATCAGAAGAATCAATCGCCGCATTCCCGAA

*FIG. 8C-1*

CGCACGTCCCATCGCGTTCCCGACCTCGCGCACGTGGTTCGCGTGCTTGGTTTTTTCCAGAGCCAC
TCCCACCCAGCGCAAGCATTCGATGACGCCATGACGCAGTTCGAGATGAGCAGGCACGGCTTGGTA
CAGCTCTTTCGCAGAGTGGGCGTCACCGAATTCGAAGCCCGCTACGGAACGCTCCCCCCAGCCTCG
CAGCGTTGGGACCGTATCCTCCAGGCATCAGGGATGAAAAGGGCCAAACCGTCCCCTACTTCAGCT
CAAACACCGGATCAGGCGTCTTTGCATGCAGATTACAAGGACGACGACGACAAGAAGGATTACAAG
GACGACGACGACAAGAAGGGTCGACCCAGCCCAATGCACGAGGGAGATCAGACGCGGGCAAGCAGC
CGTAAACGGTCCCGATCGGATCGTGCTGTCACCGGCCCCTCCACACAGCAATCTTTCGAGGTGCGC
GTTCCCGAACAGCAAGATGCGCTGCATTTGCCCCTCAGCTGGAGGGTAAAACGCCCGCGTACCAGG
ATCGGGGGCGGCCTCCCGGATCCTGGTACGCCCATCGCTGCCGACCTGGCAGCGTCCAGCACCGTG
ATGTGGGAACAAGATGCGGCCCCCTTCGCAGGGGCAGCGGATGATTTCCCGGCATTCAACGAAGAG
GAGCTCGCATGGTTGATGGAGCTATTGCCTCAGTCAGGCTCAGTCGGAGGGACGATCTCTAGACAG
CTAGTGAAATCTGAATTGGAAGAGAAGAAATCTGAACTTAGACATAAATTGAAATATGTGCCACAT
GAATATATTGAATTGATTGAAATCGCAAGAAATTCAACTCAGGATAGAATCCTTGAAATGAAGGTG
ATGGAGTTCTTTATGAAGGTTTATGGTTATCGTGGTAAACATTTGGGTGGATCAAGGAAACCAGAC
GGAGCAATTTATACTGTCGGATCTCCTATTGATTACGGTGTGATCGTTGATACTAAGGCATATTCA
GGAGGTTATAATCTTCCAATTGGTCAAGCAGATGAAATGCAAAGATATGTCGAAGAGAATCAAACA
AGAAACAAGCATATCAACCCTAATGAATGGTGGAAAGTCTATCCATCTTCAGTAACAGAATTTAAG
TTCTTGTTTGTGAGTGGTCATTTCAAAGGAAACTACAAAGCTCAGCTTACAAGATTGAATCATATC
ACTAATTGTAATGGAGCTGTTCTTAGTGTAGAAGAGCTTTTGATTGGTGGAGAAATGATTAAAGCT
GGTACATTGACACTTGAGGAAGTGAGAAGGAAATTTAATAACGGCGAGATAAACTTTTAA

FIG. 8C-2 dTALEN-R1 Protein (SEQ ID NO: 24)

Met D P I R S R T P S P A R E L L P G P Q P D R V Q P T A D R G G A P P A G G P L D
G L P A R R T Met S R T R L P S P P A P S P A F S A G S F S D L L R Q F D P S L L D T
S L L D S Met P A V G T P H T A A A P A E W D E V Q S G L R A A D D P P P T V R V
A V T A A R P P R A K P A P R R R A A Q P S D A S P A A Q V D L R T L G Y S Q Q Q
Q E K I K P K V R S T V A Q H H E A L V G H G F T H A H I V A L S Q H P A A L G T V
A V K Y Q H I I T A L P E A T H E D I V G V G K Q W S G A R A L E A L L T K A G E L R
G P P L Q L D T G Q L L K I A K R G G V T A V E A V H A S R N A L T G A P L N L T P A
Q V V A I A N N N G G K Q A L E T V Q R L L P V L C Q D H G L T Q D Q V V A I A S H
D G G K Q A L E T V Q R L L P V L C Q A H G L T P A Q V V A I A S N G G G K Q A L E
T V Q R L L P V L C Q D H G L T P D Q V V A I A S N G G G K Q A L E T V Q R L L P V
L C Q D H G L T P D Q V V A I A N N N G G K Q A L E T V Q R L L P V L C Q D H G L T
P D Q V V A I A S N I G G K Q A L E T V Q R L L P V L C Q D H G L T P D Q V V A I A S
N I G G K Q A L E T V Q R L L P V L C Q D H G L T P D Q V V A I A N N N G G K Q A L
E T L Q R L L P V L C Q D H G L T P D Q V V A I A N N N G G K Q A L E T V Q R L L P
V L C Q D H G L T P D Q V V A I A S H D G G K Q A L E T V Q R L L P V L C Q D H G L
T P D Q V V A I A S N G G G K Q A L E T V Q R L L P V L C Q D H G L T P D Q V V A I
A S N G G G K Q A L E T V Q R L L P V L C Q D H G L T P D Q V V A I A N N N G G K
Q A L E T V Q R L L P V L C Q D H G L T P D Q V V A I A S N I G G K Q A L E T V Q R
L L P V L C Q D H G L T P D Q V V A I A S N G G G K Q A L E T V Q R L L P V L C Q D
H G L T P D Q V V A I A N N N G G K Q A L E T V Q R L L P V L C Q D H G L T P D Q
V V A I A S N I G G K Q A L E T V Q R L L P V L C Q D H G L T P D Q V V A I A N N N
G G K Q A L E T V Q R L L P V L C Q D H G L T Q D Q V V A I A S H D G G K Q A L E T
V Q R L L P V L C Q D H G L T P D Q V V A T A S N G G G K Q A L E T V Q R L L P V L
C Q D H G L T P D Q V V A I A S N G G G K Q A L E T V Q R L L P V L C Q D H G L T P
D Q V V A I A S N I G G K Q A L E T I V A Q L S R P D P A L A A L T N D H L V A L A C
L G G R P A L D A V K K G L P H A P E L I R R I N R R I P E R T S H R V P D L A H V V
R V L G F F Q S H S H P A Q A F D D A Met T Q F E Met S R H G L V Q L F R R V G V
T E F E A R Y G T L P P A S Q R W D R I L Q A S G Met K R A K P S P T S A Q T P D Q
A S L H A D Y K D D D D K K D Y K D D D D K K G R P S P Met H E G D Q T R A S S R
K R S R S D R A V T G P S T Q Q S F E V R V P E Q Q D A L H L P L S W R V K R P R T
R I G G G L P D P G T P I A A D L A A S S T V Met W E Q D A A P F A G A A D D F P
A F N E E E L A W L Met E L L P Q S G S V G G T I S R Q L V K S E L E E K K S E L R H
K L K Y V P H E Y I E L I E I A R N S T Q D R I L E Met K V Met E F F Met K V Y G Y R
G K H L G G S R K P D G A I Y T V G S P I D Y G V I V D T K A Y S G G Y N L P I G Q A
D E Met Q R Y V E E N Q T R N K H I N P N E W W K V Y P S S V T E F K F L F V S G
H F K G N Y K A Q L T R L N H I T N C N G A V L S V E E L L I G G E Met I K A G T L T
L E E V R R K F N N G E I N F Stop 3.

FIG. 8D dTALEN-R2 (SEQ ID NO: 22)

ATGGATCCCATTCGTTCGCGCACGCCAAGTCCTGCCCGCGAGCTTCTGCCCGGACCCCAACCGGAT
AGGGTTCAGCCGACTGCAGATCGGGGGGGGCTCCGCCTGCTGGCGGCCCCCTGGATGGCTTGCCC
GCTCGGCGGACGATGTCCCGGACCCGGCTGCCATCTCCCCCTGCGCCCTCGCCTGCGTTCTCGGCG
GGCAGCTTCAGCGATCTGCTCCGTCAGTTCGATCCGTCGCTTCTTGATACATCGCTTCTTGATTCG
ATGCCTGCCGTCGGCACGCCGCATACAGCGGCTGCCCCAGCAGAGTGGGATGAGGTGCAATCGGGT
CTGCGTGCAGCCGATGACCCGCCACCCACCGTGCGTGTCGCTGTCACTGCCGCGCGGCCGCCGCGC
GCCAAGCCGGCCCCGCGACGGCGTGCGGCGCAACCCTCCGACGCTTCGCCGGCCGCGCAGGTGGAT
CTACGCACGCTCGGCTACAGTCAGCAGCAGCAAGAGAAGATCAAACCGAAGGTGCGTTCGACAGTG
GCGCAGCACCACGAGGCACTGGTGGGCCATGGGTTTACACACGCGCACATCGTTGCGCTCAGCCAA
CACCCGGCAGCGTTAGGGACCGTCGCTGTCAAGTATCAGCACATAATCACGGCGTTGCCAGAGGCG
ACACACGAAGACATCGTTGGCGTCGGCAAACAGTGGTCCGGCGCACGCGCCCTGGAGGCCTTGCTC
ACGAAGGCGGGGGAGTTGAGAGGTCCGCCGTTACAGTTGGACACAGGCCAACTTCTCAAGATTGCA
AAACGTGGCGGCGTGACCGCAGTGGAGGCAGTGCATGCATGGCGCAATGCACTGACGGGTGCCCCC
CTGAACCTGACCCCGGCACAGGTGGTGGCCATCGCCAGCCACGATGGCGGCAAGCAGGCGCTGGAG
ACGGTGCAGCGGCTGTTGCCGGTGCTGTGCCAGGACCATGGCCTGACCCCGGACCAGGTGGTGGCC
ATCGCCAGCAATATTGGCGGCAAGCAGGCCTTGGAGACGGTGCAGCGGCTGTTGCCGGTGCTGTGC
CAGGACCATGGCCTGACCCCGGACCAAGTGGTGGCCATCGCCAACAATAACGGCGGCAAGCAGGCT
CTGGAGACGGTACAGCGGCTGTTGCCGGTGCTGTGCCAGGACCATGGCCTGACCCCGGACCAGGTG
GTGGCCATCGCCAGCCACGATGGCGGCAAGCAGGCGTTGGAGACGGTACAGCGGCTGTTGCCGGTG
CTGTGCCAGGACCATGGCCTGACCCCGGACCAGGTCGTGGCCATCGCCAGCAATGGCGGCGGCAAG
CAGGCTTTGGAGACGGTACAGCGGCTGTTGCCGGTGCTGTGCCAGGACCATGGCCTGACCCCGGAC
CAGGTCGTGGCCATCGCCAGCAATATTGGCGGCAAGCAGGCATTGGAGACGGTACAGCGGCTGTTG
CCGGTGCTGTGCCAGGACCATGGCCTGACCCCGGACCAGGTGGTGGCCATCGCCAGCCACGATGGC
GGCAAGCAGGCCCTGGAGACGGTACAGCGGCTGTTGCCGGTGCTGTGCCAGGACCATGGCCTGACC
CCGGACCAGGTCGTGGCCATCGCCAGCAATGGCGGCGGCAAGCAGGCACTGGAAACACTGCAGCGG
CTGTTGCCGGTGCTGTGCCAGGACCATGGCCTGACCCCGGACCAGGTGGTGGCCATCGCCAGCAAT
ATTGGCGGCAAGCAGGCCTTGGAGACGGTGCAGCGGCTGTTGCCGGTGCTGTGCCAGGACCATGGC
CTGACCCCGGACCAAGTCGTGGCCATCGCCAGCCACGATGGCGGCAAGCAGGCTCTGGAGACGGTA
CAGCGGCTGTTGCCGGTGCTGTGCCAGGACCATGGCCTGACCCCGGACCAGGTCGTGGCCATCGCC
AGCAATGGCGGCGGCAAGCAGGCGTTGGAGACGGTACAGCGGCTGTTGCCGGTGCTGTGCCAGGAC
CATGGCCTGACCCCGGACCAGGTCGTGGCCATCGCCAGCAATGGCGGCGGCAAGCAGGCTTTGGAG
ACGGTACAGCGGCTGTTGCCGGTGCTGTGCCAGGACCATGGCCTGACCCCGGACCAGGTGGTGGCC
ATCGCCAACAATAACGGCGGCAAGCAGGCATTGGAGACGGTACAGCGGCTGTTGCCGGTGCTGTGC
CAGGACCATGGCCTGACCCCGGACCAGGTGGTGGCCATCGCCAGCAATATTGGCGGCAAGCAGGCC
CTGGAGACGGTACAGCGGCTGTTGCCGGTGCTGTGCCAGGACCATGGCCTGACCCCGGACCAGGTC
GTGGCCATCGCCAACAATAACGGCGGCAAGCAGGCactggagaCTGTACAGCGGCTGTTGCCGGTG
CTGTGCCAGGACCATGGCCTGACCCCGGACCAGGTCGTGGCCATCGCCAGCAATGGCGGCGGCAAG
CAGGCCTTGGAGACGGTGCAGCGGCTGTTGCCGGTGCTGTGCCAGGCCCATGGCCTGACCCCGGCC
CAAGTGGTGGCCATCGCCAGCAATGGCGGCGGCAAGCAGGCTCTGGAGACGGTACAGCGGCTGTTG
CCGGTGCTGTGCCAGGACCATGGCCTGACCCCGGACCAGGTCGTGGCCATCGCCAGCAATGGCGGC
GGCAAGCAGGCGTTGGAGACGGTACAGCGGCTGTTGCCGGTGCTGTGCCAGGACCATGGCCTGACC
CCGGACCAGGTCGTGGCCATCGCCAACAATAACGGCGGCAAGCAGGCTTTGGAGACGGTACAGCGG
CTGTTGCCGGTGCTGTGCCAGGACCATGGCCTGACCCCGGACCAGGTGGTGGCCATCGCCAGCCAC
GATGGCGGCAAGCAGGCATTGGAGACGGTACAGCGGCTGTTGCCGGTGCTGTGCCAGGACCATGGC
CTGACCCCGGACCAGGTCGTGGCCATCGCCAGCAATGGCGGCGGCAAGCAGGCCCTGGAGACGGTA
CAGCGGCTGTTGCCGGTGCTGTGCCAGGACCATGGCCTGACCCCGGACCAGGTCGTGGCCATCGCC
AGCAATGGCGGCGGCAAGCAGGCACTGGAGACGGTACAGCGGCTGTTGCCGGTGCTGTGCCAGGAC
CATGGCCTGACCCCGAACCAGGTGGTGGCCATCGCCAGCAATGGCGGCaAGCAGGCGCTGGAGAGC
ATTGTTGCCCAGTTATCTCGCCCTGATCCGGCGTTGGCCGCGTTGAcCAACGAcCACCTCGTCGCC
TTGGCCTGCCTCGGCGGACGTCCTGCCCTGGATGCAGTGAAAAAGGGATTGCCGCACGCGCCGGAA

FIG. 8E-1

TTGATCAGAAGAATCAATCGCCGCATTCCCGAACGCACGTCCCATCGCGTTCCCGACCTCGCGCAC
GTGGTTCGCGTGCTTGGTTTTTTCCAGAGCCACTCCCACCCAGCGCAAGCATTCGATGACGCCATG
ACGCAGTTCGAGATGAGCAGGCACGGCTTGGTACAGCTCTTTCGCAGAGTGGGCGTCACCGAATTC
GAAGCCCGCTACGGAACGCTCCCCCCAGCCTCGCAGCGTTGGGACCGTATCCTCCAGGCATCAGGG
ATGAAAAGGGCCAAACCGTCCCCTACTTCAGCTCAAACACCGGATCAGGCGTCTTTGCATGCAGAT
TACAAGGACGACGACGACAAGAAGGATTACAAGGACGACGACGACAAGAAGGGTCGACCCAGCCCA
ATGCACGAGGGAGATCAGACGCGGGCAAGCAGCCGTAAACGGTCCCGATCGGATCGTGCTGTCACC
GGCCCCTCCACACAGCAATCTTTCGAGGTGCGCGTTCCCGAACAGCAAGATGCGCTGCATTTGCCC
CTCAGCTGGAGGGTAAAACGCCCGCGTACCAGGATCGGGGGCGGCCTCCCGGATCCTGGTACGCCC
ATCGCTGCCGACCTGGCAGCGTCCAGCACCGTGATGTGGGAACAAGATGCGGCCCCCTTCGCAGGG
GCAGCGGATGATTTCCCGGCATTCAACGAAGAGGAGCTCGCATGGTTGATGGAGCTATTGCCTCAG
TCAGGCTCAGTCGGAGGGACGATCTCTAGACAGCTAGTGAAATCTGAATTGGAAGAGAAGAAATCT
GAACTTAGACATAAATTGAAATATGTGCCACATGAATATATTGAATTGATTGAAATCGCAAGAAAT
TCAACTCAGGATAGAATCCTTGAAATGAAGGTGATGGAGTTCTTTATGAAGGTTTATGGTTATCGT
GGTAAACATTTGGGTGGATCAAGGAAACCAGACGGAGCAATTTATACTGTCGGATCTCCTATTGAT
TACGGTGTGATCGTTGATACTAAGGCATATTCAGGAGGTTATAATCTTCCAATTGGTCAAGCAGAT
GAAATGCAAAGATATGTCGAAGAGAATCAAACAAGAAACAAGCATATCAACCCTAATGAATGGTGG
AAAGTCTATCCATCTTCAGTAACAGAATTTAAGTTCTTGTTTGTGAGTGGTCATTTCAAAGGAAAC
TACAAAGCTCAGCTTACAAGATTGAATCATATCACTAATTGTAATGGAGCTGTTCTTAGTGTAGAA
GAGCTTTTGATTGGTGGAGAAATGATTAAAGCTGGTACATTGACACTTGAGGAAGTGAGAAGGAAA
TTTAATAACGGCGAGATAAACTTTTAA

FIG. 8E-2 dTALEN-R2 Protein (SEQ ID NO: 25)

Met D P I R S R T P S P A R E L L P G P Q P D R V Q P T A D R G G A P P A G G P L D
G L P A R R T Met S R T R L P S P P A P S P A F S A G S F S D L L R Q F D P S L L D T
S L L D S Met P A V G T P H T A A A P A E W D E V Q S G L R A A D D P P P T V R V
A V T A A R P P R A K P A P R R R A A Q P S D A S P A A Q V D L R T L G Y S Q Q Q
Q E K I K P K V R S T V A Q H H E A L V G H G F T H A H I V A L S Q H P A A L G T V
A V K Y Q H I I T A L P E A T H E D I V G V G K Q W S G A R A L E A L L T K A G E L R
G P P L Q L D T G Q L L K I A K R G G V T A V E A V H A W R N A L T G A P L N L T P
A Q V V A I A S H D G G K Q A L E T V Q R L L P V L C Q D H G L T P D Q V V A I A S
N I G G K Q A L E T V Q R L L P V L C Q D H G L T P D Q V V A I A N N N G G K Q A L
E T V Q R L L P V L C Q D H G L T P D Q V V A I A S H D G G K Q A L E T V Q R L L P
V L C Q D H G L T P D Q V V A I A S N G G G K Q A L E T V Q R L L P V L C Q D H G L
T P D Q V V A I A S N I G G K Q A L E T V Q R L L P V L C Q D H G L T P D Q V V A I A
S H D G G K Q A L E T V Q R L L P V L C Q D H G L T P D Q V V A I A S N G G G K Q
A L E T L Q R L L P V L C Q D H G L T P D Q V V A I A S N I G G K Q A L E T V Q R L L
P V L C Q D H G L T P D Q V V A I A S H D G G K Q A L E T V Q R L L P V L C Q D H G
L T P D Q V V A I A S N G G G K Q A L E T V Q R L L P V L C Q D H G L T P D Q V V A
I A S N G G G K Q A L E T V Q R L L P V L C Q D H G L T P D Q V V A I A N N N G G K
Q A L E T V Q R L L P V L C Q D H G L T P D Q V V A I A S N I G G K Q A L E T V Q R
L L P V L C Q D H G L T P D Q V V A I A N N N G G K Q A L E T V Q R L L P V L C Q D
H G L T P D Q V V A I A S N G G G K Q A L E T V Q R L L P V L C Q A H G L T P A Q V
V A I A S N G G G K Q A L E T V Q R L L P V L C Q D H G L T P D Q V V A I A S N G G
G K Q A L E T V Q R L L P V L C Q D H G L T P D Q V V A I A N N N G G K Q A L E T V
Q R L L P V L C Q D H G L T P D Q V V A I A S H D G G K Q A L E T V Q R L L P V L C
Q D H G L T P D Q V V A I A S N G G G K Q A L E T V Q R L L P V L C Q D H G L T P D
Q V V A I A S N G G G K Q A L E T V Q R L L P V L C Q D H G L T P N Q V V A I A S N
G G K Q A L E S I V A Q L S R P D P A L A A L T N D H L V A L A C L G G R P A L D A V
K K G L P H A P E L I R R I N R R I P E R T S H R V P D L A H V V R V L G F F Q S H S H
P A Q A F D D A Met T Q F E Met S R H G L V Q L F R R V G V T E F E A R Y G T L P
P A S Q R W D R I L Q A S G Met K R A K P S P T S A Q T P D Q A S L H A D Y K D D
D D K K D Y K D D D D K K G R P S P Met H E G D Q T R A S S R K R S R S D R A V T
G P S T Q Q S F E V R V P E Q Q D A L H L P L S W R V K R P R T R I G G G L P D P G
T P I A A D L A A S S T V Met W E Q D A A P F A G A A D D F P A F N E E E L A W L
Met E L L P Q S G S V G G T I S R Q L V K S E L E E K K S E L R H K L K Y V P H E Y I E
L I E I A R N S T Q D R I L E Met K V Met E F F Met K V Y G Y R G K H L G G S R K P
D G A I Y T V G S P I D Y G V I V D T K A Y S G G Y N L P I G Q A D E Met Q R Y V E E
N Q T R N K H I N P N E W W K V Y P S S V T E F K F L F V S G H F K G N Y K A Q L T
R L N H I T N C N G A V L S V E E L L I G G E Met I K A G T L T L E E V R R K F N N G
E I N F Stop

FIG. 8F

TALEN-L (SEQ ID NO: 36)

GGTACCAGATCTGCCACCATGGATCCCATTCGTTCGCGCACGCCAAGTCCTGCCCGCGAGCTTCTGCCCG
GACCCCAACCGGATAGGGTTCAGCCGACTGCAGATCGGGGGGGGCTCCGCCTGCTGGCGGCCCCCTGGA
TGGCTTGCCCGCTCGGCGGACGATGTCCCGGACCCGGCTGCCATCTCCCCCTGCGCCCTCGCCTGCGTTC
TCGGCGGGCAGCTTCAGCGATCTGCTCCGTCAGTTCGATCCGTCGCTTCTTGATACATCGCTTCTTGATT
CGATGCCTGCCGTCGGCACGCCGCATACAGCGGCTGCCCCAGCAGAGTGGGATGAGGTGCAATCGGGTCT
GCGTGCAGCCGATGACCCGCCACCCACCGTGCGTGTCGCTGTCACTGCCGCGCGGCCGCCGCGCGCCAAG
CCGGCCCCGCGACGGCGTGCGGCGCAACCCTCCGACGCTTCGCCGGCCGCGCAGGTGGATCTACGCACGC
TCGGCTACAGTCAGCAGCAGCAAGAGAAGATCAAACCGAAGGTGCGTTCGACAGTGGCGCAGCACCACGA
GGCACTGGTGGGCCATGGGTTTACACACGCGCACATCGTTGCGCTCAGCCAACACCCGGCAGCGTTAGGG
ACCGTCGCTGTCAAGTATCAGCACATAATCACGGCGTTGCCAGAGGCGACACACGAAGACATCGTTGGCG
TCGGCAAACAGTGGTCCGGCGCACGCGCCCTGGAGGCCTTGCTCACGAAGGCGGGGGAGTTGAGAGGTCC
GCCGTTACAGTTGGACACAGGCCAACTTCTCAAGATTGCAAAACGTGGCGGCGTGACCGCAGTGGAGGCA
GTGCATGCATGGCGCAATGCACTGACGGGTGCCCCCCTGAACCTGACCCCGGACCAAGTGGTGGCCATCG
CCAGCAATGGCGGCGGCAAGCAGGCACTAGAAACGGTGCAGCGGCTGTTGCCGGTGCTGTGCCAGGACCA
TGGCCTGACCCCGGACCAGGTGGTGGCCATCGCCAGCAATATTGGCGGCAAGCAGGCTCTTGAAACGGTG
CAGCGGCTGTTGCCGGTGCTGTGCCAGGACCATGGCCTGACCCCGGACCAAGTGGTGGCCATCGCCAACA
ATAACGGCGGCAAGCAGGCGTTGGAAACGGTGCAGCGGCTGTTGCCGGTGCTGTGCCAGGACCATGGCCT
GACCCCGGACCAGGTCGTGGCCATCGCCAGCAATATTGGCGGCAAGCAGGCGCTCGAAACGGTGCAGCGG
CTGTTGCCGGTGCTGTGCCAGGCCCATGGCCTGACCCCGGACCAAGTGGTGGCCATCGCCAGCAATGGCG
GCGGCAAGCAGGCAGTTGAAACGGTGCAGCGGCTGTTGCCGGTGCTGTGCCAGGACCATGGCCTGACCCC
GGACCAGGTGGTGGCCATCGCCAGCAATATTGGCGGCAAGCAGGCTGTAGAAACGGTGCAGCGGCTGTTG
CCGGTGCTGTGCCAGGCCCATGGCCTGACCCCGGCCCAAGTGGTGGCCATCGCCAGCAATGGCGGCGGCA
AGCAGGCCGTGGAAACGGTGCAGCGGCTGTTGCCGGTGCTGTGCCAGGACCATGGCCTGACCCCGGACCA
AGTGGTGGCCATCGCCAACAATAACGGCGGCAAGCAGGCGGTCGAAACGGTGCAGCGGCTGTTGCCGGTG
CTGTGCCAGGACCATGGCCTGACCCCGGACCAAGTCGTGGCCATCGCCAGCCACGATGGCGGCAAGCAGG
CACTGGAAACACTGCAGCGGCTGTTGCCGGTGCTGTGCCAGGACCATGGCCTGACCCCGGACCAGGTCGT
GGCCATCGCCAGCAATATTGGCGGCAAGCAGGCACTAGAAACGGTGCAGCGGCTGTTGCCGGTGCTGTGC
CAGGCCCATGGCCTGACCCCGGCCCAAGTGGTGGCCATCGCCAGCAATGGCGGCGGCAAGCAGGCTCTTG
AAACGGTGCAGCGGCTGTTGCCGGTGCTGTGCCAGGACCATGGCCTGACCCCGGACCAAGTCGTGGCCAT
CGCCAGCCACGATGGCGGCAAGCAGGCGTTGGAAACGGTGCAGCGGCTGTTGCCGGTGCTGTGCCAGGCC
CATGGCCTGACCCCGGCCCAAGTGGTGGCCATCGCCAGCAATGGCGGCGGCAAGCAGGCGCTCGAAACGG
TGCAGCGGCTGTTGCCGGTGCTGTGCCAGGACCATGGCCTGACCCCGGACCAAGTCGTGGCCATCGCCAG
CCACGATGGCGGCAAGCAGGCAGTTGAAACGGTGCAGCGGCTGTTGCCGGTGCTGTGCCAGGACCATGGC
CTGACCCCGGACCAAGTCGTGGCCATCGCCAGCCACGATGGCGGCAAGCAGGCTGTAGAAACGGTGCAGC
GGCTGTTGCCGGTGCTGTGCCAGGACCATGGCCTGACCCCGGACCAAGTCGTGGCCATCGCCAGCCACGA
TGGCGGCAAGCAGGCCGTGGAAACGGTGCAGCGGCTGTTGCCGGTGCTGTGCCAGGACCATGGCCTGACC
CCGAACCAGGTGGTGGCCATCGCCAGCAATGGCGGCAAGCAGGCGCTGGAGAGCATTGTTGCCCAGTTAT
CTCGCCCTGATCCGGCGTTGGCCGCGTTGACCAACGACCACCTCGTCGCCTTGGCCTGCCTCGGCGGACG
TCCTGCCCTGGATGCAGTGAAAAAGGGATTGCCGCACGCGCCGGAATTGATCAGAAGAATCAATCGCCGC
ATTCCCGAACGCACGTCCCATCGCGTTCCCGACCTCGCGCACGTGGTTCGCGTGCTTGGTTTTTTCCAGA
GCCACTCCCACCCAGCGCAAGCATTCGATGACGCCATGACGCAGTTCGAGATGAGCAGGCACGGCTTGGT
ACAGCTCTTTCGCAGAGTGGGCGTCACCGAATTCGAAGCCCGCTACGGAACGCTCCCCCCAGCCTCGCAG
CGTTGGGACCGTATCCTCCAGGCATCAGGGATGAAAAGGGCCAAACCGTCCCCTACTTCAGCTCAAACAC
CGGATCAGGCGTCTTTACATGCAGATTACAAGGACGACGACGACAAGAAGGATTACAAGGACGACGACGA
CAAGAAGGGTCGACCCAGCCCAATGCACGAGGGAGATCAGACGCGGGCAAGCAGCCGTAAACGGTCCCGA
TCGGATCGTGCTGTCACCGGCCCCTCCACACAGCAATCTTTCGAGGTGCGCGTTCCCGAACAGCAAGATG
CGCTGCATTTGCCCCTCAGCTGGAGGGTAAAACGCCCGCGTACCAGGATCGGGGGCGGCCTCCCGGATCC

FIG. 9A-1

TGGTACGCCCATCGCTGCCGACCTGGCAGCGTCCAGCACCGTGATGTCTAGACAGCTAGTGAAATCTGAA
TTGGAAGAGAAGAAATCTGAACTTAGACATAAATTGAAATATGTGCCACATGAATATATTGAATTGATTG
AAATCGCAAGAAATTCAACTCAGGATAGAATCCTTGAAATGAAGGTGATGGAGTTCTTTATGAAGGTTTA
TGGTTATCGTGGTAAACATTTGGGTGGATCAAGGAAACCAGACGGAGCAATTTATACTGTCGGATCTCCT
ATTGATTACGGTGTGATCGTTGATACTAAGGCATATTCAGGAGGTTATAATCTTCCAATTGGTCAAGCAG
ATGAAATGCAAAGATATGTCGAAGAGAATCAAACAAGAAACAAGCATATCAACCCTAATGAATGGTGGAA
AGTCTATCCATCTTCAGTAACAGAATTTAAGTTCTTGTTTGTGAGTGGTCATTTCAAAGGAAACTACAAA
GCTCAGCTTACAAGATTGAATCATATCACTAATTGTAATGGAGCTGTTCTTAGTGTAGAAGAGCTTTTGA
TTGGTGGAGAAATGATTAAAGCTGGTACATTGACACTTGAGGAAGTGAGAAGGAAATTTAATAACGGTGA
GATAAACTTTTTAATAGACTAGT

FIG. 9A-2

TALEN-R Protein (SEQ ID NO: 37)
MDPIRSRTPSPARELLPGPQPDRVQPTADRGGAPPAGGPLDGLPARRTMSRTRLPSPPAPSPAFSAGSFS
DLLRQFDPSLLDTSLLDSMPAVGTPHTAAAPAEWDEVQSGLRAADDPPPTVRVAVTAARPPRAKPAPRRR
AAQPSDASPAAQVDLRTLGYSQQQQEKIKPKVRSTVAQHHEALVGHGFTHAHIVALSQHPAALGTVAVKY
QHIITALPEATHEDIVGVGKQWSGARALEALLTKAGELRGPPLQLDTGQLLKIAKRGGVTAVEAVHAWRN
ALTGAPLNLTPDQVVAIASNGGGKQALETVQRLLPVLCQDHGLTPDQVVAIASNIGGKQALETVQRLLPV
LCQDHGLTPDQVVAIANNNGGKQALETVQRLLPVLCQDHGLTPDQVVAIASNIGGKQALETVQRLLPVLC
QAHGLTPDQVVAIASNGGGKQAVETVQRLLPVLCQDHGLTPDQVVAIASNIGGKQAVETVQRLLPVLCQA
HGLTPAQVVAIASNGGGKQAVETVQRLLPVLCQDHGLTPDQVVAIANNNGGKQAVETVQRLLPVLCQDHG
LTPDQVVAIASHDGGKQALETLQRLLPVLCQDHGLTPDQVVAIASNIGGKQALETVQRLLPVLCQAHGLT
PAQVVAIASNGGGKQALETVQRLLPVLCQDHGLTPDQVVAIASHDGGKQALETVQRLLPVLCQAHGLTPA
QVVAIASNGGGKQALETVQRLLPVLCQDHGLTPDQVVAIASHDGGKQAVETVQRLLPVLCQDHGLTPDQV
VAIASHDGGKQAVETVQRLLPVLCQDHGLTPDQVVAIASHDGGKQAVETVQRLLPVLCQDHGLTPNQVVA
IASNGGKQALESIVAQLSRPDPALAALTNDHLVALACLGGRPALDAVKKGLPHAPELIRRINRRIPERTS
HRVPDLAHVVRVLGFFQSHSHPAQAFDDAMTQFEMSRHGLVQLFRRVGVTEFEARYGTLPPASQRWDRIL
QASGMKRAKPSPTSAQTPDQASLHADYKDDDDKKDYKDDDDKKGRPSPMHEGDQTRASSRKRSRSDRAVT
GPSTQQSFEVRVPEQQDALHLPLSWRVKRPRTRIGGGLPDPGTPIAADLAASSTVMSRQLVKSELEEKKS
ELRHKLKYVPHEYIELIEIARNSTQDRILEMKVMEFFMKVYGYRGKHLGGSRKPDGAIYTVGSPIDYGVI
VDTKAYSGGYNLPIGQADEMQRYVEENQTRNKHINPNEWWKVYPSSVTEFKFLFVSGHFKGNYKAQLTRL
NHITNCNGAVLSVEELLIGGEMIKAGTLTLEEVRRKFNNGEINF*

FIG. 9B

TALEN-R (SEQ ID NO: 38)

GGTACCAGATCTGCCACCATGGATCCCATTCGTTCGCGCACGCCAAGTCCTGCCCGCGAGCTTCTGCCCG
GACCCCAACCGGATAGGGTTCAGCCGACTGCAGATCGGGGGGGGGCTCCGCCTGCTGGCGGCCCCCTGGA
TGGCTTGCCCGCTCGGCGGACGATGTCCCGGACCCGGCTGCCATCTCCCCCTGCGCCCTCGCCTGCGTTC
TCGGCGGGCAGCTTCAGCGATCTGCTCCGTCAGTTCGATCCGTCGCTTCTTGATACATCGCTTCTTGATT
CGATGCCTGCCGTCGGCACGCCGCATACAGCGGCTGCCCCAGCAGAGTGGGATGAGGTGCAATCGGGTCT
GCGTGCAGCCGATGACCCGCCACCCACCGTGCGTGTCGCTGTCACTGCCGCGCGGCCGCCGCGCGCCAAG
CCGGCCCCGCGACGGCGTGCGGCGCAACCCTCCGACGCTTCGCCGGCCGCGCAGGTGGATCTACGCACGC
TCGGCTACAGTCAGCAGCAGCAAGAGAAGATCAAACCGAAGGTGCGTTCGACAGTGGCGCAGCACCACGA
GGCACTGGTGGGCCATGGGTTTACACACGCGCACATCGTTGCGCTCAGCCAACACCCGGCAGCGTTAGGG
ACCGTCGCTGTCAAGTATCAGCACATAATCACGGCGTTGCCAGAGGCGACACACGAAGACATCGTTGGCG
TCGGCAAACAGTGGTCCGGCGCACGCGCCCTGGAGGCCTTGCTCACGAAGGCGGGGGAGTTGAGAGGTCC
GCCGTTACAGTTGGACACAGGCCAACTTCTCAAGATTGCAAAACGTGGCGGCGTGACCGCAGTGGAGGCA
GTGCATGCATGGCGCAATGCACTGACGGGTGCCCCCCTGAACCTGACCCCGGACCAAGTGGTGGCCATCG
CCAGCAATATTGGCGGCAAGCAGGCACTAGAAACGGTGCAGCGGCTGTTGCCGGTGCTGTGCCAGGCCCA
TGGCCTGACCCCGGCCCAAGTGGTGGCCATCGCCAGCAATGGCGGCGGCAAGCAGGCTCTTGAAACGGTG
CAGCGGCTGTTGCCGGTGCTGTGCCAGGACCATGGCCTGACCCCGGACCAGGTGGTGGCCATCGCCAGCA
ATATTGGCGGCAAGCAGGCGTTGGAAACGGTGCAGCGGCTGTTGCCGGTGCTGTGCCAGGCCCATGGCCT
GACCCCGGCCCAAGTGGTGGCCATCGCCAGCAATGGCGGCGGCAAGCAGGCGCTCGAAACGGTGCAGCGG
CTGTTGCCGGTGCTGTGCCAGGACCATGGCCTGACCCCGGACCAGGTCGTGGCCATCGCCAGCAATATTG
GCGGCAAGCAGGCAGTTGAAACGGTGCAGCGGCTGTTGCCGGTGCTGTGCCAGGACCATGGCCTGACCCC
GGACCAAGTGGTGGCCATCGCCAACAATAACGGCGGCAAGCAGGCTGTAGAAACGGTGCAGCGGCTGTTG
CCGGTGCTGTGCCAGGCCCATGGCCTGACCCCGGCCCAAGTGGTGGCCATCGCCAGCAATGGCGGCGGCA
AGCAGGCCGTGGAAACGGTGCAGCGGCTGTTGCCGGTGCTGTGCCAGGCCCATGGCCTGACCCCGGACCA
AGTGGTGGCCATCGCCAGCAATGGCGGCGGCAAGCAGGCACTGGAAACACTGCAGCGGCTGTTGCCGGTG
CTGTGCCAGGACCATGGCCTGACCCCGGACCAAGTGGTGGCCATCGCCAACAATAACGGCGGCAAGCAGG
CACTAGAAACGGTGCAGCGGCTGTTGCCGGTGCTGTGCCAGGACCATGGCCTGACCCCGGACCAAGTGGT
GGCCATCGCCAACAATAACGGCGGCAAGCAGGCTCTTGAAACGGTGCAGCGGCTGTTGCCGGTGCTGTGC
CAGGACCATGGCCTGACCCCGGACCAGGTGGTGGCCATCGCCAGCAATATTGGCGGCAAGCAGGCGTTGG
AAACGGTGCAGCGGCTGTTGCCGGTGCTGTGCCAGGACCATGGCCTGACCCCGGACCAAGTGGTGGCCAT
CGCCAACAATAACGGCGGCAAGCAGGCGCTCGAAACGGTGCAGCGGCTGTTGCCGGTGCTGTGCCAGGAC
CATGGCCTGACCCCGGACCAGGTCGTGGCCATCGCCAGCAATATTGGCGGCAAGCAGGCAGTTGAAACGG
TGCAGCGGCTGTTGCCGGTGCTGTGCCAGGACCATGGCCTGACCCCGGACCAAGTCGTGGCCATCGCCAG
CCACGATGGCGGCAAGCAGGCTGTAGAAACGGTGCAGCGGCTGTTGCCGGTGCTGTGCCAGGACCATGGC
CTGACCCCGGACCAAGTCGTGGCCATCGCCAGCCACGATGGCGGCAAGCAGGCCGTGGAAACGGTGCAGC
GGCTGTTGCCGGTGCTGTGCCAGGACCATGGCCTGACCCCGGACCAGGTGGTGGCCATCGCCAGCCACGA
TGGCGGCAAGCAGGCGCTGGAAACTGTACAGCGGCTGTTGCCGGTGCTGTGCCAGGCCCATGGCCTGACC
CCGGACCAAGTGGTGGCCATCGCCAGCAATGGCGGCGGCAAGCAGGCACTAGAAACGGTGCAGCGGCTGT
TGCCGGTGCTGTGCCAGGACCATGGCCTGACCCCGGACCAGGTGGTGGCCATCGCCAGCCACGATGGCGG
CAAGCAGGCTCTTGAAACGGTGCAGCGGCTGTTGCCGGTGCTGTGCCAGGACCATGGCCTGACCCCGGAC
CAAGTCGTGGCCATCGCCAGCCACGATGGCGGCAAGCAGGCGTTGGAAACGGTGCAGCGGCTGTTGCCGG
TGCTGTGCCAGGACCATGGCCTGACCCCGGACCAGGTCGTGGCCATCGCCAGCAATATTGGCGGCAAGCA
GGCGCTCGAAACGGTGCAGCGGCTGTTGCCGGTGCTGTGCCAGGACCATGGCCTGACCCCGGACCAAGTC
GTGGCCATCGCCAGCCACGATGGCGGCAAGCAGGCAGTTGAAACGGTGCAGCGGCTGTTGCCGGTGCTGT
GCCAGGCCCATGGCCTGACCCCGGCCCAAGTGGTGGCCATCGCCAGCAATGGCGGCGGCAAGCAGGCTGT
AGAAACGGTGCAGCGGCTGTTGCCGGTGCTGTGCCAGGACCATGGCCTGACCCCGAACCAGGTGGTGGCC
ATCGCCAGCAATGGCGGCAAGCAGGCGCTGGAGAGCATTGTTGCCCAGTTATCTCGCCCTGATCCGGCGT
TGGCCGCGTTGACCAACGACCACCTCGTCGCCTTGGCCTGCCTCGGCGGACGTCCTGCCCTGGATGCAGT
GAAAAAGGGATTGCCGCACGCGCCGGAATTGATCAGAAGAATCAATCGCCGCATTCCCGAACGCACGTCC
CATCGCGTTCCCGACCTCGCGCACGTGGTTCGCGTGCTTGGTTTTTCCAGAGCCACTCCCACCCAGCGC
AAGCATTCGATGACGCCATGACGCAGTTCGAGATGAGCAGGCACGGCTTGGTACAGCTCTTTCGCAGAGT
GGGCGTCACCGAATTCGAAGCCCGCTACGGAACGCTCCCCCCAGCCTCGCAGCGTTGGGACCGTATCCTC
CAGGCATCAGGGATGAAAAGGGCCAAACCGTCCCCTACTTCAGCTCAAACACCGGATCAGGCGTCTTTAC

FIG. 9C-1

ATGCAGATTACAAGGACGACGACGACAAGAAGGATTACAAGGACGACGACGACAAGAAGGGTCGACCCAG
CCCAATGCACGAGGGAGATCAGACGCGGGCAAGCAGCCGTAAACGGTCCCGATCGGATCGTGCTGTCACC
GGCCCCTCCACACAGCAATCTTTCGAGGTGCGCGTTCCCGAACAGCAAGATGCGCTGCATTTGCCCCTCA
GCTGGAGGGTAAAACGCCCGCGTACCAGGATCGGGGGCGGCCTCCCGGATCCTGGTACGCCCATCGCTGC
CGACCTGGCAGCGTCCAGCACCGTGATGTGGGAACAAGATGCGGCCCCCTTCGCAGGGGCAGCGGATGAT
TTCCCGGCATTCAACGAAGAGGAGCTCGCATGGTTGATGGAGCTATTGCCTCAGTCAGGCTCAGTCGGAG
GGACGATCTCTAGACAGCTAGTGAAATCTGAATTGGAAGAGAAGAAATCTGAACTTAGACATAAATTGAA
ATATGTGCCACATGAATATATTGAATTGATTGAAATCGCAAGAAATTCAACTCAGGATAGAATCCTTGAA
ATGAAGGTGATGGAGTTCTTTATGAAGGTTTATGGTTATCGTGGTAAACATTTGGGTGGATCAAGGAAAC
CAGACGGAGCAATTTATACTGTCGGATCTCCTATTGATTACGGTGTGATCGTTGATACTAAGGCATATTC
AGGAGGTTATAATCTTCCAATTGGTCAAGCAGATGAAATGCAAAGATATGTCGAAGAGAATCAAACAAGA
AACAAGCATATCAACCCTAATGAATGGTGGAAAGTCTATCCATCTTCAGTAACAGAATTTAAGTTCTTGT
TTGTGAGTGGTCATTTCAAAGGAAACTACAAAGCTCAGCTTACAAGATTGAATCATATCACTAATTGTAA
TGGAGCTGTTCTTAGTGTAGAAGAGCTTTTGATTGGTGGAGAAATGATTAAAGCTGGTACATTGACACTT
GAGGAAGTGAGAAGGAAATTTAATAACGGTGAGATAAACTTTTAATAGACTAGT

*FIG. 9C-2*

TALEN-R Protein (SEQ ID NO: 39)
MDPIRSRTPSPARELLPGPQPDRVQPTADRGGAPPAGGPLDGLPARRTMSRTRLPSPPAPSPAFSAGSFS
DLLRQFDPSLLDTSLLDSMPAVGTPHTAAAPAEWDEVQSGLRAADDPPPTVRVAVTAARPPRAKPAPRRR
AAQPSDASPAAQVDLRTLGYSQQQQEKIKPKVRSTVAQHHEALVGHGFTHAHIVALSQHPAALGTVAVKY
QHIITALPEATHEDIVGVGKQWSGARALEALLTKAGELRGPPLQLDTGQLLKIAKRGGVTAVEAVHAWRN
ALTGAPLNLTPDQVVAIASNIGGKQALETVQRLLPVLCQAHGLTPAQVVAIASNGGGKQALETVQRLLPV
LCQDHGLTPDQVVAIASNIGGKQALETVQRLLPVLCQAHGLTPAQVVAIASNGGGKQALETVQRLLPVLC
QDHGLTPDQVVAIASNIGGKQAVETVQRLLPVLCQDHGLTPDQVVAIANNNGGKQAVETVQRLLPVLCQA
HGLTPAQVVAIASNGGGKQAVETVQRLLPVLCQAHGLTPDQVVAIASNGGGKQALETLQRLLPVLCQDHG
LTPDQVVAIANNNGGKQALETVQRLLPVLCQDHGLTPDQVVAIANNNGGKQALETVQRLLPVLCQDHGLT
PDQVVAIASNIGGKQALETVQRLLPVLCQDHGLTPDQVVAIANNNGGKQALETVQRLLPVLCQDHGLTPD
QVVAIASNIGGKQAVETVQRLLPVLCQDHGLTPDQVVAIASHDGGKQAVETVQRLLPVLCQDHGLTPDQV
VAIASHDGGKQAVETVQRLLPVLCQDHGLTPDQVVAIASHDGGKQALETVQRLLPVLCQAHGLTPDQVVA
IASNGGGKQALETVQRLLPVLCQDHGLTPDQVVAIASHDGGKQALETVQRLLPVLCQDHGLTPDQVVAIA
SHDGGKQALETVQRLLPVLCQDHGLTPDQVVAIASNIGGKQALETVQRLLPVLCQDHGLTPDQVVAIASH
DGGKQAVETVQRLLPVLCQAHGLTPAQVVAIASNGGGKQAVETVQRLLPVLCQDHGLTPNQVVAIASNGG
KQALESIVAQLSRPDPALAALTNDHLVALACLGGRPALDAVKKGLPHAPELIRRINRRIPERTSHRVPDL
AHVVRVLGFFQSHSHPAQAFDDAMTQFEMSRHGLVQLFRRVGVTEFEARYGTLPPASQRWDRILQASGMK
RAKPSPTSAQTPDQASLHADYKDDDDKKDYKDDDDKKGRPSPMHEGDQTRASSRKRSRSDRAVTGPSTQQ
SFEVRVPEQQDALHLPLSWRVKRPRTRIGGGLPDPGTPIAADLAASSTVMWEQDAAPFAGAADDFPAFNE
EELAWLMELLPQSGSVGGTISRQLVKSELEEKKSELRHKLKYVPHEYIELIEIARNSTQDRILEMKVMEF
FMKVYGYRGKHLGGSRKPDGAIYTVGSPIDYGVIVDTKAYSGGYNLPIGQADEMQRYVEENQTRNKHINP
NEWWKVYPSSVTEFKFLFVSGHFKGNYKAQLTRLNHITNCNGAVLSVEELLIGGEMIKAGTLTLEEVRRK
FNNGEINF*

*FIG. 9D*

SEQUENCE LISTING

```
<160> NUMBER OF SEQ ID NOS: 52

<210> SEQ ID NO 1
<211> LENGTH: 63
<212> TYPE: DNA
<213> ORGANISM: Xanthomonas oryzae

<400> SEQUENCE: 1

cttccttcct agcactatat aaaccccctc caaccaggtg ctaagctcat caagccttca      60

agc                                                                   63


<210> SEQ ID NO 2
<211> LENGTH: 24
<212> TYPE: DNA
<213> ORGANISM: Xanthomonas oryzae

<400> SEQUENCE: 2

gctaagctca tcaagccttc aagc                                            24


<210> SEQ ID NO 3
<211> LENGTH: 59
<212> TYPE: DNA
<213> ORGANISM: Xanthomonas oryzae
```

<400> SEQUENCE: 3
cttccttcct agcactatat aaaccccctc aaagtgctaa gctcatcaag ccttcaagc 59

<210> SEQ ID NO 4
<211> LENGTH: 31
<212> TYPE: DNA
<213> ORGANISM: Xanthomonas oryzae

<400> SEQUENCE: 4
cttccttcct aagctcatca agccttcaag c 31

<210> SEQ ID NO 5
<211> LENGTH: 45
<212> TYPE: DNA
<213> ORGANISM: Xanthomonas oryzae

<400> SEQUENCE: 5
cttccttcct agcactatat aaaccccctc atcaagcctt caagc 45

<210> SEQ ID NO 6
<211> LENGTH: 54
<212> TYPE: DNA
<213> ORGANISM: Xanthomonas oryzae

<400> SEQUENCE: 6
cttccttcct agcactatat aaacccaggt gctaagctca tcaagccttc aagc 54

<210> SEQ ID NO 7
<211> LENGTH: 59
<212> TYPE: DNA
<213> ORGANISM: Xanthomonas oryzae

<400> SEQUENCE: 7
cttccttcct agcactatat aaaccccctc caagtgctaa gctcatcaag ccttcaagc 59

<210> SEQ ID NO 8
<211> LENGTH: 60
<212> TYPE: DNA
<213> ORGANISM: Xanthomonas oryzae

<400> SEQUENCE: 8
cttccttcct agcactatat aaaccccctc ccaggtgcta agctcatcaa gccttcaagc 60

<210> SEQ ID NO 9
<211> LENGTH: 72
<212> TYPE: DNA
<213> ORGANISM: Xanthomonas oryzae

<400> SEQUENCE: 9
cttccttcct agcactatat aaaccccctc caaccaggtt tatatagtgc taagctcatc 60
aagccttcaa gc 72

<210> SEQ ID NO 10
<211> LENGTH: 27
<212> TYPE: DNA
<213> ORGANISM: Xanthomonas oryzae

<400> SEQUENCE: 10
ataaaccccc tccaaccagg tgctaag 27

<210> SEQ ID NO 11
<211> LENGTH: 51

-continued

<212> TYPE: DNA
<213> ORGANISM: Xanthomonas oryzae

<400> SEQUENCE: 11
ataaaccccc tccaaccagg tgctaagcaa agcaaactca agtagtagct g 51

<210> SEQ ID NO 12
<211> LENGTH: 62
<212> TYPE: DNA
<213> ORGANISM: Xanthomonas oryzae

<400> SEQUENCE: 12
ataaaccccc tccaaccagg tgctaagctc atctcaagca aagcaaactc aagtagtagc 60
tg 62

<210> SEQ ID NO 13
<211> LENGTH: 63
<212> TYPE: DNA
<213> ORGANISM: Xanthomonas oryzae

<400> SEQUENCE: 13
ataaaccccc tccaaccagg tgctaagctc accttcaagc aaagcaaact caagtagtag 60
ctg 63

<210> SEQ ID NO 14
<211> LENGTH: 64
<212> TYPE: DNA
<213> ORGANISM: Xanthomonas oryzae

<400> SEQUENCE: 14
ataaaccccc tccaaccagg tgctaagctc atcaagcctt caaagcaaac tcaagtagta 60
gctg 64

<210> SEQ ID NO 15
<211> LENGTH: 70
<212> TYPE: DNA
<213> ORGANISM: Xanthomonas oryzae

<400> SEQUENCE: 15
ataaaccccc tccaaccagg tgctaagctc atcaagcaac ttcaagcaaa gcaaactcaa 60
gtagtagctg 70

<210> SEQ ID NO 16
<211> LENGTH: 26
<212> TYPE: DNA
<213> ORGANISM: Xanthomonas oryzae

<400> SEQUENCE: 16
ataaaccccc tccaaccagg tgctaa 26

<210> SEQ ID NO 17
<211> LENGTH: 29
<212> TYPE: DNA
<213> ORGANISM: Xanthomonas oryzae

<400> SEQUENCE: 17
atataaaccc cctccaacca ggtgctaag 29

<210> SEQ ID NO 18
<211> LENGTH: 23
<212> TYPE: DNA

<213> ORGANISM: Xanthomonas oryzae

<400> SEQUENCE: 18
tataaaagca ccacaactcc ctt 23

<210> SEQ ID NO 19
<211> LENGTH: 27
<212> TYPE: DNA
<213> ORGANISM: Xanthomonas oryzae

<400> SEQUENCE: 19
gcatctcccc ctactgtaca ccaccaa 27

<210> SEQ ID NO 20
<211> LENGTH: 26
<212> TYPE: DNA
<213> ORGANISM: Xanthomonas oryzae

<400> SEQUENCE: 20
ataaaccccc tccaaccagg tgctaa 26

<210> SEQ ID NO 21
<211> LENGTH: 4548
<212> TYPE: DNA
<213> ORGANISM: Xanthomonas oryzae

<400> SEQUENCE: 21
atggatccca ttcgttcgcg cacgccaagt cctgcccgcg agcttctgcc cggaccccaa 60
ccggataggg ttcagccgac tgcagatcgg gggggggctc cgcctgctgg cggccccctg 120
gatggcttgc ccgctcggcg gacgatgtcc cggacccggc tgccatctcc ccctgcgccc 180
tcgcctgcgt tctcggcggg cagcttcagc gatctgctcc gtcagttcga tccgtcgctt 240
cttgatacat cgcttcttga ttcgatgcct gccgtcggca cgccgcatac agcggctgcc 300
ccagcagagt gggatgaggt gcaatcgggt ctgcgtgcag ccgatgaccc gccacccacc 360
gtgcgtgtcg ctgtcactgc cgcgcggccg ccgcgcgcca agccggcccc gcgacggcgt 420
gcggcgcaac cctccgacgc ttcgccggcc gcgcaggtgg atctacgcac gctcggctac 480
agtcagcagc agcaagagaa gatcaaaccg aaggtgcgtt cgacagtggc gcagcaccac 540
gaggcactgg tgggccatgg gtttacacac gcgcacatcg ttgcgctcag ccaacacccg 600
gcagcgttag ggaccgtcgc tgtcaagtat cagcacataa tcacggcgtt gccagaggcg 660
acacacgaag acatcgttgg cgtcggcaaa cagtggtccg gcgcacgcgc cctggaggcc 720
ttgctcacga aggcggggga gttgagaggt ccgccgttac agttggacac aggccaactt 780
ctcaagattg caaaacgtgg cggcgtgacc gcagtggagg cagtgcatgc atcgcgcaat 840
gcactgacgg gtgcccccct gaacctgacc ccggcacagg tggtggccat cgccaacaat 900
aacggcggca agcaggcgct ggagacggtg cagcggctgt tgccggtgct gtgccaggac 960
catggcctga cccaggacca ggtggtggcc atcgccagcc acgatggcgg caagcaggcc 1020
ttggagacgg tgcagcggct gttgccggtg ctgtgccagg cccatggcct gaccccggcc 1080
caagtggtgg ccatcgccag caatggcggc ggcaagcagg ctctggagac ggtacagcgg 1140
ctgttgccgg tgctgtgcca ggaccatggc ctgaccccgg accaggtcgt ggccatcgcc 1200
agcaatggcg gcggcaagca ggcgttggag acggtacagc ggctgttgcc ggtgctgtgc 1260
caggaccatg gcctgacccc ggaccaggtg gtggccatcg ccaacaataa cggcggcaag 1320
caggctttgg agacggtaca gcggctgttg ccggtgctgt gccaggacca tggcctgacc 1380

-continued

```
ccggaccagg tggtggccat cgccagcaat attggcggca agcaggcatt ggagacggta   1440
cagcggctgt tgccggtgct gtgccaggac catggcctga ccccggacca ggtcgtggcc   1500
atcgccagca atattggcgg caagcaggcc ctggagacgg tacagcggct gttgccggtg   1560
ctgtgccagg accatggcct gaccccggac caggtcgtgg ccatcgccaa caataacggc   1620
ggcaagcagg cactggaaac actgcagcgg ctgttgccgg tgctgtgcca ggaccatggc   1680
ctgaccccgg accaggtcgt ggccatcgcc aacaataacg gcggcaagca ggccttggag   1740
acggtgcagc ggctgttgcc ggtgctgtgc caggaccatg gcctgacccc ggaccaagtc   1800
gtggccatcg ccagccacga tggcggcaag caggctctgg agacggtaca gcggctgttg   1860
ccggtgctgt gccaggacca tggcctgacc ccggaccagg tcgtggccat cgccagcaat   1920
ggcggcggca agcaggcgtt ggagacggta cagcggctgt tgccggtgct gtgccaggac   1980
catggcctga ccccggacca ggtcgtggcc atcgccagca atggcggcgg caagcaggct   2040
ttggagacgg tacagcggct gttgccggtg ctgtgccagg accatggcct gaccccggac   2100
caggtggtgg ccatcgccaa caataacggc ggcaagcagg cattggagac ggtacagcgg   2160
ctgttgccgg tgctgtgcca ggaccatggc ctgaccccgg accaggtcgt ggccatcgcc   2220
agcaatattg gcggcaagca ggccctggag acggtacagc ggctgttgcc ggtgctgtgc   2280
caggaccatg gcctgacccc ggaccaggtc gtggccatcg ccagcaatgg cggcggcaag   2340
caggcactgg agactgtaca gcggctgttg ccggtgctgt gccaggacca tggcctgacc   2400
ccggaccagg tcgtggccat cgccaacaat aacggcggca agcaggcctt ggagacggtg   2460
cagcggctgt tgccggtgct gtgccaggac catggcctga ccccggacca ggtggtggcc   2520
atcgccagca atattggcgg caagcaggct ctggagacgg tacagcggct gttgccggtg   2580
ctgtgccagg accatggcct gaccccggac caggtggtgg ccatcgccaa caataacggc   2640
ggcaagcagg cgttggagac ggtacagcgg ctgttgccgg tgctgtgcca ggaccatggc   2700
ctgacccagg accaggtggt ggccatcgcc agccacgatg gcggcaagca ggctttggag   2760
acggtacagc ggctgttgcc ggtgctgtgc caggaccatg gcctgacccc ggaccaggtc   2820
gtggccaccg ccagcaatgg cggcggcaag caggcattgg agacggtaca gcggctgttg   2880
ccggtgctgt gccaggacca tggcctgacc ccggaccagg tcgtggccat cgccagcaat   2940
ggcggcggca agcaggccct ggagacggta cagcggctgt tgccggtgct gtgccaggac   3000
catggcctga ccccggacca ggtcgtggcc atcgccagca atattggcgg caagcaggca   3060
ctggagacga ttgttgccca gttatctcgc cctgatccgg cgttggccgc gttgaccaac   3120
gaccacctcg tcgccttggc ctgcctcggc ggacgtcctg ccctggatgc agtgaaaaag   3180
ggattgccgc acgcgccgga attgatcaga agaatcaatc gccgcattcc cgaacgcacg   3240
tcccatcgcg ttcccgacct cgcgcacgtg gttcgcgtgc ttggtttttt ccagagccac   3300
tcccacccag cgcaagcatt cgatgacgcc atgacgcagt tcgagatgag caggcacggc   3360
ttggtacagc tctttcgcag agtgggcgtc accgaattcg aagcccgcta cggaacgctc   3420
cccccagcct cgcagcgttg ggaccgtatc ctccaggcat cagggatgaa aagggccaaa   3480
ccgtccccta cttcagctca aacaccggat caggcgtctt tgcatgcaga ttacaaggac   3540
gacgacgaca agaaggatta caaggacgac gacgacaaga agggtcgacc cagcccaatg   3600
cacgagggag atcagacgcg ggcaagcagc cgtaaacggt cccgatcgga tcgtgctgtc   3660
accggcccct ccacacagca atctttcgag gtgcgcgttc ccgaacagca agatgcgctg   3720
```

-continued

```
catttgcccc tcagctggag ggtaaaacgc ccgcgtacca ggatcggggg cggcctcccg   3780
gatcctggta cgcccatcgc tgccgacctg gcagcgtcca gcaccgtgat gtgggaacaa   3840
gatgcggccc ccttcgcagg ggcagcggat gatttcccgg cattcaacga agaggagctc   3900
gcatggttga tggagctatt gcctcagtca ggctcagtcg gagggacgat ctctagacag   3960
ctagtgaaat ctgaattgga agagaagaaa tctgaactta gacataaatt gaaatatgtg   4020
ccacatgaat atattgaatt gattgaaatc gcaagaaatt caactcagga tagaatcctt   4080
gaaatgaagg tgatggagtt ctttatgaag gtttatggtt atcgtggtaa acatttgggt   4140
ggatcaagga aaccagacgg agcaatttat actgtcggat ctcctattga ttacggtgtg   4200
atcgttgata ctaaggcata ttcaggaggt tataatcttc caattggtca agcagatgaa   4260
atgcaaagat atgtcgaaga gaatcaaaca agaaacaagc atatcaaccc taatgaatgg   4320
tggaaagtct atccatcttc agtaacagaa tttaagttct tgtttgtgag tggtcatttc   4380
aaaggaaact acaaagctca gcttacaaga ttgaatcata tcactaattg taatggagct   4440
gttcttagtg tagaagagct tttgattggt ggagaaatga ttaaagctgg tacattgaca   4500
cttgaggaag tgagaaggaa atttaataac ggcgagataa acttttaa                4548
```

<210> SEQ ID NO 22
<211> LENGTH: 4647
<212> TYPE: DNA
<213> ORGANISM: Xanthomonas oryzae

<400> SEQUENCE: 22

```
atggatccca ttcgttcgcg cacgccaagt cctgcccgcg agcttctgcc cggaccccaa     60
ccggataggg ttcagccgac tgcagatcgg ggggggctc cgcctgctgg cggccccctg    120
gatggcttgc ccgctcggcg gacgatgtcc cggacccggc tgccatctcc ccctgcgccc    180
tcgcctgcgt tctcggcggg cagcttcagc gatctgctcc gtcagttcga tccgtcgctt    240
cttgatacat cgcttcttga ttcgatgcct gccgtcggca cgccgcatac agcggctgcc    300
ccagcagagt gggatgaggt gcaatcgggt ctgcgtgcag ccgatgaccc gccacccacc    360
gtgcgtgtcg ctgtcactgc cgcgcggccg ccgcgcgcca agccggcccc gcgacggcgt    420
gcggcgcaac cctccgacgc ttcgccggcc gcgcaggtgg atctacgcac gctcggctac    480
agtcagcagc agcaagagaa gatcaaaccg aaggtgcgtt cgacagtggc gcagcaccac    540
gaggcactgg tgggccatgg gtttacacac gcgcacatcg ttgcgctcag ccaacacccg    600
gcagcgttag ggaccgtcgc tgtcaagtat cagcacataa tcacggcgtt gccagaggcg    660
acacacgaag acatcgttgg cgtcggcaaa cagtggtccg gcgcacgcgc cctggaggcc    720
ttgctcacga aggcggggga gttgagaggt ccgccgttac agttggacac aggccaactt    780
ctcaagattg caaaacgtgg cggcgtgacc gcagtggagg cagtgcatgc atggcgcaat    840
gcactgacgg gtgcccccct gaacctgacc ccggcacagg tggtggccat cgccagccac    900
gatggcggca agcaggcgct ggagacggtg cagcggctgt tgccggtgct gtgccaggac    960
catggcctga ccccggacca ggtggtggcc atcgccagca atattggcgg caagcaggcc   1020
ttggagacgg tgcagcggct gttgccggtg ctgtgccagg accatggcct gaccccggac   1080
caagtggtgg ccatcgccaa caataacggc ggcaagcagg ctctggagac ggtacagcgg   1140
ctgttgccgg tgctgtgcca ggaccatggc ctgaccccgg accaggtggt ggccatcgcc   1200
agccacgatg gcggcaagca ggcgttggag acggtacagc ggctgttgcc ggtgctgtgc   1260
caggaccatg gcctgacccc ggaccaggtc gtggccatcg ccagcaatgg cggcggcaag   1320
```

-continued

```
caggctttgg agacggtaca gcggctgttg ccggtgctgt gccaggacca tggcctgacc   1380
ccggaccagg tcgtggccat cgccagcaat attggcggca agcaggcatt ggagacggta   1440
cagcggctgt tgccggtgct gtgccaggac catggcctga ccccggacca ggtggtggcc   1500
atcgccagcc acgatggcgg caagcaggcc ctggagacgg tacagcggct gttgccggtg   1560
ctgtgccagg accatggcct gaccccggac caggtcgtgg ccatcgccag caatggcggc   1620
ggcaagcagg cactggaaac actgcagcgg ctgttgccgg tgctgtgcca ggaccatggc   1680
ctgaccccgg accaggtggt ggccatcgcc agcaatattg gcggcaagca ggccttggag   1740
acggtgcagc ggctgttgcc ggtgctgtgc caggaccatg gcctgacccc ggaccaagtc   1800
gtggccatcg ccagccacga tggcggcaag caggctctgg agacggtaca gcggctgttg   1860
ccggtgctgt gccaggacca tggcctgacc ccggaccagg tcgtggccat cgccagcaat   1920
ggcggcggca agcaggcgtt ggagacggta cagcggctgt tgccggtgct gtgccaggac   1980
catggcctga ccccggacca ggtcgtggcc atcgccagca atggcggcgg caagcaggct   2040
ttggagacgg tacagcggct gttgccggtg ctgtgccagg accatggcct gaccccggac   2100
caggtggtgg ccatcgccaa caataacggc ggcaagcagg cattggagac ggtacagcgg   2160
ctgttgccgg tgctgtgcca ggaccatggc ctgaccccgg accaggtggt ggccatcgcc   2220
agcaatattg gcggcaagca ggccctggag acggtacagc ggctgttgcc ggtgctgtgc   2280
caggaccatg gcctgacccc ggaccaggtc gtggccatcg ccaacaataa cggcggcaag   2340
caggcactgg agactgtaca gcggctgttg ccggtgctgt gccaggacca tggcctgacc   2400
ccggaccagg tcgtggccat cgccagcaat ggcggcggca agcaggcctt ggagacggtg   2460
cagcggctgt tgccggtgct gtgccaggcc catggcctga ccccggccca agtggtggcc   2520
atcgccagca atggcggcgg caagcaggct ctggagacgg tacagcggct gttgccggtg   2580
ctgtgccagg accatggcct gaccccggac caggtcgtgg ccatcgccag caatggcggc   2640
ggcaagcagg cgttggagac ggtacagcgg ctgttgccgg tgctgtgcca ggaccatggc   2700
ctgaccccgg accaggtcgt ggccatcgcc aacaataacg gcggcaagca ggctttggag   2760
acggtacagc ggctgttgcc ggtgctgtgc caggaccatg gcctgacccc ggaccaggtg   2820
gtggccatcg ccagccacga tggcggcaag caggcattgg agacggtaca gcggctgttg   2880
ccggtgctgt gccaggacca tggcctgacc ccggaccagg tcgtggccat cgccagcaat   2940
ggcggcggca agcaggccct ggagacggta cagcggctgt tgccggtgct gtgccaggac   3000
catggcctga ccccggacca ggtcgtggcc atcgccagca atggcggcgg caagcaggca   3060
ctggagacgg tacagcggct gttgccggtg ctgtgccagg accatggcct gaccccgaac   3120
caggtggtgg ccatcgccag caatggcggc aagcaggcgc tggagagcat tgttgcccag   3180
ttatctcgcc ctgatccggc gttggccgcg ttgaccaacg accacctcgt cgccttggcc   3240
tgcctcggcg gacgtcctgc cctggatgca gtgaaaaagg gattgccgca cgcgccggaa   3300
ttgatcagaa gaatcaatcg ccgcattccc gaacgcacgt cccatcgcgt tcccgacctc   3360
gcgcacgtgg ttcgcgtgct tggtttttttc cagagccact cccacccagc gcaagcattc   3420
gatgacgcca tgacgcagtt cgagatgagc aggcacggct tggtacagct ctttcgcaga   3480
gtgggcgtca ccgaattcga agcccgctac ggaacgctcc ccccagcctc gcagcgttgg   3540
gaccgtatcc tccaggcatc agggatgaaa agggccaaac cgtcccctac ttcagctcaa   3600
acaccggatc aggcgtcttt gcatgcagat tacaaggacg acgacgacaa gaaggattac   3660
```

-continued aggaggacgacg acgacaagaa gggtcgaccc agcccaatgc acgagggaga tcagacgcgg 3720
gcaagcagcc gtaaacggtc ccgatcggat cgtgctgtca ccggcccctc cacacagcaa 3780
tctttcgagg tgcgcgttcc cgaacagcaa gatgcgctgc atttgcccct cagctggagg 3840
gtaaaacgcc cgcgtaccag gatcgggggc ggcctcccgg atcctggtac gcccatcgct 3900
gccgacctgg cagcgtccag caccgtgatg tgggaacaag atgcggcccc cttcgcaggg 3960
gcagcggatg atttcccggc attcaacgaa gaggagctcg catggttgat ggagctattg 4020
cctcagtcag gctcagtcgg agggacgatc tctagacagc tagtgaaatc tgaattggaa 4080
gagaagaaat ctgaacttag acataaattg aaatatgtgc cacatgaata tattgaattg 4140
attgaaatcg caagaaattc aactcaggat agaatccttg aaatgaaggt gatggagttc 4200
tttatgaagg tttatggtta tcgtggtaaa catttgggtg gatcaaggaa accagacgga 4260
gcaatttata ctgtcggatc tcctattgat tacggtgtga tcgttgatac taaggcatat 4320
tcaggaggtt ataatcttcc aattggtcaa gcagatgaaa tgcaaagata tgtcgaagag 4380
aatcaaacaa gaaacaagca tatcaaccct aatgaatggt ggaaagtcta tccatcttca 4440
gtaacagaat ttaagttctt gtttgtgagt ggtcatttca aaggaaacta caaagctcag 4500
cttacaagat tgaatcatat cactaattgt aatggagctg ttcttagtgt agaagagctt 4560
ttgattggtg gagaaatgat taaagctggt acattgacac ttgaggaagt gagaaggaaa 4620
tttaataacg gcgagataaa cttttaa 4647

<210> SEQ ID NO 23
<211> LENGTH: 4428
<212> TYPE: DNA
<213> ORGANISM: Xanthomonas oryzae

<400> SEQUENCE: 23
atggatccca ttcgttcgcg cacgccaagt cctgcccgcg agcttctgcc cggaccccaa 60
ccggataggg ttcagccgac tgcagatcgg gggggggctc cgcctgctgg cggccccctg 120
gatggcttgc ccgctcggcg gacgatgtcc cggacccggc tgccatctcc ccctgcgccc 180
tcgcctgcgt tctcggcggg cagcttcagc gatctgctcc gtcagttcga tccgtcgctt 240
cttgatacat cgcttcttga ttcgatgcct gccgtcggca cgccgcatac agcggctgcc 300
ccagcagagt gggatgaggt gcaatcgggt ctgcgtgcag ccgatgaccc gccacccacc 360
gtgcgtgtcg ctgtcactgc cgcgcggccg ccgcgcgcca agccggcccc gcgacggcgt 420
gcggcgcaac cctccgacgc ttcgccggcc gcgcaggtgg atctacgcac gctcggctac 480
agtcagcagc agcaagagaa gatcaaaccg aaggtgcgtt cgacagtggc gcagcaccac 540
gaggcactgg tgggccatgg gtttacacac gcgcacatcg ttgcgctcag ccaacacccg 600
gcagcgttag ggaccgtcgc tgtcaagtat cagcacataa tcacggcgtt gccagaggcg 660
acacacgaag acatcgttgg cgtcggcaaa cagtggtccg gcgcacgcgc cctggaggcc 720
ttgctcacga aggcgggggga gttgagaggt ccgccgttac agttggacac aggccaactt 780
ctcaagattg caaaacgtgg cggcgtgacc gcagtggagg cagtgcatgc atcgcgcaat 840
gcactgacgg gtgccccccct gaacctgacc ccggcacagg tggtggccat cgccagccac 900
gatggcggca agcaggcgct ggagacggtg cagcggctgt tgccggtgct gtgccaggac 960
catggcctga ccccggacca ggtcgtggcc atcgccagca atggcggcgg caagcaggcc 1020
ttggagacgg tgcagcggct gttgccggtg ctgtgccagg cccatggcct gaccccggcc 1080
caagtggtgg ccatcgccag caatggcggc ggcaagcagg ctctggagac ggtacagcgg 1140

-continued

```
ctgttgccgg tgctgtgcca ggaccatggc ctgacccagg accaggtggt ggccatcgcc   1200
agccacgatg gcggcaagca ggcgttggag acggtacagc ggctgttgcc ggtgctgtgc   1260
caggaccatg gcctgacccc ggaccaggtg gtggccatcg ccagccacga tggcggcaag   1320
caggctttgg agacggtaca gcggctgttg ccggtgctgt gccaggacca tggcctgacc   1380
ccggaccagg tcgtggccat cgccagcaat ggcggcggca agcaggcatt ggagacggta   1440
cagcggctgt tgccggtgct gtgccaggac catggcctga ccccggacca ggtcgtggcc   1500
atcgccagca atggcggcgg caagcaggcc ctggagacgg tacagcggct gttgccggtg   1560
ctgtgccagg accatggcct gacccaggac caggtggtgg ccatcgccag ccacgatggc   1620
ggcaagcagg cactggaaac actgcagcgg ctgttgccgg tgctgtgcca ggaccatggc   1680
ctgaccccgg accaggtggt ggccatcgcc agccacgatg gcggcaagca ggccttggag   1740
acggtgcagc ggctgttgcc ggtgctgtgc caggcccatg gcctgacccc ggcccaagtg   1800
gtggccatcg ccagcaatgg cggcggcaag caggctctgg agacggtaca gcggctgttg   1860
ccggtgctgt gccaggacca tggcctgacc ccggaccagg tcgtggccat cgccagcaat   1920
attggcggca agcaggcgtt ggagacggta cagcggctgt tgccggtgct gtgccaggac   1980
catggcctga ccccggacca ggtcgtggcc atcgccaaca ataacggcgg caagcaggct   2040
ttggagacgg tacagcggct gttgccggtg ctgtgccagg gccatggcct gacccaggac   2100
caggtggtgg ccatcgccag ccacgatggc ggcaagcagg cattggagac ggtacagcgg   2160
ctgttgccgg tgctgtgcca ggaccatggc ctgaccccgg accaggtggt ggccatcgcc   2220
agcaatattg gcggcaagca ggccctggag acggtacagc ggctgttgcc ggtgctgtgc   2280
caggaccatg gcctgacccc ggaccaggtg gtggccatcg ccagccacga tggcggcaag   2340
caggcactgg agactgtaca gcggctgttg ccggtgctgt gccaggacca tggcctgacc   2400
ccggaccagg tcgtggccat cgccagcaat ggcggcggca agcaggcctt ggagacggtg   2460
cagcggctgt tgccggtgct gtgccaggac catggcctga ccccggacca ggtggtggcc   2520
atcgccagca atattggcgg caagcaggct ctggagacgg tacagcggct gttgccggtg   2580
ctgtgccagg accatggcct gaccccggac caggtcgtgg ccatcgccag caatggcggc   2640
ggcaagcagg cgttggagac ggtacagcgg ctgttgccgg tgctgtgcca ggaccatggc   2700
ctgaccccgg accaggtggt ggccatcgcc agcaatattg gcggcaagca ggctttggag   2760
acggtacagc ggctgttgcc ggtgctgtgc caggaccatg gcctgacccc ggaccaggtc   2820
gtggccatcg ccagcaatgg cggcggcaag caggcattgg agacggtaca gcggctgttg   2880
ccggtgctgt gccaggacca tggcctgacc ccggaccagg tggtggccat cgccagcaat   2940
attggcggca agcaggccct ggagacggta cagcggctgt tgccggtgct gtgccaggac   3000
catggcctga ccccggacca ggtggtggcc atcgccagca atattggcgg caagcaggca   3060
ctggagacga ttgttgccca gttatctcgc cctgatccgg cgttggccgc gttgaccaac   3120
gaccacctcg tcgccttggc ctgcctcggc ggacgtcctg ccctggatgc agtgaaaaag   3180
ggattgccgc acgcgccgga attgatcaga agaatcaatc gccgcattcc cgaacgcacg   3240
tcccatcgcg ttcccgacct cgcgcacgtg gttcgcgtgc ttggtttttt ccagagccac   3300
tcccacccag cgcaagcatt cgatgacgcc atgacgcagt tcgagatgag caggcacggc   3360
ttggtacagc tctttcgcag agtgggcgtc accgaattcg aagcccgcta cggaacgctc   3420
cccccagcct cgcagcgttg ggaccgtatc ctccaggcat cagggatgaa aagggccaaa   3480
```

-continued

```
ccgtccccta cttcagctca aacaccggat caggcgtctt tgcatgcaga ttacaaggac   3540

gacgacgaca agaaggatta caaggacgac gacgacaaga agggtcgacc cagcccaatg   3600

cacgagggag atcagacagg ggcaagcagc cgtaaacggt cccgatcgga tcgtgctgtc   3660

accggcccct ccgcacagca atctttcgag gtgcgcgttc ccgaacagcg cgatgcgctg   3720

catttgcccc tcagctggag ggtaaaacgc ccgcgtacca ggatcggggg cggcctcccg   3780

gatcctggta cgcccatcgc tgccgacctg gcagcgtcca gcaccgtgat cagatcccag   3840

ctagtgaaat ctgaattgga agagaagaaa tctgaactta gacataaatt gaaatatgtg   3900

ccacatgaat atattgaatt gattgaaatc gcaagaaatt caactcagga tagaatcctt   3960

gaaatgaagg tgatggagtt ctttatgaag gtttatggtt atcgtggtaa acatttgggt   4020

ggatcaagga aaccagacgg agcaatttat actgtcggat ctcctattga ttacggtgtg   4080

atcgttgata ctaaggcata ttcaggaggt tataatcttc caattggtca agcagatgaa   4140

atgcaaagat atgtcgaaga gaatcaaaca agaaacaagc atatcaaccc taatgaatgg   4200

tggaaagtct atccatcttc agtaacagaa tttaagttct tgtttgtgag tggtcatttc   4260

aaaggaaact acaaagctca gcttacaaga ttgaatcata tcactaattg taatggagct   4320

gttcttagtg tagaagagct tttgattggt ggagaaatga ttaaagctgg tacattgaca   4380

cttgaggaag tgagaaggaa atttaataac ggtgagataa acttttaa               4428
```

```
<210> SEQ ID NO 24
<211> LENGTH: 1517
<212> TYPE: PRT
<213> ORGANISM: Xanthomonas oryzae

<400> SEQUENCE: 24

Met Asp Pro Ile Arg Ser Arg Thr Pro Ser Pro Ala Arg Glu Leu Leu
1               5                   10                  15

Pro Gly Pro Gln Pro Asp Arg Val Gln Pro Thr Ala Asp Arg Gly Gly
            20                  25                  30

Ala Pro Pro Ala Gly Gly Pro Leu Asp Gly Leu Pro Ala Arg Arg Thr
        35                  40                  45

Met Glu Thr Ser Arg Thr Arg Leu Pro Ser Pro Pro Ala Pro Ser Pro
    50                  55                  60

Ala Phe Ser Ala Gly Ser Phe Ser Asp Leu Leu Arg Gln Phe Asp Pro
65                  70                  75                  80

Ser Leu Leu Asp Thr Ser Leu Leu Asp Ser Met Pro Ala Val Gly Thr
                85                  90                  95

Pro His Thr Ala Ala Ala Pro Ala Glu Trp Asp Glu Val Gln Ser Gly
            100                 105                 110

Leu Arg Ala Ala Asp Asp Pro Pro Pro Thr Val Arg Val Ala Val Thr
        115                 120                 125

Ala Ala Arg Pro Pro Arg Ala Lys Pro Ala Pro Arg Arg Arg Ala Ala
    130                 135                 140

Gln Pro Ser Asp Ala Ser Pro Ala Ala Gln Val Asp Leu Arg Thr Leu
145                 150                 155                 160

Gly Tyr Ser Gln Gln Gln Gln Glu Lys Ile Lys Pro Lys Val Arg Ser
                165                 170                 175

Thr Val Ala Gln His His Glu Ala Leu Val Gly His Gly Phe Thr His
            180                 185                 190

Ala His Ile Val Ala Leu Ser Gln His Pro Ala Ala Leu Gly Thr Val
        195                 200                 205
```

-continued

```
Ala Val Lys Tyr Gln His Ile Ile Thr Ala Leu Pro Glu Ala Thr His
    210                 215                 220

Glu Asp Ile Val Gly Val Gly Lys Gln Trp Ser Gly Ala Arg Ala Leu
225                 230                 235                 240

Glu Ala Leu Leu Thr Lys Ala Gly Glu Leu Arg Gly Pro Pro Leu Gln
                245                 250                 255

Leu Asp Thr Gly Gln Leu Leu Lys Ile Ala Lys Arg Gly Gly Val Thr
            260                 265                 270

Ala Val Glu Ala Val His Ala Ser Arg Asn Ala Leu Thr Gly Ala Pro
        275                 280                 285

Leu Asn Leu Thr Pro Ala Gln Val Val Ala Ile Ala Asn Asn Asn Gly
    290                 295                 300

Gly Lys Gln Ala Leu Glu Thr Val Gln Arg Leu Leu Pro Val Leu Cys
305                 310                 315                 320

Gln Asp His Gly Leu Thr Gln Asp Gln Val Val Ala Ile Ala Ser His
                325                 330                 335

Asp Gly Gly Lys Gln Ala Leu Glu Thr Val Gln Arg Leu Leu Pro Val
            340                 345                 350

Leu Cys Gln Ala His Gly Leu Thr Pro Ala Gln Val Val Ala Ile Ala
        355                 360                 365

Ser Asn Gly Gly Gly Lys Gln Ala Leu Glu Thr Val Gln Arg Leu Leu
    370                 375                 380

Pro Val Leu Cys Gln Asp His Gly Leu Thr Pro Asp Gln Val Val Ala
385                 390                 395                 400

Ile Ala Ser Asn Gly Gly Gly Lys Gln Ala Leu Glu Thr Val Gln Arg
                405                 410                 415

Leu Leu Pro Val Leu Cys Gln Asp His Gly Leu Thr Pro Asp Gln Val
            420                 425                 430

Val Ala Ile Ala Asn Asn Asn Gly Gly Lys Gln Ala Leu Glu Thr Val
        435                 440                 445

Gln Arg Leu Leu Pro Val Leu Cys Gln Asp His Gly Leu Thr Pro Asp
    450                 455                 460

Gln Val Val Ala Ile Ala Ser Asn Ile Gly Gly Lys Gln Ala Leu Glu
465                 470                 475                 480

Thr Val Gln Arg Leu Leu Pro Val Leu Cys Gln Asp His Gly Leu Thr
                485                 490                 495

Pro Asp Gln Val Val Ala Ile Ala Ser Asn Ile Gly Gly Lys Gln Ala
            500                 505                 510

Leu Glu Thr Val Gln Arg Leu Leu Pro Val Leu Cys Gln Asp His Gly
        515                 520                 525

Leu Thr Pro Asp Gln Val Val Ala Ile Ala Asn Asn Asn Gly Gly Lys
    530                 535                 540

Gln Ala Leu Glu Thr Leu Gln Arg Leu Leu Pro Val Leu Cys Gln Asp
545                 550                 555                 560

His Gly Leu Thr Pro Asp Gln Val Val Ala Ile Ala Asn Asn Asn Gly
                565                 570                 575

Gly Lys Gln Ala Leu Glu Thr Val Gln Arg Leu Leu Pro Val Leu Cys
            580                 585                 590

Gln Asp His Gly Leu Thr Pro Asp Gln Val Val Ala Ile Ala Ser His
        595                 600                 605

Asp Gly Gly Lys Gln Ala Leu Glu Thr Val Gln Arg Leu Leu Pro Val
    610                 615                 620

Leu Cys Gln Asp His Gly Leu Thr Pro Asp Gln Val Val Ala Ile Ala
```

-continued

```
625                 630                 635                 640

Ser Asn Gly Gly Gly Lys Gln Ala Leu Glu Thr Val Gln Arg Leu Leu
                645                 650                 655

Pro Val Leu Cys Gln Asp His Gly Leu Thr Pro Asp Gln Val Val Ala
            660                 665                 670

Ile Ala Ser Asn Gly Gly Gly Lys Gln Ala Leu Glu Thr Val Gln Arg
        675                 680                 685

Leu Leu Pro Val Leu Cys Gln Asp His Gly Leu Thr Pro Asp Gln Val
    690                 695                 700

Val Ala Ile Ala Asn Asn Asn Gly Gly Lys Gln Ala Leu Glu Thr Val
705                 710                 715                 720

Gln Arg Leu Leu Pro Val Leu Cys Gln Asp His Gly Leu Thr Pro Asp
                725                 730                 735

Gln Val Val Ala Ile Ala Ser Asn Ile Gly Gly Lys Gln Ala Leu Glu
            740                 745                 750

Thr Val Gln Arg Leu Leu Pro Val Leu Cys Gln Asp His Gly Leu Thr
        755                 760                 765

Pro Asp Gln Val Val Ala Ile Ala Ser Asn Gly Gly Gly Lys Gln Ala
    770                 775                 780

Leu Glu Thr Val Gln Arg Leu Leu Pro Val Leu Cys Gln Asp His Gly
785                 790                 795                 800

Leu Thr Pro Asp Gln Val Val Ala Ile Ala Asn Asn Asn Gly Gly Lys
                805                 810                 815

Gln Ala Leu Glu Thr Val Gln Arg Leu Leu Pro Val Leu Cys Gln Asp
            820                 825                 830

His Gly Leu Thr Pro Asp Gln Val Val Ala Ile Ala Ser Asn Ile Gly
        835                 840                 845

Gly Lys Gln Ala Leu Glu Thr Val Gln Arg Leu Leu Pro Val Leu Cys
    850                 855                 860

Gln Asp His Gly Leu Thr Pro Asp Gln Val Val Ala Ile Ala Asn Asn
865                 870                 875                 880

Asn Gly Gly Lys Gln Ala Leu Glu Thr Val Gln Arg Leu Leu Pro Val
                885                 890                 895

Leu Cys Gln Asp His Gly Leu Thr Gln Asp Gln Val Val Ala Ile Ala
            900                 905                 910

Ser His Asp Gly Gly Lys Gln Ala Leu Glu Thr Val Gln Arg Leu Leu
        915                 920                 925

Pro Val Leu Cys Gln Asp His Gly Leu Thr Pro Asp Gln Val Val Ala
    930                 935                 940

Thr Ala Ser Asn Gly Gly Gly Lys Gln Ala Leu Glu Thr Val Gln Arg
945                 950                 955                 960

Leu Leu Pro Val Leu Cys Gln Asp His Gly Leu Thr Pro Asp Gln Val
                965                 970                 975

Val Ala Ile Ala Ser Asn Gly Gly Gly Lys Gln Ala Leu Glu Thr Val
            980                 985                 990

Gln Arg Leu Leu Pro Val Leu Cys  Gln Asp His Gly Leu  Thr Pro Asp
        995                 1000                1005

Gln Val  Val Ala Ile Ala Ser  Asn Ile Gly Gly Lys  Gln Ala Leu
    1010                 1015                 1020

Glu Thr  Ile Val Ala Gln Leu  Ser Arg Pro Asp Pro  Ala Leu Ala
    1025                 1030                 1035

Ala Leu  Thr Asn Asp His Leu  Val Ala Leu Ala Cys  Leu Gly Gly
    1040                 1045                 1050
```

-continued

```
Arg Pro  Ala Leu Asp Ala Val  Lys Lys Gly Leu Pro  His Ala Pro
    1055                 1060                 1065

Glu Leu  Ile Arg Arg Ile Asn  Arg Arg Ile Pro Glu  Arg Thr Ser
    1070                 1075                 1080

His Arg  Val Pro Asp Leu Ala  His Val Val Arg Val  Leu Gly Phe
    1085                 1090                 1095

Phe Gln  Ser His Ser His Pro  Ala Gln Ala Phe Asp  Asp Ala Met
    1100                 1105                 1110

Thr Gln  Phe Glu Met Ser Arg  His Gly Leu Val Gln  Leu Phe Arg
    1115                 1120                 1125

Arg Val  Gly Val Thr Glu Phe  Glu Ala Arg Tyr Gly  Thr Leu Pro
    1130                 1135                 1140

Pro Ala  Ser Gln Arg Trp Asp  Arg Ile Leu Gln Ala  Ser Gly Met
    1145                 1150                 1155

Lys Arg  Ala Lys Pro Ser Pro  Thr Ser Ala Gln Thr  Pro Asp Gln
    1160                 1165                 1170

Ala Ser  Leu His Ala Asp Tyr  Lys Asp Asp Asp Asp  Lys Lys Asp
    1175                 1180                 1185

Tyr Lys  Asp Asp Asp Asp Lys  Lys Gly Arg Pro Ser  Pro Met His
    1190                 1195                 1200

Glu Gly  Asp Gln Thr Arg Ala  Ser Ser Arg Lys Arg  Ser Arg Ser
    1205                 1210                 1215

Asp Arg  Ala Val Thr Gly Pro  Ser Thr Gln Gln Ser  Phe Glu Val
    1220                 1225                 1230

Arg Val  Pro Glu Gln Gln Asp  Ala Leu His Leu Pro  Leu Ser Trp
    1235                 1240                 1245

Arg Val  Lys Arg Pro Arg Thr  Arg Ile Gly Gly Gly  Leu Pro Asp
    1250                 1255                 1260

Pro Gly  Thr Pro Ile Ala Ala  Asp Leu Ala Ala Ser  Ser Thr Val
    1265                 1270                 1275

Met Trp  Glu Gln Asp Ala Ala  Pro Phe Ala Gly Ala  Ala Asp Asp
    1280                 1285                 1290

Phe Pro  Ala Phe Asn Glu Glu  Glu Leu Ala Trp Leu  Met Glu Leu
    1295                 1300                 1305

Leu Pro  Gln Ser Gly Ser Val  Gly Gly Thr Ile Ser  Arg Gln Leu
    1310                 1315                 1320

Val Lys  Ser Glu Leu Glu Glu  Lys Lys Ser Glu Leu  Arg His Lys
    1325                 1330                 1335

Leu Lys  Tyr Val Pro His Glu  Tyr Ile Glu Leu Ile  Glu Ile Ala
    1340                 1345                 1350

Arg Asn  Ser Thr Gln Asp Arg  Ile Leu Glu Met Lys  Val Met Glu
    1355                 1360                 1365

Phe Phe  Met Lys Val Tyr Gly  Tyr Arg Gly Lys His  Leu Gly Gly
    1370                 1375                 1380

Ser Arg  Lys Pro Asp Gly Ala  Ile Tyr Thr Val Gly  Ser Pro Ile
    1385                 1390                 1395

Asp Tyr  Gly Val Ile Val Asp  Thr Lys Ala Tyr Ser  Gly Gly Tyr
    1400                 1405                 1410

Asn Leu  Pro Ile Gly Gln Ala  Asp Glu Met Gln Arg  Tyr Val Glu
    1415                 1420                 1425

Glu Asn  Gln Thr Arg Asn Lys  His Ile Asn Pro Asn  Glu Trp Trp
    1430                 1435                 1440
```

-continued

Lys Val Tyr Pro Ser Ser Val Thr Glu Phe Lys Phe Leu Phe Val
1445 1450 1455

Ser Gly His Phe Lys Gly Asn Tyr Lys Ala Gln Leu Thr Arg Leu
1460 1465 1470

Asn His Ile Thr Asn Cys Asn Gly Ala Val Leu Ser Val Glu Glu
1475 1480 1485

Leu Leu Ile Gly Gly Glu Met Ile Lys Ala Gly Thr Leu Thr Leu
1490 1495 1500

Glu Glu Val Arg Arg Lys Phe Asn Asn Gly Glu Ile Asn Phe
1505 1510 1515

<210> SEQ ID NO 25
<211> LENGTH: 1548
<212> TYPE: PRT
<213> ORGANISM: Xanthomonas oryzae

<400> SEQUENCE: 25

Met Asp Pro Ile Arg Ser Arg Thr Pro Ser Pro Ala Arg Glu Leu Leu
1 5 10 15

Pro Gly Pro Gln Pro Asp Arg Val Gln Pro Thr Ala Asp Arg Gly Gly
20 25 30

Ala Pro Pro Ala Gly Gly Pro Leu Asp Gly Leu Pro Ala Arg Arg Thr
35 40 45

Met Ser Arg Thr Arg Leu Pro Ser Pro Pro Ala Pro Ser Pro Ala Phe
50 55 60

Ser Ala Gly Ser Phe Ser Asp Leu Leu Arg Gln Phe Asp Pro Ser Leu
65 70 75 80

Leu Asp Thr Ser Leu Leu Asp Ser Met Pro Ala Val Gly Thr Pro His
85 90 95

Thr Ala Ala Ala Pro Ala Glu Trp Asp Glu Val Gln Ser Gly Leu Arg
100 105 110

Ala Ala Asp Asp Pro Pro Pro Thr Val Arg Val Ala Val Thr Ala Ala
115 120 125

Arg Pro Pro Arg Ala Lys Pro Ala Pro Arg Arg Arg Ala Ala Gln Pro
130 135 140

Ser Asp Ala Ser Pro Ala Ala Gln Val Asp Leu Arg Thr Leu Gly Tyr
145 150 155 160

Ser Gln Gln Gln Gln Glu Lys Ile Lys Pro Lys Val Arg Ser Thr Val
165 170 175

Ala Gln His His Glu Ala Leu Val Gly His Gly Phe Thr His Ala His
180 185 190

Ile Val Ala Leu Ser Gln His Pro Ala Ala Leu Gly Thr Val Ala Val
195 200 205

Lys Tyr Gln His Ile Ile Thr Ala Leu Pro Glu Ala Thr His Glu Asp
210 215 220

Ile Val Gly Val Gly Lys Gln Trp Ser Gly Ala Arg Ala Leu Glu Ala
225 230 235 240

Leu Leu Thr Lys Ala Gly Glu Leu Arg Gly Pro Pro Leu Gln Leu Asp
245 250 255

Thr Gly Gln Leu Leu Lys Ile Ala Lys Arg Gly Gly Val Thr Ala Val
260 265 270

Glu Ala Val His Ala Trp Arg Asn Ala Leu Thr Gly Ala Pro Leu Asn
275 280 285

Leu Thr Pro Ala Gln Val Val Ala Ile Ala Ser His Asp Gly Gly Lys
290 295 300

-continued

```
Gln Ala Leu Glu Thr Val Gln Arg Leu Leu Pro Val Leu Cys Gln Asp
305                 310                 315                 320

His Gly Leu Thr Pro Asp Gln Val Val Ala Ile Ala Ser Asn Ile Gly
                325                 330                 335

Gly Lys Gln Ala Leu Glu Thr Val Gln Arg Leu Leu Pro Val Leu Cys
            340                 345                 350

Gln Asp His Gly Leu Thr Pro Asp Gln Val Val Ala Ile Ala Asn Asn
        355                 360                 365

Asn Gly Gly Lys Gln Ala Leu Glu Thr Val Gln Arg Leu Leu Pro Val
    370                 375                 380

Leu Cys Gln Asp His Gly Leu Thr Pro Asp Gln Val Val Ala Ile Ala
385                 390                 395                 400

Ser His Asp Gly Gly Lys Gln Ala Leu Glu Thr Val Gln Arg Leu Leu
                405                 410                 415

Pro Val Leu Cys Gln Asp His Gly Leu Thr Pro Asp Gln Val Val Ala
            420                 425                 430

Ile Ala Ser Asn Gly Gly Gly Lys Gln Ala Leu Glu Thr Val Gln Arg
        435                 440                 445

Leu Leu Pro Val Leu Cys Gln Asp His Gly Leu Thr Pro Asp Gln Val
    450                 455                 460

Val Ala Ile Ala Ser Asn Ile Gly Gly Lys Gln Ala Leu Glu Thr Val
465                 470                 475                 480

Gln Arg Leu Leu Pro Val Leu Cys Gln Asp His Gly Leu Thr Pro Asp
                485                 490                 495

Gln Val Val Ala Ile Ala Ser His Asp Gly Gly Lys Gln Ala Leu Glu
            500                 505                 510

Thr Val Gln Arg Leu Leu Pro Val Leu Cys Gln Asp His Gly Leu Thr
        515                 520                 525

Pro Asp Gln Val Val Ala Ile Ala Ser Asn Gly Gly Gly Lys Gln Ala
    530                 535                 540

Leu Glu Thr Leu Gln Arg Leu Leu Pro Val Leu Cys Gln Asp His Gly
545                 550                 555                 560

Leu Thr Pro Asp Gln Val Val Ala Ile Ala Ser Asn Ile Gly Gly Lys
                565                 570                 575

Gln Ala Leu Glu Thr Val Gln Arg Leu Leu Pro Val Leu Cys Gln Asp
            580                 585                 590

His Gly Leu Thr Pro Asp Gln Val Val Ala Ile Ala Ser His Asp Gly
        595                 600                 605

Gly Lys Gln Ala Leu Glu Thr Val Gln Arg Leu Leu Pro Val Leu Cys
    610                 615                 620

Gln Asp His Gly Leu Thr Pro Asp Gln Val Val Ala Ile Ala Ser Asn
625                 630                 635                 640

Gly Gly Gly Lys Gln Ala Leu Glu Thr Val Gln Arg Leu Leu Pro Val
                645                 650                 655

Leu Cys Gln Asp His Gly Leu Thr Pro Asp Gln Val Val Ala Ile Ala
            660                 665                 670

Ser Asn Gly Gly Gly Lys Gln Ala Leu Glu Thr Val Gln Arg Leu Leu
        675                 680                 685

Pro Val Leu Cys Gln Asp His Gly Leu Thr Pro Asp Gln Val Val Ala
    690                 695                 700

Ile Ala Asn Asn Asn Gly Gly Lys Gln Ala Leu Glu Thr Val Gln Arg
705                 710                 715                 720
```

-continued

```
Leu Leu Pro Val Leu Cys Gln Asp His Gly Leu Thr Pro Asp Gln Val
                725                 730                 735

Val Ala Ile Ala Ser Asn Ile Gly Gly Lys Gln Ala Leu Glu Thr Val
            740                 745                 750

Gln Arg Leu Leu Pro Val Leu Cys Gln Asp His Gly Leu Thr Pro Asp
        755                 760                 765

Gln Val Val Ala Ile Ala Asn Asn Asn Gly Gly Lys Gln Ala Leu Glu
    770                 775                 780

Thr Val Gln Arg Leu Leu Pro Val Leu Cys Gln Asp His Gly Leu Thr
785                 790                 795                 800

Pro Asp Gln Val Val Ala Ile Ala Ser Asn Gly Gly Gly Lys Gln Ala
                805                 810                 815

Leu Glu Thr Val Gln Arg Leu Leu Pro Val Leu Cys Gln Ala His Gly
            820                 825                 830

Leu Thr Pro Ala Gln Val Val Ala Ile Ala Ser Asn Gly Gly Gly Lys
        835                 840                 845

Gln Ala Leu Glu Thr Val Gln Arg Leu Leu Pro Val Leu Cys Gln Asp
    850                 855                 860

His Gly Leu Thr Pro Asp Gln Val Val Ala Ile Ala Ser Asn Gly Gly
865                 870                 875                 880

Gly Lys Gln Ala Leu Glu Thr Val Gln Arg Leu Leu Pro Val Leu Cys
                885                 890                 895

Gln Asp His Gly Leu Thr Pro Asp Gln Val Val Ala Ile Ala Asn Asn
            900                 905                 910

Asn Gly Gly Lys Gln Ala Leu Glu Thr Val Gln Arg Leu Leu Pro Val
        915                 920                 925

Leu Cys Gln Asp His Gly Leu Thr Pro Asp Gln Val Val Ala Ile Ala
    930                 935                 940

Ser His Asp Gly Gly Lys Gln Ala Leu Glu Thr Val Gln Arg Leu Leu
945                 950                 955                 960

Pro Val Leu Cys Gln Asp His Gly Leu Thr Pro Asp Gln Val Val Ala
                965                 970                 975

Ile Ala Ser Asn Gly Gly Gly Lys Gln Ala Leu Glu Thr Val Gln Arg
            980                 985                 990

Leu Leu Pro Val Leu Cys Gln Asp  His Gly Leu Thr Pro  Asp Gln Val
        995                 1000                1005

Val Ala  Ile Ala Ser Asn Gly  Gly Gly Lys Gln Ala  Leu Glu Thr
    1010                1015                1020

Val Gln  Arg Leu Leu Pro Val  Leu Cys Gln Asp His  Gly Leu Thr
    1025                1030                1035

Pro Asn  Gln Val Val Ala Ile  Ala Ser Asn Gly Gly  Lys Gln Ala
    1040                1045                1050

Leu Glu  Ser Ile Val Ala Gln  Leu Ser Arg Pro Asp  Pro Ala Leu
    1055                1060                1065

Ala Ala  Leu Thr Asn Asp His  Leu Val Ala Leu Ala  Cys Leu Gly
    1070                1075                1080

Gly Arg  Pro Ala Leu Asp Ala  Val Lys Lys Gly Leu  Pro His Ala
    1085                1090                1095

Pro Glu  Leu Ile Arg Arg Ile  Asn Arg Arg Ile Pro  Glu Arg Thr
    1100                1105                1110

Ser His  Arg Val Pro Asp Leu  Ala His Val Val Arg  Val Leu Gly
    1115                1120                1125

Phe Phe  Gln Ser His Ser His  Pro Ala Gln Ala Phe  Asp Asp Ala
```

-continued

```
    1130                1135                1140

Met Thr  Gln Phe Glu Met Ser  Arg His Gly Leu Val  Gln Leu Phe
    1145                1150                1155

Arg Arg  Val Gly Val Thr Glu  Phe Glu Ala Arg Tyr  Gly Thr Leu
    1160                1165                1170

Pro Pro  Ala Ser Gln Arg Trp  Asp Arg Ile Leu Gln  Ala Ser Gly
    1175                1180                1185

Met Lys  Arg Ala Lys Pro Ser  Pro Thr Ser Ala Gln  Thr Pro Asp
    1190                1195                1200

Gln Ala  Ser Leu His Ala Asp  Tyr Lys Asp Asp Asp  Asp Lys Lys
    1205                1210                1215

Asp Tyr  Lys Asp Asp Asp Asp  Lys Lys Gly Arg Pro  Ser Pro Met
    1220                1225                1230

His Glu  Gly Asp Gln Thr Arg  Ala Ser Ser Arg Lys  Arg Ser Arg
    1235                1240                1245

Ser Asp  Arg Ala Val Thr Gly  Pro Ser Thr Gln Gln  Ser Phe Glu
    1250                1255                1260

Val Arg  Val Pro Glu Gln Gln  Asp Ala Leu His Leu  Pro Leu Ser
    1265                1270                1275

Trp Arg  Val Lys Arg Pro Arg  Thr Arg Ile Gly Gly  Gly Leu Pro
    1280                1285                1290

Asp Pro  Gly Thr Pro Ile Ala  Ala Asp Leu Ala Ala  Ser Ser Thr
    1295                1300                1305

Val Met  Trp Glu Gln Asp Ala  Ala Pro Phe Ala Gly  Ala Ala Asp
    1310                1315                1320

Asp Phe  Pro Ala Phe Asn Glu  Glu Glu Leu Ala Trp  Leu Met Glu
    1325                1330                1335

Leu Leu  Pro Gln Ser Gly Ser  Val Gly Gly Thr Ile  Ser Arg Gln
    1340                1345                1350

Leu Val  Lys Ser Glu Leu Glu  Glu Lys Lys Ser Glu  Leu Arg His
    1355                1360                1365

Lys Leu  Lys Tyr Val Pro His  Glu Tyr Ile Glu Leu  Ile Glu Ile
    1370                1375                1380

Ala Arg  Asn Ser Thr Gln Asp  Arg Ile Leu Glu Met  Lys Val Met
    1385                1390                1395

Glu Phe  Phe Met Lys Val Tyr  Gly Tyr Arg Gly Lys  His Leu Gly
    1400                1405                1410

Gly Ser  Arg Lys Pro Asp Gly  Ala Ile Tyr Thr Val  Gly Ser Pro
    1415                1420                1425

Ile Asp  Tyr Gly Val Ile Val  Asp Thr Lys Ala Tyr  Ser Gly Gly
    1430                1435                1440

Tyr Asn  Leu Pro Ile Gly Gln  Ala Asp Glu Met Gln  Arg Tyr Val
    1445                1450                1455

Glu Glu  Asn Gln Thr Arg Asn  Lys His Ile Asn Pro  Asn Glu Trp
    1460                1465                1470

Trp Lys  Val Tyr Pro Ser Ser  Val Thr Glu Phe Lys  Phe Leu Phe
    1475                1480                1485

Val Ser  Gly His Phe Lys Gly  Asn Tyr Lys Ala Gln  Leu Thr Arg
    1490                1495                1500

Leu Asn  His Ile Thr Asn Cys  Asn Gly Ala Val Leu  Ser Val Glu
    1505                1510                1515

Glu Leu  Leu Ile Gly Gly Glu  Met Ile Lys Ala Gly  Thr Leu Thr
    1520                1525                1530
```

-continued

Leu Glu Glu Val Arg Arg Lys Phe Asn Asn Gly Glu Ile Asn Phe
1535 1540 1545

<210> SEQ ID NO 26
<211> LENGTH: 1475
<212> TYPE: PRT
<213> ORGANISM: Xanthomonas oryzae

<400> SEQUENCE: 26

Met Asp Pro Ile Arg Ser Arg Thr Pro Ser Pro Ala Arg Glu Leu Leu
1 5 10 15

Pro Gly Pro Gln Pro Asp Arg Val Gln Pro Thr Ala Asp Arg Gly Gly
20 25 30

Ala Pro Pro Ala Gly Gly Pro Leu Asp Gly Leu Pro Ala Arg Arg Thr
35 40 45

Met Ser Arg Thr Arg Leu Pro Ser Pro Pro Ala Pro Ser Pro Ala Phe
50 55 60

Ser Ala Gly Ser Phe Ser Asp Leu Leu Arg Gln Phe Asp Pro Ser Leu
65 70 75 80

Leu Asp Thr Ser Leu Leu Asp Ser Met Pro Ala Val Gly Thr Pro His
85 90 95

Thr Ala Ala Ala Pro Ala Glu Trp Asp Glu Val Gln Ser Gly Leu Arg
100 105 110

Ala Ala Asp Asp Pro Pro Pro Thr Val Arg Val Ala Val Thr Ala Ala
115 120 125

Arg Pro Pro Arg Ala Lys Pro Ala Pro Arg Arg Arg Ala Ala Gln Pro
130 135 140

Ser Asp Ala Ser Pro Ala Ala Gln Val Asp Leu Arg Thr Leu Gly Tyr
145 150 155 160

Ser Gln Gln Gln Gln Glu Lys Ile Lys Pro Lys Val Arg Ser Thr Val
165 170 175

Ala Gln His His Glu Ala Leu Val Gly His Gly Phe Thr His Ala His
180 185 190

Ile Val Ala Leu Ser Gln His Pro Ala Ala Leu Gly Thr Val Ala Val
195 200 205

Lys Tyr Gln His Ile Ile Thr Ala Leu Pro Glu Ala Thr His Glu Asp
210 215 220

Ile Val Gly Val Gly Lys Gln Trp Ser Gly Ala Arg Ala Leu Glu Ala
225 230 235 240

Leu Leu Thr Lys Ala Gly Glu Leu Arg Gly Pro Pro Leu Gln Leu Asp
245 250 255

Thr Gly Gln Leu Leu Lys Ile Ala Lys Arg Gly Gly Val Thr Ala Val
260 265 270

Glu Ala Val His Ala Ser Arg Asn Ala Leu Thr Gly Ala Pro Leu Asn
275 280 285

Leu Thr Pro Ala Gln Val Val Ala Ile Ala Ser His Asp Gly Gly Lys
290 295 300

Gln Ala Leu Glu Thr Val Gln Arg Leu Leu Pro Val Leu Cys Gln Asp
305 310 315 320

His Gly Leu Thr Pro Asp Gln Val Val Ala Ile Ala Ser Asn Gly Gly
325 330 335

Gly Lys Gln Ala Leu Glu Thr Val Gln Arg Leu Leu Pro Val Leu Cys
340 345 350

Gln Ala His Gly Leu Thr Pro Ala Gln Val Val Ala Ile Ala Ser Asn

-continued

```
        355                 360                 365

Gly Gly Gly Lys Gln Ala Leu Glu Thr Val Gln Arg Leu Leu Pro Val
    370                 375                 380

Leu Cys Gln Asp His Gly Leu Thr Gln Asp Gln Val Val Ala Ile Ala
385                 390                 395                 400

Ser His Asp Gly Gly Lys Gln Ala Leu Glu Thr Val Gln Arg Leu Leu
                405                 410                 415

Pro Val Leu Cys Gln Asp His Gly Leu Thr Pro Asp Gln Val Val Ala
            420                 425                 430

Ile Ala Ser His Asp Gly Gly Lys Gln Ala Leu Glu Thr Val Gln Arg
        435                 440                 445

Leu Leu Pro Val Leu Cys Gln Asp His Gly Leu Thr Pro Asp Gln Val
    450                 455                 460

Val Ala Ile Ala Ser Asn Gly Gly Gly Lys Gln Ala Leu Glu Thr Val
465                 470                 475                 480

Gln Arg Leu Leu Pro Val Leu Cys Gln Asp His Gly Leu Thr Pro Asp
                485                 490                 495

Gln Val Val Ala Ile Ala Ser Asn Gly Gly Gly Lys Gln Ala Leu Glu
            500                 505                 510

Thr Val Gln Arg Leu Leu Pro Val Leu Cys Gln Asp His Gly Leu Thr
        515                 520                 525

Gln Asp Gln Val Val Ala Ile Ala Ser His Asp Gly Gly Lys Gln Ala
    530                 535                 540

Leu Glu Thr Leu Gln Arg Leu Leu Pro Val Leu Cys Gln Asp His Gly
545                 550                 555                 560

Leu Thr Pro Asp Gln Val Val Ala Ile Ala Ser His Asp Gly Gly Lys
                565                 570                 575

Gln Ala Leu Glu Thr Val Gln Arg Leu Leu Pro Val Leu Cys Gln Ala
            580                 585                 590

His Gly Leu Thr Pro Ala Gln Val Val Ala Ile Ala Ser Asn Gly Gly
        595                 600                 605

Gly Lys Gln Ala Leu Glu Thr Val Gln Arg Leu Leu Pro Val Leu Cys
    610                 615                 620

Gln Asp His Gly Leu Thr Pro Asp Gln Val Val Ala Ile Ala Ser Asn
625                 630                 635                 640

Ile Gly Gly Lys Gln Ala Leu Glu Thr Val Gln Arg Leu Leu Pro Val
                645                 650                 655

Leu Cys Gln Asp His Gly Leu Thr Pro Asp Gln Val Val Ala Ile Ala
            660                 665                 670

Asn Asn Asn Gly Gly Lys Gln Ala Leu Glu Thr Val Gln Arg Leu Leu
        675                 680                 685

Pro Val Leu Cys Gln Gly His Gly Leu Thr Gln Asp Gln Val Val Ala
    690                 695                 700

Ile Ala Ser His Asp Gly Gly Lys Gln Ala Leu Glu Thr Val Gln Arg
705                 710                 715                 720

Leu Leu Pro Val Leu Cys Gln Asp His Gly Leu Thr Pro Asp Gln Val
                725                 730                 735

Val Ala Ile Ala Ser Asn Ile Gly Gly Lys Gln Ala Leu Glu Thr Val
            740                 745                 750

Gln Arg Leu Leu Pro Val Leu Cys Gln Asp His Gly Leu Thr Pro Asp
        755                 760                 765

Gln Val Val Ala Ile Ala Ser His Asp Gly Gly Lys Gln Ala Leu Glu
    770                 775                 780
```

-continued

Thr Val Gln Arg Leu Leu Pro Val Leu Cys Gln Asp His Gly Leu Thr
785 790 795 800

Pro Asp Gln Val Val Ala Ile Ala Ser Asn Gly Gly Gly Lys Gln Ala
805 810 815

Leu Glu Thr Val Gln Arg Leu Leu Pro Val Leu Cys Gln Asp His Gly
820 825 830

Leu Thr Pro Asp Gln Val Val Ala Ile Ala Ser Asn Ile Gly Gly Lys
835 840 845

Gln Ala Leu Glu Thr Val Gln Arg Leu Leu Pro Val Leu Cys Gln Asp
850 855 860

His Gly Leu Thr Pro Asp Gln Val Val Ala Ile Ala Ser Asn Gly Gly
865 870 875 880

Gly Lys Gln Ala Leu Glu Thr Val Gln Arg Leu Leu Pro Val Leu Cys
885 890 895

Gln Asp His Gly Leu Thr Pro Asp Gln Val Val Ala Ile Ala Ser Asn
900 905 910

Ile Gly Gly Lys Gln Ala Leu Glu Thr Val Gln Arg Leu Leu Pro Val
915 920 925

Leu Cys Gln Asp His Gly Leu Thr Pro Asp Gln Val Val Ala Ile Ala
930 935 940

Ser Asn Gly Gly Gly Lys Gln Ala Leu Glu Thr Val Gln Arg Leu Leu
945 950 955 960

Pro Val Leu Cys Gln Asp His Gly Leu Thr Pro Asp Gln Val Val Ala
965 970 975

Ile Ala Ser Asn Ile Gly Gly Lys Gln Ala Leu Glu Thr Val Gln Arg
980 985 990

Leu Leu Pro Val Leu Cys Gln Asp His Gly Leu Thr Pro Asp Gln Val
995 1000 1005

Val Ala Ile Ala Ser Asn Ile Gly Gly Lys Gln Ala Leu Glu Thr
1010 1015 1020

Ile Val Ala Gln Leu Ser Arg Pro Asp Pro Ala Leu Ala Ala Leu
1025 1030 1035

Thr Asn Asp His Leu Val Ala Leu Ala Cys Leu Gly Gly Arg Pro
1040 1045 1050

Ala Leu Asp Ala Val Lys Lys Gly Leu Pro His Ala Pro Glu Leu
1055 1060 1065

Ile Arg Arg Ile Asn Arg Arg Ile Pro Glu Arg Thr Ser His Arg
1070 1075 1080

Val Pro Asp Leu Ala His Val Val Arg Val Leu Gly Phe Phe Gln
1085 1090 1095

Ser His Ser His Pro Ala Gln Ala Phe Asp Asp Ala Met Thr Gln
1100 1105 1110

Phe Glu Met Ser Arg His Gly Leu Val Gln Leu Phe Arg Arg Val
1115 1120 1125

Gly Val Thr Glu Phe Glu Ala Arg Tyr Gly Thr Leu Pro Pro Ala
1130 1135 1140

Ser Gln Arg Trp Asp Arg Ile Leu Gln Ala Ser Gly Met Lys Arg
1145 1150 1155

Ala Lys Pro Ser Pro Thr Ser Ala Gln Thr Pro Asp Gln Ala Ser
1160 1165 1170

Leu His Ala Asp Tyr Lys Asp Asp Asp Asp Lys Lys Asp Tyr Lys
1175 1180 1185

-continued

```
Asp Asp  Asp Asp Lys Lys Gly  Arg Pro Ser Pro Met  His Glu Gly
    1190                 1195                 1200

Asp Gln  Thr Gly Ala Ser Ser  Arg Lys Arg Ser Arg  Ser Asp Arg
    1205                 1210                 1215

Ala Val  Thr Gly Pro Ser Ala  Gln Gln Ser Phe Glu  Val Arg Val
    1220                 1225                 1230

Pro Glu  Gln Arg Asp Ala Leu  His Leu Pro Leu Ser  Trp Arg Val
    1235                 1240                 1245

Lys Arg  Pro Arg Thr Arg Ile  Gly Gly Gly Leu Pro  Asp Pro Gly
    1250                 1255                 1260

Thr Pro  Ile Ala Ala Asp Leu  Ala Ala Ser Ser Thr  Val Ile Arg
    1265                 1270                 1275

Ser Gln  Leu Val Lys Ser Glu  Leu Glu Glu Lys Lys  Ser Glu Leu
    1280                 1285                 1290

Arg His  Lys Leu Lys Tyr Val  Pro His Glu Tyr Ile  Glu Leu Ile
    1295                 1300                 1305

Glu Ile  Ala Arg Asn Ser Thr  Gln Asp Arg Ile Leu  Glu Met Lys
    1310                 1315                 1320

Val Met  Glu Phe Phe Met Lys  Val Tyr Gly Tyr Arg  Gly Lys His
    1325                 1330                 1335

Leu Gly  Gly Ser Arg Lys Pro  Asp Gly Ala Ile Tyr  Thr Val Gly
    1340                 1345                 1350

Ser Pro  Ile Asp Tyr Gly Val  Ile Val Asp Thr Lys  Ala Tyr Ser
    1355                 1360                 1365

Gly Gly  Tyr Asn Leu Pro Ile  Gly Gln Ala Asp Glu  Met Gln Arg
    1370                 1375                 1380

Tyr Val  Glu Glu Asn Gln Thr  Arg Asn Lys His Ile  Asn Pro Asn
    1385                 1390                 1395

Glu Trp  Trp Lys Val Tyr Pro  Ser Ser Val Thr Glu  Phe Lys Phe
    1400                 1405                 1410

Leu Phe  Val Ser Gly His Phe  Lys Gly Asn Tyr Lys  Ala Gln Leu
    1415                 1420                 1425

Thr Arg  Leu Asn His Ile Thr  Asn Cys Asn Gly Ala  Val Leu Ser
    1430                 1435                 1440

Val Glu  Glu Leu Leu Ile Gly  Gly Glu Met Ile Lys  Ala Gly Thr
    1445                 1450                 1455

Leu Thr  Leu Glu Glu Val Arg  Arg Lys Phe Asn Asn  Gly Glu Ile
    1460                 1465                 1470

Asn Phe
    1475
```

<210> SEQ ID NO 27
<211> LENGTH: 23
<212> TYPE: DNA
<213> ORGANISM: Xanthomonas oryzae

<400> SEQUENCE: 27
tcccttaact aggacaactt gga 23

<210> SEQ ID NO 28
<211> LENGTH: 29
<212> TYPE: DNA
<213> ORGANISM: Xanthomonas oryzae

<400> SEQUENCE: 28
ccggatccag ccattgcagc aagatcttg 29

<210> SEQ ID NO 29
<211> LENGTH: 20
<212> TYPE: DNA
<213> ORGANISM: Xanthomonas oryzae

<400> SEQUENCE: 29
catggctgtg attgatcagg 20

<210> SEQ ID NO 30
<211> LENGTH: 24
<212> TYPE: DNA
<213> ORGANISM: Xanthomonas oryzae

<400> SEQUENCE: 30
gagaagaagg tagctgcatg agtg 24

<210> SEQ ID NO 31
<211> LENGTH: 25
<212> TYPE: DNA
<213> ORGANISM: Xanthomonas oryzae

<400> SEQUENCE: 31
tcatggaagg aacccttaca ggttg 25

<210> SEQ ID NO 32
<211> LENGTH: 21
<212> TYPE: DNA
<213> ORGANISM: Xanthomonas oryzae

<400> SEQUENCE: 32
agaaggcgta ggcattcaca t 21

<210> SEQ ID NO 33
<211> LENGTH: 23
<212> TYPE: DNA
<213> ORGANISM: Xanthomonas oryzae

<400> SEQUENCE: 33
acattaacac agcacacgtc aac 23

<210> SEQ ID NO 34
<211> LENGTH: 27
<212> TYPE: DNA
<213> ORGANISM: Xanthomonas oryzae

<400> SEQUENCE: 34
ctactcagcc aataaattga taactgc 27

<210> SEQ ID NO 35
<211> LENGTH: 24
<212> TYPE: DNA
<213> ORGANISM: Xanthomonas oryzae

<400> SEQUENCE: 35
caatttctac tactcatcgt ttag 24

<210> SEQ ID NO 36
<211> LENGTH: 3942
<212> TYPE: DNA
<213> ORGANISM: Xanthomonas oryzae

<400> SEQUENCE: 36

-continued

```
ggtaccagat ctgccaccat ggatcccatt cgttcgcgca cgccaagtcc tgcccgcgag     60
cttctgcccg gaccccaacc ggatagggtt cagccgactg cagatcgggg gggggctccg    120
cctgctggcg gccccctgga tggcttgccc gctcggcgga cgatgtcccg gacccggctg    180
ccatctcccc ctgcgccctc gcctgcgttc tcggcgggca gcttcagcga tctgctccgt    240
cagttcgatc cgtcgcttct tgatacatcg cttcttgatt cgatgcctgc cgtcggcacg    300
ccgcatacag cggctgcccc agcagagtgg gatgaggtgc aatcgggtct gcgtgcagcc    360
gatgacccgc cacccaccgt gcgtgtcgct gtcactgccg cgcggccgcc gcgcgccaag    420
ccggccccgc gacggcgtgc ggcgcaaccc tccgacgctt cgccggccgc gcaggtggat    480
ctacgcacgc tcggctacag tcagcagcag caagagaaga tcaaaccgaa ggtgcgttcg    540
acagtggcgc agcaccacga ggcactggtg ggccatgggt ttacacacgc gcacatcgtt    600
gcgctcagcc aacacccggc agcgttaggg accgtcgctg tcaagtatca gcacataatc    660
acggcgttgc cagaggcgac acacgaagac atcgttggcg tcggcaaaca gtggtccggc    720
gcacgcgccc tggaggcctt gctcacgaag gcgggggagt tgagaggtcc gccgttacag    780
ttggacacag gccaacttct caagattgca aaacgtggcg gcgtgaccgc agtggaggca    840
gtgcatgcat ggcgcaatgc actgacgggt gccccccctga acctgacccc ggaccaagtg    900
gtggccatcg ccagcaatgg cggcggcaag caggcactag aaacggtgca gcggctgttg    960
ccggtgctgt gccaggacca tggcctgacc ccggaccagg tggtggccat cgccagcaat   1020
attggcggca agcaggctct tgaaacggtg cagcggctgt tgccggtgct gtgccaggac   1080
catggcctga ccccggacca agtggtggcc atcgccaaca ataacggcgg caagcaggcg   1140
ttggaaacgg tgcagcggct gttgccggtg ctgtgccagg accatggcct gaccccggac   1200
caggtcgtgg ccatcgccag caatattggc ggcaagcagg cgctcgaaac ggtgcagcgg   1260
ctgttgccgg tgctgtgcca ggcccatggc ctgaccccgg accaagtggt ggccatcgcc   1320
agcaatggcg gcggcaagca ggcagttgaa acggtgcagc ggctgttgcc ggtgctgtgc   1380
caggaccatg gcctgacccc ggaccaggtg gtggccatcg ccagcaatat tggcggcaag   1440
caggctgtag aaacggtgca gcggctgttg ccggtgctgt gccaggccca tggcctgacc   1500
ccggcccaag tggtggccat cgccagcaat ggcggcggca agcaggccgt ggaaacggtg   1560
cagcggctgt tgccggtgct gtgccaggac catggcctga ccccggacca agtggtggcc   1620
atcgccaaca ataacggcgg caagcaggcg gtcgaaacgg tgcagcggct gttgccggtg   1680
ctgtgccagg accatggcct gaccccggac caagtcgtgg ccatcgccag ccacgatggc   1740
ggcaagcagg cactggaaac actgcagcgg ctgttgccgg tgctgtgcca ggaccatggc   1800
ctgaccccgg accaggtcgt ggccatcgcc agcaatattg gcggcaagca ggcactagaa   1860
acggtgcagc ggctgttgcc ggtgctgtgc caggcccatg gcctgacccc ggcccaagtg   1920
gtggccatcg ccagcaatgg cggcggcaag caggctcttg aaacggtgca gcggctgttg   1980
ccggtgctgt gccaggacca tggcctgacc ccggaccaag tcgtggccat cgccagccac   2040
gatggcggca agcaggcgtt ggaaacggtg cagcggctgt tgccggtgct gtgccaggcc   2100
catggcctga ccccggccca agtggtggcc atcgccagca atggcggcgg caagcaggcg   2160
ctcgaaacgg tgcagcggct gttgccggtg ctgtgccagg accatggcct gaccccggac   2220
caagtcgtgg ccatcgccag ccacgatggc ggcaagcagg cagttgaaac ggtgcagcgg   2280
ctgttgccgg tgctgtgcca ggaccatggc ctgaccccgg accaagtcgt ggccatcgcc   2340
agccacgatg gcggcaagca ggctgtagaa acggtgcagc ggctgttgcc ggtgctgtgc   2400
```

caggaccatg gcctgacccc ggaccaagtc gtggccatcg ccagccacga tggcggcaag 2460
caggccgtgg aaacggtgca gcggctgttg ccggtgctgt gccaggacca tggcctgacc 2520
ccgaaccagg tggtggccat cgccagcaat ggcggcaagc aggcgctgga gagcattgtt 2580
gcccagttat ctcgccctga tccggcgttg gccgcgttga ccaacgacca cctcgtcgcc 2640
ttggcctgcc tcggcggacg tcctgccctg gatgcagtga aaaagggatt gccgcacgcg 2700
ccggaattga tcagaagaat caatcgccgc attcccgaac gcacgtccca tcgcgttccc 2760
gacctcgcgc acgtggttcg cgtgcttggt tttttccaga gccactccca cccagcgcaa 2820
gcattcgatg acgccatgac gcagttcgag atgagcaggc acggcttggt acagctcttt 2880
cgcagagtgg gcgtcaccga attcgaagcc cgctacggaa cgctcccccc agcctcgcag 2940
cgttgggacc gtatcctcca ggcatcaggg atgaaaaggg ccaaaccgtc ccctacttca 3000
gctcaaacac cggatcaggc gtctttacat gcagattaca aggacgacga cgacaagaag 3060
gattacaagg acgacgacga caagaagggt cgacccagcc caatgcacga gggagatcag 3120
acgcgggcaa gcagccgtaa acggtcccga tcggatcgtg ctgtcaccgg cccctccaca 3180
cagcaatctt tcgaggtgcg cgttcccgaa cagcaagatg cgctgcattt gcccctcagc 3240
tggagggtaa aacgcccgcg taccaggatc gggggcggcc tcccggatcc tggtacgccc 3300
atcgctgccg acctggcagc gtccagcacc gtgatgtcta gacagctagt gaaatctgaa 3360
ttggaagaga agaaatctga acttagacat aaattgaaat atgtgccaca tgaatatatt 3420
gaattgattg aaatcgcaag aaattcaact caggatagaa tccttgaaat gaaggtgatg 3480
gagttcttta tgaaggttta tggttatcgt ggtaaacatt tgggtggatc aaggaaacca 3540
gacggagcaa tttatactgt cggatctcct attgattacg gtgtgatcgt tgatactaag 3600
gcatattcag gaggttataa tcttccaatt ggtcaagcag atgaaatgca aagatatgtc 3660
gaagagaatc aaacaagaaa caagcatatc aaccctaatg aatggtggaa agtctatcca 3720
tcttcagtaa cagaatttaa gttcttgttt gtgagtggtc atttcaaagg aaactacaaa 3780
gctcagctta caagattgaa tcatatcact aattgtaatg gagctgttct tagtgtagaa 3840
gagcttttga ttggtggaga aatgattaaa gctggtacat tgacacttga ggaagtgaga 3900
aggaaattta ataacggtga gataaacttt taatagacta gt 3942

<210> SEQ ID NO 37
<211> LENGTH: 1304
<212> TYPE: PRT
<213> ORGANISM: Xanthomonas oryzae

<400> SEQUENCE: 37

Met Asp Pro Ile Arg Ser Arg Thr Pro Ser Pro Ala Arg Glu Leu Leu
1 5 10 15

Pro Gly Pro Gln Pro Asp Arg Val Gln Pro Thr Ala Asp Arg Gly Gly
20 25 30

Ala Pro Pro Ala Gly Gly Pro Leu Asp Gly Leu Pro Ala Arg Arg Thr
35 40 45

Met Ser Arg Thr Arg Leu Pro Ser Pro Pro Ala Pro Ser Pro Ala Phe
50 55 60

Ser Ala Gly Ser Phe Ser Asp Leu Leu Arg Gln Phe Asp Pro Ser Leu
65 70 75 80

Leu Asp Thr Ser Leu Leu Asp Ser Met Pro Ala Val Gly Thr Pro His
85 90 95

-continued

```
Thr Ala Ala Ala Pro Ala Glu Trp Asp Glu Val Gln Ser Gly Leu Arg
            100                 105                 110

Ala Ala Asp Asp Pro Pro Pro Thr Val Arg Val Ala Val Thr Ala Ala
        115                 120                 125

Arg Pro Pro Arg Ala Lys Pro Ala Pro Arg Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln His Ile Ile Thr Ala Leu Pro Glu Ala Thr His Glu Asp
    210                 215                 220

Ile Val Gly Val Gly Lys Gln Trp Ser Gly Ala Arg Ala Leu Glu Ala
225                 230                 235                 240

Leu Leu Thr Lys Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285

Leu Thr Pro Asp Gln Val Val Ala Ile Ala Ser Asn Gly Gly Gly Lys
    290                 295                 300

Gln Ala Leu Glu Thr Val Gln Arg Leu Leu Pro Val Leu Cys Gln Asp
305                 310                 315                 320

His Gly Leu Thr Pro Asp Gln Val Val Ala Ile Ala Ser Asn Ile Gly
                325                 330                 335

Gly Lys Gln Ala Leu Glu Thr Val Gln Arg Leu Leu Pro Val Leu Cys
            340                 345                 350

Gln Asp His Gly Leu Thr Pro Asp Gln Val Val Ala Ile Ala Asn Asn
        355                 360                 365

Asn Gly Gly Lys Gln Ala Leu Glu Thr Val Gln Arg Leu Leu Pro Val
    370                 375                 380

Leu Cys Gln Asp His Gly Leu Thr Pro Asp Gln Val Val Ala Ile Ala
385                 390                 395                 400

Ser Asn Ile Gly Gly Lys Gln Ala Leu Glu Thr Val Gln Arg Leu Leu
                405                 410                 415

Pro Val Leu Cys Gln Ala His Gly Leu Thr Pro Asp Gln Val Val Ala
            420                 425                 430

Ile Ala Ser Asn Gly Gly Gly Lys Gln Ala Val Glu Thr Val Gln Arg
        435                 440                 445

Leu Leu Pro Val Leu Cys Gln Asp His Gly Leu Thr Pro Asp Gln Val
    450                 455                 460

Val Ala Ile Ala Ser Asn Ile Gly Gly Lys Gln Ala Val Glu Thr Val
465                 470                 475                 480

Gln Arg Leu Leu Pro Val Leu Cys Gln Ala His Gly Leu Thr Pro Ala
                485                 490                 495

Gln Val Val Ala Ile Ala Ser Asn Gly Gly Gly Lys Gln Ala Val Glu
            500                 505                 510

Thr Val Gln Arg Leu Leu Pro Val Leu Cys Gln Asp His Gly Leu Thr
```

-continued

```
        515                 520                 525

Pro Asp Gln Val Val Ala Ile Ala Asn Asn Asn Gly Gly Lys Gln Ala
    530                 535                 540

Val Glu Thr Val Gln Arg Leu Leu Pro Val Leu Cys Gln Asp His Gly
545                 550                 555                 560

Leu Thr Pro Asp Gln Val Val Ala Ile Ala Ser His Asp Gly Gly Lys
                565                 570                 575

Gln Ala Leu Glu Thr Leu Gln Arg Leu Leu Pro Val Leu Cys Gln Asp
            580                 585                 590

His Gly Leu Thr Pro Asp Gln Val Val Ala Ile Ala Ser Asn Ile Gly
        595                 600                 605

Gly Lys Gln Ala Leu Glu Thr Val Gln Arg Leu Leu Pro Val Leu Cys
    610                 615                 620

Gln Ala His Gly Leu Thr Pro Ala Gln Val Val Ala Ile Ala Ser Asn
625                 630                 635                 640

Gly Gly Gly Lys Gln Ala Leu Glu Thr Val Gln Arg Leu Leu Pro Val
                645                 650                 655

Leu Cys Gln Asp His Gly Leu Thr Pro Asp Gln Val Val Ala Ile Ala
            660                 665                 670

Ser His Asp Gly Gly Lys Gln Ala Leu Glu Thr Val Gln Arg Leu Leu
        675                 680                 685

Pro Val Leu Cys Gln Ala His Gly Leu Thr Pro Ala Gln Val Val Ala
    690                 695                 700

Ile Ala Ser Asn Gly Gly Gly Lys Gln Ala Leu Glu Thr Val Gln Arg
705                 710                 715                 720

Leu Leu Pro Val Leu Cys Gln Asp His Gly Leu Thr Pro Asp Gln Val
                725                 730                 735

Val Ala Ile Ala Ser His Asp Gly Gly Lys Gln Ala Val Glu Thr Val
            740                 745                 750

Gln Arg Leu Leu Pro Val Leu Cys Gln Asp His Gly Leu Thr Pro Asp
        755                 760                 765

Gln Val Val Ala Ile Ala Ser His Asp Gly Gly Lys Gln Ala Val Glu
    770                 775                 780

Thr Val Gln Arg Leu Leu Pro Val Leu Cys Gln Asp His Gly Leu Thr
785                 790                 795                 800

Pro Asp Gln Val Val Ala Ile Ala Ser His Asp Gly Gly Lys Gln Ala
                805                 810                 815

Val Glu Thr Val Gln Arg Leu Leu Pro Val Leu Cys Gln Asp His Gly
            820                 825                 830

Leu Thr Pro Asn Gln Val Val Ala Ile Ala Ser Asn Gly Gly Lys Gln
        835                 840                 845

Ala Leu Glu Ser Ile Val Ala Gln Leu Ser Arg Pro Asp Pro Ala Leu
    850                 855                 860

Ala Ala Leu Thr Asn Asp His Leu Val Ala Leu Ala Cys Leu Gly Gly
865                 870                 875                 880

Arg Pro Ala Leu Asp Ala Val Lys Lys Gly Leu Pro His Ala Pro Glu
                885                 890                 895

Leu Ile Arg Arg Ile Asn Arg Arg Ile Pro Glu Arg Thr Ser His Arg
            900                 905                 910

Val Pro Asp Leu Ala His Val Val Arg Val Leu Gly Phe Phe Gln Ser
        915                 920                 925

His Ser His Pro Ala Gln Ala Phe Asp Asp Ala Met Thr Gln Phe Glu
    930                 935                 940
```

-continued

Met Ser Arg His Gly Leu Val Gln Leu Phe Arg Arg Val Gly Val Thr
945 950 955 960

Glu Phe Glu Ala Arg Tyr Gly Thr Leu Pro Pro Ala Ser Gln Arg Trp
965 970 975

Asp Arg Ile Leu Gln Ala Ser Gly Met Lys Arg Ala Lys Pro Ser Pro
980 985 990

Thr Ser Ala Gln Thr Pro Asp Gln Ala Ser Leu His Ala Asp Tyr Lys
995 1000 1005

Asp Asp Asp Asp Lys Lys Asp Tyr Lys Asp Asp Asp Asp Lys Lys
1010 1015 1020

Gly Arg Pro Ser Pro Met His Glu Gly Asp Gln Thr Arg Ala Ser
1025 1030 1035

Ser Arg Lys Arg Ser Arg Ser Asp Arg Ala Val Thr Gly Pro Ser
1040 1045 1050

Thr Gln Gln Ser Phe Glu Val Arg Val Pro Glu Gln Gln Asp Ala
1055 1060 1065

Leu His Leu Pro Leu Ser Trp Arg Val Lys Arg Pro Arg Thr Arg
1070 1075 1080

Ile Gly Gly Gly Leu Pro Asp Pro Gly Thr Pro Ile Ala Ala Asp
1085 1090 1095

Leu Ala Ala Ser Ser Thr Val Met Ser Arg Gln Leu Val Lys Ser
1100 1105 1110

Glu Leu Glu Glu Lys Lys Ser Glu Leu Arg His Lys Leu Lys Tyr
1115 1120 1125

Val Pro His Glu Tyr Ile Glu Leu Ile Glu Ile Ala Arg Asn Ser
1130 1135 1140

Thr Gln Asp Arg Ile Leu Glu Met Lys Val Met Glu Phe Phe Met
1145 1150 1155

Lys Val Tyr Gly Tyr Arg Gly Lys His Leu Gly Gly Ser Arg Lys
1160 1165 1170

Pro Asp Gly Ala Ile Tyr Thr Val Gly Ser Pro Ile Asp Tyr Gly
1175 1180 1185

Val Ile Val Asp Thr Lys Ala Tyr Ser Gly Gly Tyr Asn Leu Pro
1190 1195 1200

Ile Gly Gln Ala Asp Glu Met Gln Arg Tyr Val Glu Glu Asn Gln
1205 1210 1215

Thr Arg Asn Lys His Ile Asn Pro Asn Glu Trp Trp Lys Val Tyr
1220 1225 1230

Pro Ser Ser Val Thr Glu Phe Lys Phe Leu Phe Val Ser Gly His
1235 1240 1245

Phe Lys Gly Asn Tyr Lys Ala Gln Leu Thr Arg Leu Asn His Ile
1250 1255 1260

Thr Asn Cys Asn Gly Ala Val Leu Ser Val Glu Glu Leu Leu Ile
1265 1270 1275

Gly Gly Glu Met Ile Lys Ala Gly Thr Leu Thr Leu Glu Glu Val
1280 1285 1290

Arg Arg Lys Phe Asn Asn Gly Glu Ile Asn Phe
1295 1300

<210> SEQ ID NO 38
<211> LENGTH: 4674
<212> TYPE: DNA
<213> ORGANISM: Xanthomonas oryzae

<400> SEQUENCE: 38
ggtaccagat ctgccaccat ggatcccatt cgttcgcgca cgccaagtcc tgcccgcgag 60
cttctgcccg gaccccaacc ggatagggtt cagccgactg cagatcgggg gggggctccg 120
cctgctggcg gccccctgga tggcttgccc gctcggcgga cgatgtcccg gacccggctg 180
ccatctcccc ctgcgccctc gcctgcgttc tcggcgggca gcttcagcga tctgctccgt 240
cagttcgatc cgtcgcttct tgatacatcg cttcttgatt cgatgcctgc cgtcggcacg 300
ccgcatacag cggctgcccc agcagagtgg gatgaggtgc aatcgggtct gcgtgcagcc 360
gatgacccgc cacccaccgt gcgtgtcgct gtcactgccg cgcggccgcc gcgcgccaag 420
ccggccccgc gacggcgtgc ggcgcaaccc tccgacgctt cgccggccgc gcaggtggat 480
ctacgcacgc tcggctacag tcagcagcag caagagaaga tcaaaccgaa ggtgcgttcg 540
acagtggcgc agcaccacga ggcactggtg ggccatgggt ttacacacgc gcacatcgtt 600
gcgctcagcc aacacccggc agcgttaggg accgtcgctg tcaagtatca gcacataatc 660
acggcgttgc cagaggcgac acacgaagac atcgttggcg tcggcaaaca gtggtccggc 720
gcacgcgccc tggaggcctt gctcacgaag gcgggggagt tgagaggtcc gccgttacag 780
ttggacacag gccaacttct caagattgca aaacgtggcg gcgtgaccgc agtggaggca 840
gtgcatgcat ggcgcaatgc actgacgggt gcccccctga acctgacccc ggaccaagtg 900
gtggccatcg ccagcaatat tggcggcaag caggcactag aaacggtgca gcggctgttg 960
ccggtgctgt gccaggccca tggcctgacc ccggcccaag tggtggccat cgccagcaat 1020
ggcggcggca agcaggctct tgaaacggtg cagcggctgt tgccggtgct gtgccaggac 1080
catggcctga ccccggacca ggtggtggcc atcgccagca atattggcgg caagcaggcg 1140
ttggaaacgg tgcagcggct gttgccggtg ctgtgccagg cccatggcct gaccccggcc 1200
caagtggtgg ccatcgccag caatggcggc ggcaagcagg cgctcgaaac ggtgcagcgg 1260
ctgttgccgg tgctgtgcca ggaccatggc ctgaccccgg accaggtcgt ggccatcgcc 1320
agcaatattg gcggcaagca ggcagttgaa acggtgcagc ggctgttgcc ggtgctgtgc 1380
caggaccatg gcctgacccc ggaccaagtg gtggccatcg ccaacaataa cggcggcaag 1440
caggctgtag aaacggtgca gcggctgttg ccggtgctgt gccaggccca tggcctgacc 1500
ccggcccaag tggtggccat cgccagcaat ggcggcggca agcaggccgt ggaaacggtg 1560
cagcggctgt tgccggtgct gtgccaggcc catggcctga ccccggacca agtggtggcc 1620
atcgccagca atggcggcgg caagcaggca ctggaaacac tgcagcggct gttgccggtg 1680
ctgtgccagg accatggcct gaccccggac caagtggtgg ccatcgccaa caataacggc 1740
ggcaagcagg cactagaaac ggtgcagcgg ctgttgccgg tgctgtgcca ggaccatggc 1800
ctgaccccgg accaagtggt ggccatcgcc aacaataacg gcggcaagca ggctcttgaa 1860
acggtgcagc ggctgttgcc ggtgctgtgc caggaccatg gcctgacccc ggaccaggtg 1920
gtggccatcg ccagcaatat tggcggcaag caggcgttgg aaacggtgca gcggctgttg 1980
ccggtgctgt gccaggacca tggcctgacc ccggaccaag tggtggccat cgccaacaat 2040
aacggcggca agcaggcgct cgaaacggtg cagcggctgt tgccggtgct gtgccaggac 2100
catggcctga ccccggacca ggtcgtggcc atcgccagca atattggcgg caagcaggca 2160
gttgaaacgg tgcagcggct gttgccggtg ctgtgccagg accatggcct gaccccggac 2220
caagtcgtgg ccatcgccag ccacgatggc ggcaagcagg ctgtagaaac ggtgcagcgg 2280
ctgttgccgg tgctgtgcca ggaccatggc ctgaccccgg accaagtcgt ggccatcgcc 2340

-continued

```
agccacgatg gcggcaagca ggccgtggaa acggtgcagc ggctgttgcc ggtgctgtgc   2400
caggaccatg gcctgacccc ggaccaggtg gtggccatcg ccagccacga tggcggcaag   2460
caggcgctgg aaactgtaca gcggctgttg ccggtgctgt gccaggccca tggcctgacc   2520
ccggaccaag tggtggccat cgccagcaat ggcggcggca agcaggcact agaaacggtg   2580
cagcggctgt tgccggtgct gtgccaggac catggcctga ccccggacca ggtggtggcc   2640
atcgccagcc acgatggcgg caagcaggct cttgaaacgg tgcagcggct gttgccggtg   2700
ctgtgccagg accatggcct gaccccggac caagtcgtgg ccatcgccag ccacgatggc   2760
ggcaagcagg cgttggaaac ggtgcagcgg ctgttgccgg tgctgtgcca ggaccatggc   2820
ctgaccccgg accaggtcgt ggccatcgcc agcaatattg gcggcaagca ggcgctcgaa   2880
acggtgcagc ggctgttgcc ggtgctgtgc caggaccatg gcctgacccc ggaccaagtc   2940
gtggccatcg ccagccacga tggcggcaag caggcagttg aaacggtgca gcggctgttg   3000
ccggtgctgt gccaggccca tggcctgacc ccggcccaag tggtggccat cgccagcaat   3060
ggcggcggca agcaggctgt agaaacggtg cagcggctgt tgccggtgct gtgccaggac   3120
catggcctga ccccgaacca ggtggtggcc atcgccagca atggcggcaa gcaggcgctg   3180
gagagcattg ttgcccagtt atctcgccct gatccggcgt tggccgcgtt gaccaacgac   3240
cacctcgtcg ccttggcctg cctcggcgga cgtcctgccc tggatgcagt gaaaaaggga   3300
ttgccgcacg cgccggaatt gatcagaaga atcaatcgcc gcattcccga acgcacgtcc   3360
catcgcgttc ccgacctcgc gcacgtggtt cgcgtgcttg gtttttttcca gagccactcc   3420
cacccagcgc aagcattcga tgacgccatg acgcagttcg agatgagcag gcacggcttg   3480
gtacagctct ttcgcagagt gggcgtcacc gaattcgaag cccgctacgg aacgctcccc   3540
ccagcctcgc agcgttggga ccgtatcctc caggcatcag ggatgaaaag ggccaaaccg   3600
tcccctactt cagctcaaac accggatcag gcgtctttac atgcagatta caaggacgac   3660
gacgacaaga aggattacaa ggacgacgac gacaagaagg gtcgacccag cccaatgcac   3720
gagggagatc agacgcgggc aagcagccgt aaacggtccc gatcggatcg tgctgtcacc   3780
ggcccctcca cacagcaatc tttcgaggtg cgcgttcccg aacagcaaga tgcgctgcat   3840
ttgcccctca gctggagggt aaaacgcccg cgtaccagga tcgggggcgg cctcccggat   3900
cctggtacgc ccatcgctgc cgacctggca gcgtccagca ccgtgatgtg ggaacaagat   3960
gcggcccccct tcgcaggggc agcggatgat ttcccggcat tcaacgaaga ggagctcgca   4020
tggttgatgg agctattgcc tcagtcaggc tcagtcggag ggacgatctc tagacagcta   4080
gtgaaatctg aattggaaga gaagaaatct gaacttagac ataaattgaa atatgtgcca   4140
catgaatata ttgaattgat tgaaatcgca agaaattcaa ctcaggatag aatccttgaa   4200
atgaaggtga tggagttctt tatgaaggtt tatggttatc gtggtaaaca tttgggtgga   4260
tcaaggaaac cagacggagc aatttatact gtcggatctc ctattgatta cggtgtgatc   4320
gttgatacta aggcatattc aggaggttat aatcttccaa ttggtcaagc agatgaaatg   4380
caaagatatg tcgaagagaa tcaaacaaga aacaagcata tcaaccctaa tgaatggtgg   4440
aaagtctatc catcttcagt aacagaattt aagttcttgt ttgtgagtgg tcatttcaaa   4500
ggaaactaca aagctcagct tacaagattg aatcatatca ctaattgtaa tggagctgtt   4560
cttagtgtag aagagctttt gattggtgga gaaatgatta aagctggtac attgacactt   4620
gaggaagtga gaaggaaatt taataacggt gagataaact tttaatagac tagt         4674
```

<210> SEQ ID NO 39
<211> LENGTH: 1548
<212> TYPE: PRT
<213> ORGANISM: Xanthomonas oryzae

<400> SEQUENCE: 39

Met Asp Pro Ile Arg Ser Arg Thr Pro Ser Pro Ala Arg Glu Leu Leu
1 5 10 15

Pro Gly Pro Gln Pro Asp Arg Val Gln Pro Thr Ala Asp Arg Gly Gly
20 25 30

Ala Pro Pro Ala Gly Gly Pro Leu Asp Gly Leu Pro Ala Arg Arg Thr
35 40 45

Met Ser Arg Thr Arg Leu Pro Ser Pro Pro Ala Pro Ser Pro Ala Phe
50 55 60

Ser Ala Gly Ser Phe Ser Asp Leu Leu Arg Gln Phe Asp Pro Ser Leu
65 70 75 80

Leu Asp Thr Ser Leu Leu Asp Ser Met Pro Ala Val Gly Thr Pro His
85 90 95

Thr Ala Ala Ala Pro Ala Glu Trp Asp Glu Val Gln Ser Gly Leu Arg
100 105 110

Ala Ala Asp Asp Pro Pro Pro Thr Val Arg Val Ala Val Thr Ala Ala
115 120 125

Arg Pro Pro Arg Ala Lys Pro Ala Pro Arg Arg Arg Ala Ala Gln Pro
130 135 140

Ser Asp Ala Ser Pro Ala Ala Gln Val Asp Leu Arg Thr Leu Gly Tyr
145 150 155 160

Ser Gln Gln Gln Gln Glu Lys Ile Lys Pro Lys Val Arg Ser Thr Val
165 170 175

Ala Gln His His Glu Ala Leu Val Gly His Gly Phe Thr His Ala His
180 185 190

Ile Val Ala Leu Ser Gln His Pro Ala Ala Leu Gly Thr Val Ala Val
195 200 205

Lys Tyr Gln His Ile Ile Thr Ala Leu Pro Glu Ala Thr His Glu Asp
210 215 220

Ile Val Gly Val Gly Lys Gln Trp Ser Gly Ala Arg Ala Leu Glu Ala
225 230 235 240

Leu Leu Thr Lys Ala Gly Glu Leu Arg Gly Pro Pro Leu Gln Leu Asp
245 250 255

Thr Gly Gln Leu Leu Lys Ile Ala Lys Arg Gly Gly Val Thr Ala Val
260 265 270

Glu Ala Val His Ala Trp Arg Asn Ala Leu Thr Gly Ala Pro Leu Asn
275 280 285

Leu Thr Pro Asp Gln Val Val Ala Ile Ala Ser Asn Ile Gly Gly Lys
290 295 300

Gln Ala Leu Glu Thr Val Gln Arg Leu Leu Pro Val Leu Cys Gln Ala
305 310 315 320

His Gly Leu Thr Pro Ala Gln Val Val Ala Ile Ala Ser Asn Gly Gly
325 330 335

Gly Lys Gln Ala Leu Glu Thr Val Gln Arg Leu Leu Pro Val Leu Cys
340 345 350

Gln Asp His Gly Leu Thr Pro Asp Gln Val Val Ala Ile Ala Ser Asn
355 360 365

Ile Gly Gly Lys Gln Ala Leu Glu Thr Val Gln Arg Leu Leu Pro Val
370 375 380

-continued

Leu Cys Gln Ala His Gly Leu Thr Pro Ala Gln Val Val Ala Ile Ala
385 390 395 400

Ser Asn Gly Gly Gly Lys Gln Ala Leu Glu Thr Val Gln Arg Leu Leu
405 410 415

Pro Val Leu Cys Gln Asp His Gly Leu Thr Pro Asp Gln Val Val Ala
420 425 430

Ile Ala Ser Asn Ile Gly Gly Lys Gln Ala Val Glu Thr Val Gln Arg
435 440 445

Leu Leu Pro Val Leu Cys Gln Asp His Gly Leu Thr Pro Asp Gln Val
450 455 460

Val Ala Ile Ala Asn Asn Asn Gly Gly Lys Gln Ala Val Glu Thr Val
465 470 475 480

Gln Arg Leu Leu Pro Val Leu Cys Gln Ala His Gly Leu Thr Pro Ala
485 490 495

Gln Val Val Ala Ile Ala Ser Asn Gly Gly Gly Lys Gln Ala Val Glu
500 505 510

Thr Val Gln Arg Leu Leu Pro Val Leu Cys Gln Ala His Gly Leu Thr
515 520 525

Pro Asp Gln Val Val Ala Ile Ala Ser Asn Gly Gly Gly Lys Gln Ala
530 535 540

Leu Glu Thr Leu Gln Arg Leu Leu Pro Val Leu Cys Gln Asp His Gly
545 550 555 560

Leu Thr Pro Asp Gln Val Val Ala Ile Ala Asn Asn Asn Gly Gly Lys
565 570 575

Gln Ala Leu Glu Thr Val Gln Arg Leu Leu Pro Val Leu Cys Gln Asp
580 585 590

His Gly Leu Thr Pro Asp Gln Val Val Ala Ile Ala Asn Asn Asn Gly
595 600 605

Gly Lys Gln Ala Leu Glu Thr Val Gln Arg Leu Leu Pro Val Leu Cys
610 615 620

Gln Asp His Gly Leu Thr Pro Asp Gln Val Val Ala Ile Ala Ser Asn
625 630 635 640

Ile Gly Gly Lys Gln Ala Leu Glu Thr Val Gln Arg Leu Leu Pro Val
645 650 655

Leu Cys Gln Asp His Gly Leu Thr Pro Asp Gln Val Val Ala Ile Ala
660 665 670

Asn Asn Asn Gly Gly Lys Gln Ala Leu Glu Thr Val Gln Arg Leu Leu
675 680 685

Pro Val Leu Cys Gln Asp His Gly Leu Thr Pro Asp Gln Val Val Ala
690 695 700

Ile Ala Ser Asn Ile Gly Gly Lys Gln Ala Val Glu Thr Val Gln Arg
705 710 715 720

Leu Leu Pro Val Leu Cys Gln Asp His Gly Leu Thr Pro Asp Gln Val
725 730 735

Val Ala Ile Ala Ser His Asp Gly Gly Lys Gln Ala Val Glu Thr Val
740 745 750

Gln Arg Leu Leu Pro Val Leu Cys Gln Asp His Gly Leu Thr Pro Asp
755 760 765

Gln Val Val Ala Ile Ala Ser His Asp Gly Gly Lys Gln Ala Val Glu
770 775 780

Thr Val Gln Arg Leu Leu Pro Val Leu Cys Gln Asp His Gly Leu Thr
785 790 795 800

-continued

```
Pro Asp Gln Val Val Ala Ile Ala Ser His Asp Gly Gly Lys Gln Ala
                805                 810                 815

Leu Glu Thr Val Gln Arg Leu Leu Pro Val Leu Cys Gln Ala His Gly
            820                 825                 830

Leu Thr Pro Asp Gln Val Val Ala Ile Ala Ser Asn Gly Gly Gly Lys
        835                 840                 845

Gln Ala Leu Glu Thr Val Gln Arg Leu Leu Pro Val Leu Cys Gln Asp
    850                 855                 860

His Gly Leu Thr Pro Asp Gln Val Val Ala Ile Ala Ser His Asp Gly
865                 870                 875                 880

Gly Lys Gln Ala Leu Glu Thr Val Gln Arg Leu Leu Pro Val Leu Cys
                885                 890                 895

Gln Asp His Gly Leu Thr Pro Asp Gln Val Val Ala Ile Ala Ser His
            900                 905                 910

Asp Gly Gly Lys Gln Ala Leu Glu Thr Val Gln Arg Leu Leu Pro Val
        915                 920                 925

Leu Cys Gln Asp His Gly Leu Thr Pro Asp Gln Val Val Ala Ile Ala
    930                 935                 940

Ser Asn Ile Gly Gly Lys Gln Ala Leu Glu Thr Val Gln Arg Leu Leu
945                 950                 955                 960

Pro Val Leu Cys Gln Asp His Gly Leu Thr Pro Asp Gln Val Val Ala
                965                 970                 975

Ile Ala Ser His Asp Gly Gly Lys Gln Ala Val Glu Thr Val Gln Arg
            980                 985                 990

Leu Leu Pro Val Leu Cys Gln Ala  His Gly Leu Thr Pro  Ala Gln Val
        995                 1000                1005

Val Ala  Ile Ala Ser Asn Gly  Gly Gly Lys Gln Ala  Val Glu Thr
    1010                1015                1020

Val Gln  Arg Leu Leu Pro Val  Leu Cys Gln Asp His  Gly Leu Thr
    1025                1030                1035

Pro Asn  Gln Val Val Ala Ile  Ala Ser Asn Gly Gly  Lys Gln Ala
    1040                1045                1050

Leu Glu  Ser Ile Val Ala Gln  Leu Ser Arg Pro Asp  Pro Ala Leu
    1055                1060                1065

Ala Ala  Leu Thr Asn Asp His  Leu Val Ala Leu Ala  Cys Leu Gly
    1070                1075                1080

Gly Arg  Pro Ala Leu Asp Ala  Val Lys Lys Gly Leu  Pro His Ala
    1085                1090                1095

Pro Glu  Leu Ile Arg Arg Ile  Asn Arg Arg Ile Pro  Glu Arg Thr
    1100                1105                1110

Ser His  Arg Val Pro Asp Leu  Ala His Val Val Arg  Val Leu Gly
    1115                1120                1125

Phe Phe  Gln Ser His Ser His  Pro Ala Gln Ala Phe  Asp Asp Ala
    1130                1135                1140

Met Thr  Gln Phe Glu Met Ser  Arg His Gly Leu Val  Gln Leu Phe
    1145                1150                1155

Arg Arg  Val Gly Val Thr Glu  Phe Glu Ala Arg Tyr  Gly Thr Leu
    1160                1165                1170

Pro Pro  Ala Ser Gln Arg Trp  Asp Arg Ile Leu Gln  Ala Ser Gly
    1175                1180                1185

Met Lys  Arg Ala Lys Pro Ser  Pro Thr Ser Ala Gln  Thr Pro Asp
    1190                1195                1200

Gln Ala  Ser Leu His Ala Asp  Tyr Lys Asp Asp Asp  Asp Lys Lys
```

-continued

```
    1205                1210                1215

Asp Tyr  Lys Asp Asp Asp Asp  Lys Lys Gly Arg Pro  Ser Pro Met
    1220                1225                1230

His Glu  Gly Asp Gln Thr Arg  Ala Ser Ser Arg Lys  Arg Ser Arg
    1235                1240                1245

Ser Asp  Arg Ala Val Thr Gly  Pro Ser Thr Gln Gln  Ser Phe Glu
    1250                1255                1260

Val Arg  Val Pro Glu Gln Gln  Asp Ala Leu His Leu  Pro Leu Ser
    1265                1270                1275

Trp Arg  Val Lys Arg Pro Arg  Thr Arg Ile Gly Gly  Gly Leu Pro
    1280                1285                1290

Asp Pro  Gly Thr Pro Ile Ala  Ala Asp Leu Ala Ala  Ser Ser Thr
    1295                1300                1305

Val Met  Trp Glu Gln Asp Ala  Ala Pro Phe Ala Gly  Ala Ala Asp
    1310                1315                1320

Asp Phe  Pro Ala Phe Asn Glu  Glu Glu Leu Ala Trp  Leu Met Glu
    1325                1330                1335

Leu Leu  Pro Gln Ser Gly Ser  Val Gly Gly Thr Ile  Ser Arg Gln
    1340                1345                1350

Leu Val  Lys Ser Glu Leu Glu  Glu Lys Lys Ser Glu  Leu Arg His
    1355                1360                1365

Lys Leu  Lys Tyr Val Pro His  Glu Tyr Ile Glu Leu  Ile Glu Ile
    1370                1375                1380

Ala Arg  Asn Ser Thr Gln Asp  Arg Ile Leu Glu Met  Lys Val Met
    1385                1390                1395

Glu Phe  Phe Met Lys Val Tyr  Gly Tyr Arg Gly Lys  His Leu Gly
    1400                1405                1410

Gly Ser  Arg Lys Pro Asp Gly  Ala Ile Tyr Thr Val  Gly Ser Pro
    1415                1420                1425

Ile Asp  Tyr Gly Val Ile Val  Asp Thr Lys Ala Tyr  Ser Gly Gly
    1430                1435                1440

Tyr Asn  Leu Pro Ile Gly Gln  Ala Asp Glu Met Gln  Arg Tyr Val
    1445                1450                1455

Glu Glu  Asn Gln Thr Arg Asn  Lys His Ile Asn Pro  Asn Glu Trp
    1460                1465                1470

Trp Lys  Val Tyr Pro Ser Ser  Val Thr Glu Phe Lys  Phe Leu Phe
    1475                1480                1485

Val Ser  Gly His Phe Lys Gly  Asn Tyr Lys Ala Gln  Leu Thr Arg
    1490                1495                1500

Leu Asn  His Ile Thr Asn Cys  Asn Gly Ala Val Leu  Ser Val Glu
    1505                1510                1515

Glu Leu  Leu Ile Gly Gly Glu  Met Ile Lys Ala Gly  Thr Leu Thr
    1520                1525                1530

Leu Glu  Glu Val Arg Arg Lys  Phe Asn Asn Gly Glu  Ile Asn Phe
    1535                1540                1545
```

<210> SEQ ID NO 40
<211> LENGTH: 34
<212> TYPE: DNA
<213> ORGANISM: Xanthomonas oryzae

<400> SEQUENCE: 40
caccggtacc tgagtggtca tacgtgtcat attg 34

<210> SEQ ID NO 41
<211> LENGTH: 29
<212> TYPE: DNA
<213> ORGANISM: Xanthomonas oryzae

<400> SEQUENCE: 41
ccggatccat tgctactggt gatgaaggt 29

<210> SEQ ID NO 42
<211> LENGTH: 24
<212> TYPE: DNA
<213> ORGANISM: Xanthomonas oryzae

<400> SEQUENCE: 42
gcatctcccc ctactgtaca ccac 24

<210> SEQ ID NO 43
<211> LENGTH: 57
<212> TYPE: DNA
<213> ORGANISM: Xanthomonas oryzae

<400> SEQUENCE: 43
tagatatgca tctcccccta ctgtacacca ccaaaagtgg agggtctcca actatat 57

<210> SEQ ID NO 44
<211> LENGTH: 51
<212> TYPE: DNA
<213> ORGANISM: Xanthomonas oryzae

<400> SEQUENCE: 44
tagatatgca tctcccccta cccaccaaaa gtggagggtc tccaactata t 51

<210> SEQ ID NO 45
<211> LENGTH: 49
<212> TYPE: DNA
<213> ORGANISM: Xanthomonas oryzae

<400> SEQUENCE: 45
tagatatgca tctcccccta caccaaaagt ggagggtctc caactatat 49

<210> SEQ ID NO 46
<211> LENGTH: 36
<212> TYPE: DNA
<213> ORGANISM: Xanthomonas oryzae

<400> SEQUENCE: 46
tagatatgca tctctgtgga gggtctccaa ctatat 36

<210> SEQ ID NO 47
<211> LENGTH: 43
<212> TYPE: DNA
<213> ORGANISM: Xanthomonas oryzae

<400> SEQUENCE: 47
tagatatgca tctccaccaa aagtggaggg tctccaacta tat 43

<210> SEQ ID NO 48
<211> LENGTH: 59
<212> TYPE: DNA
<213> ORGANISM: Xanthomonas oryzae

<400> SEQUENCE: 48
cttccttcct agcactatat aaaccccctc caggtgctaa gctcatcaag ccttcaagc 59

-continued

```
<210> SEQ ID NO 49
<211> LENGTH: 33
<212> TYPE: PRT
<213> ORGANISM: Xanthomonas oryzae

<400> SEQUENCE: 49

Asn Gly Asn Ile Asn Asn Asn Ile Asn Gly Asn Ile Asn Gly Asn Asn
1               5                   10                  15

His Asp Asn Ile Asn Gly His Asp Asn Gly His Asp His Asp His Asp
            20                  25                  30

Asn


<210> SEQ ID NO 50
<211> LENGTH: 17
<212> TYPE: DNA
<213> ORGANISM: Xanthomonas oryzae

<400> SEQUENCE: 50

tagatatgca tctcccc                                                    17


<210> SEQ ID NO 51
<211> LENGTH: 43
<212> TYPE: PRT
<213> ORGANISM: Xanthomonas oryzae

<400> SEQUENCE: 51

Asn Ile Asn Gly Asn Ile Asn Gly Asn Ile Asn Asn Asn Gly Asn Gly
1               5                   10                  15

Asn Asn Asn Asn Asn Ile Asn Asn Asn Ile His Asp His Asp His Asp
            20                  25                  30

Asn Gly His Asp His Asp Asn Ile His Asp Asn
        35                  40


<210> SEQ ID NO 52
<211> LENGTH: 22
<212> TYPE: DNA
<213> ORGANISM: Xanthomonas oryzae

<400> SEQUENCE: 52

atatagttgg agaccctcca ct                                              22
```

GENETICALLY MODIFIED PLANTS WITH RESISTANCE TO *XANTHOMONAS* AND OTHER BACTERIAL PLANT PATHOGENS

CROSS-REFERENCE TO RELATED APPLICATIONS

This is a National Phase application claiming priority to PCT/US2012/71722 filed Dec. 27, 2012 which claims priority under 35 U.S.C. §119 to provisional application U.S. Ser. No. 61/581,356 filed Dec. 28, 2011, all of which are herein incorporated by reference in their entireties.

GRANT REFERENCE

This invention was made with government support under Grant No. DBI-0820831 awarded by US National Science Foundation. The government has certain rights in the invention.

TECHNICAL FIELD

The invention relates to the control of pathogens. Disclosed herein are methods of producing transgenic plants with increased pathogen resistance, mutated pathogen target sequences, that prevent pathogen activation but retain activity for normal plant development, polynucleotides for engineering the same, and transgenic plants and seeds generated therefrom.

BACKGROUND OF THE INVENTION

Bacterial blight of rice, caused by the pathogenic bacterium *Xanthomonas oryzae* pv. *oryzae* (Xoo), is one of the most devastating rice diseases, often resulting in yield losses of up to 50% and sometimes destroying an entire crop. The outcome of this disease is largely dictated by a few transcription activator-like (TAL) effectors that are secreted from bacteria into host rice cells. These TAL effectors bind to endogenous promoters and activate expression of corresponding disease susceptibility (S) genes. Such TAL effectors are essentially virulence factors of the pathogenic strains, and the host S gene induction is required for the plant to become susceptible to the disease. Thus the components of this disease complex represent a target for intervention. Complicating intervention strategies, the S genes are critical to plant survival and play an important role in growth and development in rice, making typical knockout strategies inappropriate.

The known TAL effectors of essential virulence include PthXo1, AvrXa7, PthXo3, and PthXo2 in a variety of Xoo strains, while the corresponding S genes are s11N3, Os8N3, and Os12N3 of the N3 family of rice. Naturally occurring genetic variations within the promoter regions of Os8N3 and Os12N3 prevent their inducibility and have been found to confer resistance to the strains that depend on the respective PthXo1 and PthXo2 for virulence in the otherwise susceptible rice cultivars. There is no known genetic variation in Os11N3 that confers disease resistance to AvrXa7 and PthXo3-dependant Xoo strains.

TAL effector nucleases (TALENs), fusion proteins of the DNA cleavage domain of endonuclease FokI and the various forms of TAL effectors (native or custom-made, truncated or complete), have quickly emerged as efficient endonucleases to direct double-strand DNA breaks and induce genetic alterations at pre-selected loci in presumably any eukaryotic organism.

A need exists in the art for plants that are resistant to *Xanthomonas oryzae* pv. *oryzae* (Xoo).

It is an object of the present invention to provide mutations in the Os11N3 promoter region that cause resistance to Xoo while still retaining plant growth and plant reproduction.

It is further object of the present invention to provide mutations in the promoter regions of other S genes, either individually or tandemly, that cause resistance to Xoo while still retaining plant growth and plant reproduction.

SUMMARY OF THE INVENTION

According to the invention, Applicants have successfully generated heritable phenotypes in plants making them resistant to bacterial blight. TAL effector binding elements (EBEs) of bacterial pathogen disease susceptibility genes which are targeted by TAL effectors of essential virulence are modified to prevent induction of expression associated with disease states caused by the bacterial pathogens. Surprisingly, Applicants have found that modifications may be made in the EBEs of these genes which prevent bacterial pathogen induction, but still allow for normal plant development and seed production.

In one embodiment, EBE regions of the N3 family of genes in rice are modified with deletions or insertions while the TATAAA box region remains intact. This includes but is not limited to Os11N3 (EBE SEQ ID NO:16 (−258 to −231 from the Os11N3 ATG start site) and SEQ ID NO:17 (−260 to −232 from the Os11N3 ATG start site), Os8N3 (EBE SEQ ID NO:19), and Os12N3 (EBE SEQ ID NO:18) of the N3 family of rice. According to the invention the EBEs are modified so that TAL effectors of essential virulence PthXo1, AvrXa7, PthXo3, and PthXo2 are prevented from induction of expression, while plant growth and seed development are retained.

In one embodiment, Applicants have identified and created modifications in the overlapping PthXo3 and AvrXa7 EBEs of Os11N3 that inhibit the induction by AvrXa7 and PthXo3, and yet surprisingly plants with these modifications still exhibit normal plant growth and seed production. The overlapping portions (SEQ ID NO:20) of the two EBEs which do not include the TATAAA box are thus targeted and subjected to modification according to the invention.

In one embodiment, the invention includes a modified Os11N3 EBE nucleic acid sequence of SEQ ID NOS: 5, 6, 7, or 9 which provides resistance to Xoo-mediated induction and bacterial blight, but which also maintains normal plant growth and development. SEQ ID NO:5 is a deletion of 9 nucleotides from wild type SEQ ID NO:1, bases 27-35, SEQ ID NO: 6 is a deletion of 5 nucleotides or bases 27-31 from wild type SEQ ID NO:1, SEQ ID NO: 7 is a deletion of 4 nucleotides or bases 34-38 from wild type SEQ ID NO:1, and SEQ ID NO: 9 is an insertion of 9 bases (gtttatata) between bases 37 and 38 from wild type SEQ ID NO:1.

In another embodiment, a nucleotide sequence that is at least 90 or greater, 95% or greater percent similar to SEQ ID NO: 5, 6, 7, or 9 which still inhibits AvrXa7 or PthXo3 induction yet retains normal plant development. In yet another embodiment, a nucleotide sequence that hybridizes to SEQ ID NO 5, 6, 7, or 9 under stringent hybridization conditions involving, for example, hybridization in a hybridization buffer containing, for example, 20 percent formamide in 0.9M saline/0.09M SSC buffer, at a temperature of about 42° C. which still inhibits AvrXa7 or PthXo3 induction yet retains normal plant development are also within the scope of the invention. The invention also includes, plants, cells, seeds, plant tissues and the like which include this modification.

The present invention also relates to a method of imparting bacterial blight resistance to plants. This method involves providing a plant or plant seed comprising a modified EBE such as SEQ ID NO:5, 6, 7, or 9 and growing the modified plant or a plant produced from the modified plant seed under conditions effective to impart resistance to the plant. The present invention further relates to plants produced by this method, as well as component parts, seeds, and fruits of the plant.

In one embodiment, the invention includes a modified Os08N3 EBE nucleic acid sequence of SEQ ID NOS: 44, 45, 46, or 47 which provides resistance to Xoo-mediated induction and bacterial blight, but which also maintains normal plant growth and development. SEQ ID NO:44 is a deletion of 6 nucleotides from wild type SEQ ID NO:44, 65 to 60 bases upstream of the transcription initiation site (bases 22 through 27 of SEQ ID NO:43); SEQ ID NO: 45 is a deletion of 8 nucleotides or bases 22-29 from wild type SEQ ID NO:43; SEQ ID NO: 46 is a deletion of 21 nucleotides or bases 16-36 from wild type SEQ ID NO:43 with the base at position 15 changed to a thymine from a cytosine in wild type SEQ ID NO:43; and SEQ ID NO: 47 is a deletion of 14 nucleotides or bases 16-30 from wild type SEQ ID NO:43.

In another embodiment, a nucleotide sequence that is at least 90 or greater, 95% or greater percent similar to SEQ ID NO: 44, 45, 46, or 47 which still inhibits AvrXa7 or PthXo3 induction yet retains normal plant development. In yet another embodiment, a nucleotide sequence that hybridizes to SEQ ID NO: 44, 45, 46, or 47 under stringent hybridization conditions involving, for example, hybridization in a hybridization buffer containing, for example, 20 percent formamide in 0.9M saline/0.09M SSC buffer, at a temperature of about 42° C. which still inhibits AvrXa7 or PthXo3 induction yet retains normal plant development are also within the scope of the invention. The invention also includes, plants, cells, seeds, plant tissues and the like which include this modification.

The present invention also relates to a method of imparting bacterial blight resistance to plants. This method involves providing a plant or plant seed comprising a modified EBE such as SEQ ID NO: 44, 45, 46, or 47 and growing the modified plant or a plant produced from the modified plant seed under conditions effective to impart resistance to the plant. The present invention further relates to plants produced by this method, as well as component parts, seeds, and fruits of the plant.

In addition the present invention is directed to transferring the modified EBEs disclosed herein to other plants, cultivars and species and is useful for producing cultivars and novel types with the Xoo resistance trait.

The invention also provides methods for introducing the modified EBEs of the present invention into plants by crossing a plant which lacks the modified EBE with a plant that has the modified EBE, selfing the resulting generations and then selecting the plants exhibiting bacterial blight tolerance.

In another aspect, the invention provides a method for producing a hybrid seed comprising crossing a first plant parent with a second plant parent and harvesting the resultant hybrid seed, wherein either one or both parents contain modified EBEs. The hybrid seeds, plant and parts thereof produced by such method are also part of the invention.

In another aspect, the present invention provides for further single gene converted plants with modified EBEs. The desired further single transferred gene may preferably be a dominant or recessive allele. Preferably, the further single transferred gene will confer such traits as herbicide resistance, insect resistance, resistance for bacterial, fungal, or viral disease, male fertility, male sterility, enhanced nutritional quality, and industrial usage. The single gene may be a naturally occurring gene or a transgene introduced through genetic engineering techniques.

In another aspect, the present invention provides regenerable cells for use in tissue culture of a plant containing a modified EBE. The tissue culture will preferably be capable of regenerating plants having the physiological and morphological characteristics of the foregoing plant, and of regenerating plants having substantially the same genotype as the foregoing plant. Preferably, the regenerable cells in such tissue cultures will be embryos, protoplasts, meristematic cells, callus, pollen, leaves, anthers, pistils, roots, root tips, flowers, seeds, panicles or stems. Still further, the present invention provides plants regenerated from the tissue cultures of the invention.

The present invention also relates to a method of making a bacterial blight resistant plant comprising introducing to said plant a mutation in the EBE region of a bacterial susceptibility gene of said plant. This can be accomplished by any methodology for generating mutations including site directed mutagenesis, optimized directed evolution, Gene Site-Saturation Mutagenesis (GSSM), synthetic ligation reassembly (SLR), error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, synthetic ligation reassembly (SLR) recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, introduction of a TALEN fusion protein, or other targeted mutagenesis techniques.

In one preferred embodiment, site directed mutagenesis is accomplished by use of TALENs. This methodology is disclosed in United States Published Application US 2011-0201118 A1 which is hereby incorporated by reference in its entirety, particularly page 50, line 14-page 58, line 4 and FIGS. 1-3 and page 64, line 2-page 66, line 29 and FIGS. 10-16. Applicants have generated a TAL nuclease, a hybrid protein derived from FokI and AvrXa7, a member of transcription activator-like (TAL) effector family from phytopathogenic bacteria. The hybrid protein, referred to as TALEN, retains both recognition specificity for the EBE and the double-stranded DNA cleaving activity of FokI. The TALEN cleaves DNA adjacent to the AvrXa7-binding site under optimal conditions in vitro and when expressed promotes the DNA homologous recombination or paired target sequences.

Thus the invention comprises a method of introducing bacterial blight resistance to a cell by modifying the genetic material of a cell. The method includes providing a primary cell containing a chromosomal target DNA sequence (EBE) in which it is desired to have homologous recombination occur; providing a TAL effector endonuclease comprising an endonuclease domain that can cleave double stranded DNA, and a TAL effector domain comprising a plurality of TAL effector repeat sequences that, in combination, bind to a specific nucleotide sequence within the target DNA in the cell; and contacting the target DNA sequence with the TAL effector endonuclease in the cell such that the TAL effector endonuclease cleaves both strands of a nucleotide sequence within or adjacent to the target DNA sequence in the cell. The method can further include providing a nucleic acid comprising a sequence homologous to at least a portion of the target DNA, such that homologous recombination occurs between the target DNA sequence and the nucleic acid. The target DNA sequence is an endogenous EBE sequence that is endogenous to the cell and which provides for inhibition of induction, yet normal plant development. The contacting can include transfecting the cell with a vector comprising a TAL effector endonuclease coding sequence, and expressing the TAL effector endonuclease protein in the cell, mechanically injecting a TAL effector endonuclease protein into the cell, delivering a TAL effector endonuclease protein into the cell by means of the bacterial type III secretion system, or introducing a TAL effector endonuclease protein into the cell by electroporation. The endonuclease domain can be from a type II restriction endonuclease (e.g., FokI). The TAL effector domain that binds to a specific nucleotide sequence within the target DNA can include 15 or more DNA binding repeats.

In another embodiment the invention includes a method for designing a sequence specific TAL effector endonuclease capable of cleaving endogenous EBE DNA at a specific location. The method includes identifying a first unique endogenous chromosomal nucleotide sequence adjacent to a second nucleotide sequence (EBE) at which it is desired to introduce a double-stranded cut; and designing a sequence specific TAL effector endonuclease comprising (a) a plurality of DNA binding repeat domains that, in combination, bind to the first unique endogenous chromosomal nucleotide sequence, and (b) an endonuclease that generates a double-stranded cut and hence a mutation in the EBE site at the second nucleotide sequence.

According to the invention, the fusion protein can be expressed in a cell, e.g., by delivering the fusion protein to the cell or by delivering a polynucleotide encoding the fusion protein to a cell, wherein the polynucleotide, if DNA, is transcribed, and an RNA molecule delivered to the cell or a transcript of a DNA molecule delivered to the cell is translated, to generate the fusion protein. Methods for polynucleotide and polypeptide delivery to cells are known in the art and are presented elsewhere in this disclosure.

Targeted mutations in the EBE region resulting from the aforementioned method include, but are not limited to, point mutations (i.e., conversion of a single base pair to a different base pair), substitutions (i.e., conversion of a plurality of base pairs to a different sequence of identical length), insertions or one or more base pairs, deletions of one or more base pairs and any combination of the aforementioned sequence alterations.

The invention also includes a TAL effector endonuclease comprising an endonuclease domain and a TAL effector DNA binding domain specific for a particular DNA sequence. The TAL effector endonuclease (TALEN) can further include a purification tag. The endonuclease domain can be from a type II restriction endonuclease (e.g., FokI).

The invention also includes novel nucleic acid sequence encoding TALEN fusion proteins which have been designed to interact and cleave the target EBE sequences. In one embodiment the TALEN includes one or more of SEQ ID NOS 21 (dTALENR1) 22 (dTALENR2), and 23 (dTALENL1) operably linked to a promoter sequence to generate site directed nuclease fusions and mutant EBE recognition sites. In another embodiment, the TALEN includes one or more of SEQ ID NO:36 and 38 operably linked to a promoter sequence to generate site directed nuclease fusions and mutant EBE recognition sites. The method involves growing a host cell containing the nucleic acid molecules under conditions whereby the host cell expresses the same and nuclease fusion is conducted. Expression constructs comprising the nucleotide sequences encoding the fusion TALEN proteins operably linked to regulatory elements, vectors, and genetically modified plant cells expression the fusion proteins, and thus the resultant EBE modification are also included in the invention.

The invention further includes introducing the amino acid sequences of designed TALEN fusion proteins listed above as well as all conservatively modified variants, including SEQ ID NO:24, 25, 26, 37, and 39.

In another aspect of the invention, the invention comprises a method for producing a genetically modified plant that has improved tolerance to bacterial blight comprising the steps of: a) introducing into a plant seed, plant tissue or plant cell the TALEN expression construct as described above to produce a transformed plant seed, plant tissue or plant cell; and b) regenerating a transgenic plant from the transformed plant seed, transformed plant tissue or transformed plant cell, wherein the transgenic plant has improved tolerance to Xoo, or bacterial blight compared to a non-modified plant. In one embodiment, the transgenic plant is a rice plant.

In another aspect of the invention, the invention comprises an immunoassay method to detect Xoo susceptibility in plants by screening the same for a TALEN fusion protein in said plant.

The invention further provides plants, seeds, and other plant parts such as pollen and ovules containing the modified EBE sequences, the TALEN fusion proteins, or the expression constructs encoding the TALEN fusion proteins disclosed herein.

In addition to the exemplary aspects and embodiments described above, further aspects and embodiments will become apparent by study of the following descriptions.

FIG. 3 is a schematic of two gene expression cassettes in a single binary vector for rice transformation. The expression cassette includes a promoter [maize ubiquitin 1 promoter (Ubi1) and the cauliflower mosaic virus 35S gene promoter (35S)] (red arrow) and a terminator (Nos-T) (black bar) with the nuclease gene (TALEN-L and TALEN-R, respectively) (open box) inserted between.

FIG. 4 shows the sequences of Os11N3 mutations induced by the Pair 2 nucleases. Deletions and insertions are indicated by dashes and red letters, respectively. Number of nucleotide changes is indicated on the right side of sequence. TALEN-binding sequences are underlined. (SEQ ID NOS 1, 10, 11, 12, 13, 14, and 15 respectively)

FIG. 5 shows the TALENs for targeted editing of the promoter of Os8N3. A. The sucrose efflux transporter gene 11 (also called OsSWEET11) contains a PthXo1 binding site (shaded in grey). (A) pair of TALENs (SWT11-TALEN-L and -R) bind to the promoter of Os8N3 (underlined sequences with the L site starting at 86 bp upstream of the transcription initiation site). (SEQ ID NOS 36 and 38) (B) RVD sequences within the repeat domains of the paired TALENs and the corresponding EBEs. "*" represents the $13^{th}$ amino acid missing in the last half repeat of the dTALENs. (SEQ ID NOS 37 and 39).

Figure 6A:
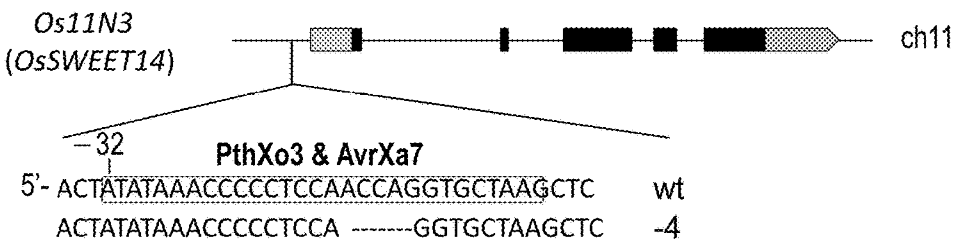

FIG. 6 shows how TALENs induce precise mutations at the PthXo1 binding site in the promoter of Os8N3 in rice. (A) Genotype of rice plant used for the second round of gene editing. The plants already contain a 4-bp deletion within the overlapping binding sites (shaded in grey, starting 32 bp upstream of the transcription initiation site of Os11N) by AvrXa7 and SPthXo3. (SEQ ID NOS 43 and 48) (B) Sequences of four representative OsN3 mutations induced by the TALENs with deletions (dashes) and insertion (red). TALEN binding sites are underlined and PthXo1 binding sequences are shaded in grey in wild type (wt). Number at the right side denotes the base pair deleted compared to wt. (SEQ ID NOS 44-48)

Figure 7A:
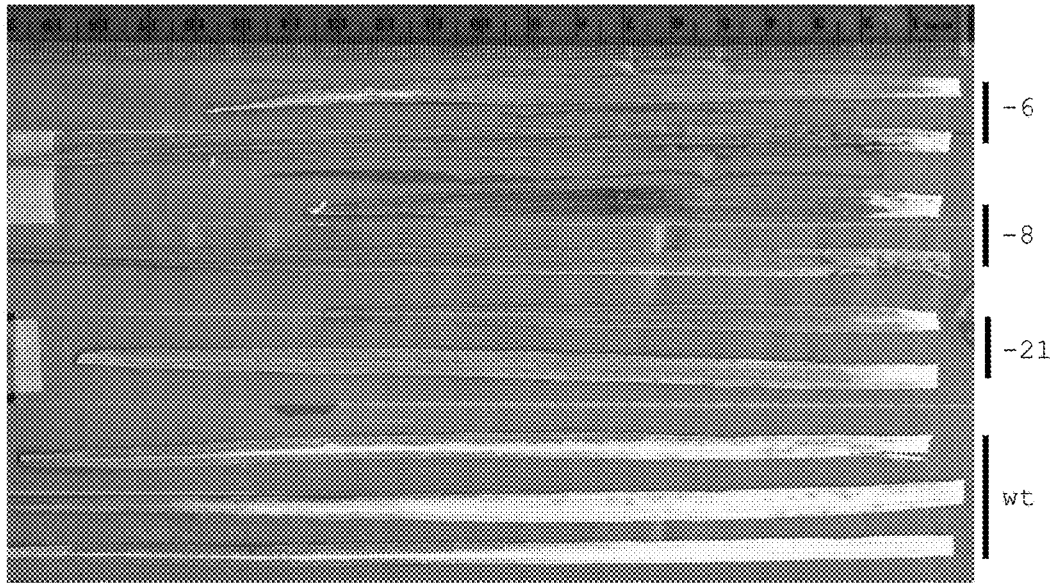

FIG. 7 shows disease resistance in transgenic rice T1 plants. (A) Resistance phenotype displayed by three T1 homozygous mutant plants compared to the susceptible phenotype of three plants homozygous for wild type Os8N3. The plants were inoculated with the pathogenic PXO99 that is dependent on PthXo1 to cause blight disease. (B) Lesion lengths caused by infection with the pathogenic PthXo1-dependent Xoo strain PXO99 strain were measured 14 days after inoculation of multiple plants (4-6 plants) homozygous for individual mutations or wild type segregated from individual mutant lines. The genotypes of the individually inoculated plants were confirmed by genotyping through sequencing. Leaf lesion lengths <5 cm indicate disease resistance and lesion lengths >10 indicate disease susceptibility. Error bars indicate 1 SD.

FIG. 8 shows sequences of the ORFs and the corresponding amino acid sequences of dTALENs (SEQ ID NOS:21-26).

FIG. 9 shows the sequences of the ORFs and the corresponding amino acid sequences of SWT11-TALEN-L and SWT11-TALEN-R (SEQ ID NOS:36-39).

DETAILED DESCRIPTION OF THE INVENTION

General

In order to provide a clear and consistent understanding of the specification and the claims, including the scope given to such terms, the following definitions are provided. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNABinding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may affect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, "vector" includes reference to a nucleic acid used in transfection of a host cell and into which can be inserted a polynucleotide. Vectors are often replicons. Expression vectors permit transcription of a nucleic acid inserted therein.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "TAL effector DNA binding protein" (or binding domain) or a "TAL effector DNA recognition sequence" is a protein encompassing a series of repeat variable-diresidues (RVDs) within a larger protein, that binds DNA in a sequence-specific manner. The RVD regions of TAL effectors are polymorphisms within TALs typically at positions 12 and 13 in repeating units of typically 34 amino acids that bind for specific nucleotides and together with a plurality of repeating unit intervals make up the specific TAL effector DNA binding domain.

TAL effector DNA binding protein domains (their RVDs) can be "engineered" to bind to a predetermined nucleotide sequence. Non-limiting examples of methods for engineering the same are design and selection. A designed TAL effector DNA binding protein is a protein not occurring in nature whose design/composition results principally from rational criteria. Rational criteria for design include application of substitution rules and computerized algorithms for processing information in a database storing information of existing RVD designs and binding data.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value there between or there above), preferably between about 100 and 1,000 nucleotides in length (or any integer there between), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination there between, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotideto-nucleotide or amino acid-to-amino acid correspondence of two polynucleotides or polypeptide sequences, respectively.

Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: www.ncbi.nlm.gov. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; Nucleic Acid Hybridization: A Practical Approach, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule Inhibition of hybridization of the completely identical sequence can be assessed using hybridization assays that are well known in the art (e.g., Southern (DNA) blot, Northern (RNA) blot, solution hybridization, or the like, see Sambrook, et al., Molecular Cloning: A Laboratory Manual, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, Nucleic Acid Hybridization: A Practical Approach, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., Molecular Cloning: A Laboratory Manual, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

A "heterologous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

A heterologous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

A heterologous molecule can be the same type of molecule as an endogenous molecule, e.g., a heterologous protein or nucleic acid. For example, a heterologous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a TAL effector sequence DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

The invention includes plants with plant susceptibility genes that have been modified in the EBE region. This can include modified Os11N3 EBE nucleic acid sequences SEQ ID NOS: 5, 6, 7, 9, 44, 45, 46, or 47 which provide resistance to Xoo-mediated induction and bacterial blight, but which also maintain normal plant growth and development. In another embodiment, a nucleotide sequence that is at least 90 or greater, 95% or greater percent similar to SEQ ID NO: 5, 6, 7, or 9 which still inhibits AvrXa7 or PthXo3 induction yet retains normal plant development. In another embodiment, a nucleotide sequence that is at least 90 or greater, 95% or greater percent similar to SEQ ID NO: 44, 45, 46, or 47 which still inhibits PthXo1 induction yet retains normal plant development. In yet another embodiment, a nucleotide sequence that hybridizes to SEQ ID NO 5, 6, 7, or 9 under stringent hybridization conditions involving, for example, hybridization in a hybridization buffer containing, for example, 20 percent formamide in 0.9M saline/0.09M SSC buffer, at a temperature of about 42° C. which still inhibits AvrXa7 or PthXo3 induction yet retains normal plant development are within the scope of the invention. In yet another embodiment, a nucleotide sequence that hybridizes to SEQ ID NO 44, 45, 46, or 47 under stringent hybridization conditions involving, for example, hybridization in a hybridization buffer containing, for example, 20 percent formamide in 0.9M saline/0.09M SSC buffer, at a temperature of about 42° C. which still inhibits PthXo1 induction yet retains normal plant development are also within the scope of the invention.

Bacterial blight resistance plants may be obtained by incorporating the modified EBE regions of the invention into a plant. This may be accomplished by back crossing and standard breeding techniques or by site directed mutagenesis techniques. One particularly preferred site directed mutagenesis technique is via TALE nucleases (TALENs), the hybrid proteins of native or customized TAL effectors and the DNA cleavage domains such as FokI, using TALENs to mutate S gene EBEs in a way the renders it no longer responsive to the cognate TAL effector and, thus, confers resistance to bacterial blight.

EBE Target Sites

The disclosed methods and compositions of the invention include specific target sites on EBE regions that may be modified according to the invention to impart disease resistance while still retaining plant growth and function. In the TAL effector site directed mutagenesis embodiment, the invention includes fusion proteins such as SEQ ID NOS 24, 25, 26, 37 or 39 comprising a cleavage domain and a TAL effector DNA binding domain, or DNA recognition sequence in which the RVDs, by binding to a sequence in cellular chromatin (e.g., a target site or a binding site), directs the activity of the cleavage domain (or cleavage half-domain) to the vicinity of the sequence and, hence, induces cleavage in the vicinity of the target sequence, here the EBE site. As set forth elsewhere in this disclosure, Particular RVDs within a TAL binding domain can be engineered to bind to virtually any desired sequence and here are engineered to bind to EBE sites. Accordingly, after identifying a region of interest containing a sequence at which cleavage or recombination is desired, one or more TAL effector DNA binding domains can be engineered to bind to one or more sequences in the region of interest. Expression of a fusion protein comprising a TAL effector DNA binding domain and a cleavage domain, in a cell, effects cleavage in the region of interest.

Selection of a sequence in cellular chromatin for binding by a TAL effector binding domain (e.g., a target site) may be determined by identifying EBE sites within susceptibility genes for bacterial pathogens that are upregulated or otherwise modified by bacterial pathogen infection.

Sequence-Specific Endonucleases

Sequence-specific nucleases such as SEQ ID NOS 24, 25, 26, 37 and 39 and recombinant nucleic acids encoding the sequence-specific endonucleases SEQ ID NOS: 21, 22, 23, 36 and 38 are provided herein. The sequence-specific endonucleases can include TAL effector DNA binding domains and endonuclease domains. Thus, nucleic acids encoding such sequence-specific endonucleases can include a nucleotide sequence from a sequence-specific TAL effector linked to a nucleotide sequence from a nuclease.

TAL effectors are proteins of plant pathogenic bacteria that are injected by the pathogen into the plant cell, where they travel to the nucleus and function as transcription factors to turn on specific plant genes. The primary amino acid sequence of a TAL effector dictates the nucleotide sequence to which it binds. Because the relationship between the TAL amino acid sequence and the target binding site is simple, target sites can be predicted for TAL effectors, and TAL effectors also can be engineered and generated for the purpose of binding to particular nucleotide sequences.

Fused to the TAL effector-encoding nucleic acid sequences are sequences encoding a nuclease or a portion of a nuclease, typically a nonspecific cleavage domain from a type II restriction endonuclease such as FokI (Kim et al. (1996) *Proc. Natl. Acad Sci. USA* 93:1156-1160). Other useful endonucleases may include, for example, HhaI, HindIII, NotI, BbvC1, EcoRI, BglI, and AlwI. The fact that some endonucleases (e.g., FokI) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created.

A sequence-specific TAL effector endonuclease as provided herein can recognize a particular sequence within a preselected target nucleotide sequence present in a cell. Thus, in some embodiments, a target nucleotide sequence can be scanned for nuclease recognition sites, and a particular nuclease can be selected based on the target sequence. In other cases, a TAL effector endonuclease can be engineered to target a particular cellular sequence. A nucleotide sequence encoding the desired TAL effector endonuclease can be inserted into any suitable expression vector, and can be linked to one or more expression control sequences. For example, a nuclease coding sequence can be operably linked to a promoter sequence that will lead to constitutive expression of the endonuclease in the species of plant to be transformed. Alternatively, an endonuclease coding sequence can be operably linked to a promoter sequence that will lead to conditional expression (e.g., expression under certain nutritional conditions).

Cleavage Domains

The cleavage domain portion of the fusion proteins disclosed herein can be obtained from any endo- or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one embodiment, fusion proteins comprise the cleavage domain (or cleavage half-domain) from at least one Type IIS restriction enzyme.

An exemplary Type IIS restriction enzyme, whose cleavage domain is separable from the binding domain, is FokI. This particular enzyme is active as a dimer. Bitinaite et al. (1998) Proc. Natl. Acad. Sci. USA 95: 10,570-10,575.

Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using TAL-FokI fusions, two fusion proteins, each comprising a FokI cleavage half-domain, can be used to reconstitute a catalytically active cleavage domain. Parameters for targeted cleavage and targeted sequence alteration using TAL-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Additional restriction enzymes also contain separable binding and cleavage domains, and these are contemplated by the present disclosure. See, for example, Roberts et al. (2003) Nucleic Acids Res. 31:418-420. Examples of Type IIS Restriction Enzymes include: Aar I, BsrB I, SspD5 I, Ace III, BsrD I, Sth132 I, Aci I, BstF5 I, Sts I, Alo I, Btr I, TspDT I, Bae I, Bts I, TspGW I, Bbr7 I, Cdi I, Tth111 II, Bbv I, CjeP I, UbaP I, Bbv II, Drd II, Bsa I, BbvC I, Eci I, BsmB I, Bcc I, Eco3I, Bce83 I, Eco57 I, BceA I, Eco57M I, Bcef I, Esp3 I, Bcg I, Fau I, BciV I, Fin I, Bfi I, Fok I, Bin I, Gdi II, Bmg I, Gsu I, Bpu10 I, Hga I, BsaX I, Hin4 II, Bsb I, Hph I, BscA I, Ksp632 I, BscG I, Mbo II, BseR I, Mly I, BseY I, Mme I, Bsi I, Mnl I, Bsm I, Pfl1108 I, BsmA I, Ple I, BsmF I, Ppi I, Bsp24 I, Psr I, BspG I, RleA I, BspM I, Sap I, BspNC I, SfaN I, Bsr I, and Sim I TAL Effector DNA Domain-Cleavage Domain Fusions Methods for design and construction of fusion proteins (and polynucleotides encoding same) are known to those of skill in the art. For example, methods for the design and construction of fusion protein comprising TAL proteins (and polynucleotides encoding same) are described in U.S. Pat. Nos. 6,453,242 and 6,534,261. In certain embodiments, polynucleotides encoding such fusion proteins are constructed. These polynucleotides can be inserted into a vector and the vector can be introduced into a cell (see below for additional disclosure regarding vectors and methods for introducing polynucleotides into cells).

In certain embodiments of the methods described herein, a fusion protein comprises the overlapping a TAL effector binding domain from AvrXa7 and PthXo3 (SEQ ID NO:20) and a cleavage half-domain from the FokI restriction enzyme, and two such fusion proteins are expressed in a cell. Expression of two fusion proteins in a cell can result from delivery of the two proteins to the cell; delivery of one protein and one nucleic acid encoding one of the proteins to the cell; delivery of two nucleic acids, each encoding one of the proteins, to the cell; or by delivery of a single nucleic acid, encoding both proteins, to the cell. In additional embodiments, a fusion protein comprises a single polypeptide chain comprising two cleavage half domains and the overlapping TAL AvrXa7 and PthXo3 (SEQ ID NO:20) binding domain. In this case, a single fusion protein is expressed in a cell and, without wishing to be bound by theory, is believed to cleave DNA as a result of formation of an intramolecular dimer of the cleavage half-domains.

In certain embodiments, the components of the fusion proteins (e.g, TAL-FokI fusions) are arranged such that the cleavage domain is nearest the amino terminus of the fusion protein, and the TAL domain is nearest the carboxy-terminus. This provides certain advantages such as the retention of the transcription activator activity which enables one to measure the DNA binding specificity of naturally occurring TAL or newly engineered TAL used for nuclease fusion and this orientation may give the flexibility of spacer lengths.

Methods for Targeted Cleavage

The disclosed methods and compositions can be used to cleave DNA at an EBE in cellular chromatin (e.g., at a desired or predetermined site in a genome, for example, in a gene, either mutant or wild-type). For such targeted DNA cleavage, TAL binding domain is engineered to bind a target site at or near the predetermined EBE cleavage site, and a fusion protein comprising the engineered TAL binding domain and a cleavage domain is expressed in a cell. Upon binding of the TAL RVDs portion of the fusion protein to the target site, the DNA is cleaved near the target site by the cleavage domain.

For targeted cleavage using a TAL binding domain-cleavage domain fusion polypeptide, the binding site can encompass the cleavage site, or the near edge of the binding site can be 1, 2, 3, 4, 5, 6, 10, 25, 50 or more nucleotides (or any integral value between 1 and 50 nucleotides) from the cleavage site. The exact location of the binding site, with respect to the cleavage site, will depend upon the particular cleavage domain, and the length of any linker.

Thus, the methods described herein can employ an engineered TAL effector DNA binding domain fused to a cleavage domain. In these cases, the binding domain is engineered to bind to a target sequence, at or near which cleavage is desired. The fusion protein, or a polynucleotide encoding same, is introduced into a cell. Once introduced into, or expressed in, the cell, the fusion protein binds to the target sequence and cleaves at or near the target sequence. The exact site of cleavage depends on the nature of the cleavage domain and/or the presence and/or nature of linker sequences between the binding and cleavage domains. Optimal levels of cleavage can also depend on both the distance between the binding sites of the two fusion proteins (See, for example, Smith et al. (2000) Nucleic Acids Res. 28:3361-3369; Bibikova et al. (2001) Mol. Cell. Biol. 21:289-297) and the length of the ZC linker in each fusion protein.

In certain embodiments, the cleavage domain comprises two cleavage half-domains, both of which are part of a single polypeptide comprising a binding domain, a first cleavage half-domain and a second cleavage half-domain. The cleavage half-domains can have the same amino acid sequence or different amino acid sequences, so long as they function to cleave the DNA.

Cleavage half-domains may also be provided in separate molecules. For example, two fusion polypeptides may be introduced into a cell, wherein each polypeptide comprises a binding domain and a cleavage half-domain. The cleavage half-domains can have the same amino acid sequence or different amino acid sequences, so long as they function to cleave the DNA. Further, the binding domains bind to target sequences which are typically disposed in such a way that, upon binding of the fusion polypeptides, the two cleavage half-domains are presented in a spatial orientation to each other that allows reconstitution of a cleavage domain (e.g., by dimerization of the half-domains), thereby positioning the half-domains relative to each other to form a functional cleavage domain, resulting in cleavage of cellular chromatin in a region of interest. Generally, cleavage by the reconstituted cleavage domain occurs at a site located between the two target sequences. One or both of the proteins can be engineered to bind to its target site.

The two fusion proteins can bind in the region of interest in the same or opposite polarity, and their binding sites (i.e., target sites) can be separated by any number of nucleotides, e.g., from 0 to 200 nucleotides or any integral value therebetween. In certain embodiments, the binding sites for two fusion proteins, each comprising a TAL effector binding domain and a cleavage half-domain, can be located between 5 and 18 nucleotides apart, for example, 5-8 nucleotides apart, or 15-18 nucleotides apart, or 6 nucleotides apart, or 16 nucleotides apart, as measured from the edge of each binding site nearest the other binding site, and cleavage occurs between the binding sites.

The site at which the DNA is cleaved generally lies between the binding sites for the two fusion proteins. Double-strand breakage of DNA often results from two single-strand breaks, or "nicks," offset by 1, 2, 3, 4, 5, 6 or more nucleotides, (for example, cleavage of double-stranded DNA by native FokI results from single-strand breaks offset by 4 nucleotides). Thus, cleavage does not necessarily occur at exactly opposite sites on each DNA strand. In addition, the structure of the fusion proteins and the distance between the target sites can influence whether cleavage occurs adjacent a single nucleotide pair, or whether cleavage occurs at several sites. However, for many applications, including targeted recombination and targeted mutagenesis (see infra) cleavage within a range of nucleotides is generally sufficient, and cleavage between particular base pairs is not required.

As noted above, the fusion protein(s) can be introduced as polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides is introduced into a cell. Polynucleotides can be DNA, RNA or any modified forms or analogues or DNA and/or RNA.

In addition to the fusion molecules described herein, targeted replacement of a selected genomic sequence also requires the introduction of the replacement (or donor) sequence. The donor sequence can be introduced into the cell prior to, concurrently with, or subsequent to, expression of the fusion protein(s). The donor polynucleotide contains sufficient homology to a genomic sequence to support homologous recombination between it and the genomic sequence to which it bears homology. Approximately 25, 50, 100 or 200 nucleotides or more of sequence homology between a donor and a genomic sequence (or any integral value between 10 and 200 nucleotides, or more) will support homologous recombination therebetween. Donor sequences can range in length from 10 to 5,000 nucleotides (or any integral value of nucleotides therebetween) or longer. It will be readily apparent that the donor sequence is typically not identical to the genomic sequence that it replaces. For example, the sequence of the donor polynucleotide can contain one or more single base changes, insertions, deletions, inversions or rearrangements with respect to the genomic sequence, so long as sufficient homology is present to support homologous recombination. Alternatively, a donor sequence can contain a non-homologous sequence flanked by two regions of homology. Additionally, donor sequences can comprise a vector molecule containing sequences that are not homologous to the region of interest in cellular chromatin. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

To simplify assays (e.g., hybridization, PCR, restriction enzyme digestion) for determining successful insertion of the donor sequence, certain sequence differences may be present in the donor sequence as compared to the genomic sequence. Preferably, if located in a coding region, such nucleotide sequence differences will not change the amino acid sequence, or will make silent amino acid changes (i.e., changes which do not affect the structure or function of the protein). The donor polynucleotide can optionally contain changes in sequences corresponding to the TAL effector domain binding (or recognition) sites in the region of interest, to prevent cleavage of donor sequences that have been introduced into cellular chromatin by homologous recombination.

The donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV).

Without being bound by one theory, it appears that the presence of a double-stranded break in a cellular sequence, coupled with the presence of an exogenous DNA molecule having homology to a region adjacent to or surrounding the break, activates cellular mechanisms which repair the break by transfer of sequence information from the donor molecule into the cellular (e.g., genomic or chromosomal) sequence; i.e., by a processes of homologous recombination. Applicants' methods advantageously combine the powerful targeting capabilities of engineered TALs with a cleavage domain (or cleavage half-domain) to specifically target a double-stranded break to the region of the genome at which recombination is desired.

For alteration of a chromosomal sequence, it is not necessary for the entire sequence of the donor to be copied into the chromosome, as long as enough of the donor sequence is copied to effect the desired sequence alteration.

Expression Vectors

A nucleic acid encoding one or more fusion proteins can be cloned into a vector for transformation into prokaryotic or eukaryotic cells for replication and/or expression. Vectors can be prokaryotic vectors, e.g., plasmids, or shuttle vectors, insect vectors, or eukaryotic vectors. A nucleic acid encoding a TAL effector binding domain can also be cloned into an expression vector, for administration to a plant cell, animal cell, preferably a mammalian cell or a human cell, fungal cell, bacterial cell, or protozoal cell.

To obtain expression of a cloned gene or nucleic acid, sequences encoding a fusion protein are typically subcloned into an expression vector that contains a promoter to direct transcription.

Promoters are involved in recognition and binding of RNA polymerase and other proteins to initiate and modulate transcription. To bring a coding sequence under the control of a promoter, it typically is necessary to position the translation initiation site of the translational reading frame of the polypeptide between one and about fifty nucleotides downstream of the promoter. A promoter can, however, be positioned as much as about 5,000 nucleotides upstream of the translation start site, or about 2,000 nucleotides upstream of the transcription start site. A promoter typically comprises at least a core (basal) promoter. A promoter also may include at least one control element such as an upstream element. Such elements include upstream activation regions (UARs) and, optionally, other DNA sequences that affect transcription of a polynucleotide such as a synthetic upstream element.

The choice of promoters to be included depends upon several factors, including, but not limited to, efficiency, selectability, inducibility, desired expression level, and cell or tissue specificity. For example, tissue-, organ- and cell-specific promoters that confer transcription only or predominantly in a particular tissue, organ, and cell type, respectively, can be used. In some embodiments, promoters specific to vegetative tissues such as the stem, parenchyma, ground meristem, vascular bundle, cambium, phloem, cortex, shoot apical meristem, lateral shoot meristem, root apical meristem, lateral root meristem, leaf primordium, leaf mesophyll, or leaf epidermis can be suitable regulatory regions. In some embodiments, promoters that are essentially specific to seeds ("seed-preferential promoters") can be useful. Seed-specific promoters can promote transcription of an operably linked nucleic acid in endosperm and cotyledon tissue during seed development. Alternatively, constitutive promoters can promote transcription of an operably linked nucleic acid in most or all tissues of a plant, throughout plant development. Other classes of promoters include, but are not limited to, inducible promoters, such as promoters that confer transcription in response to external stimuli such as chemical agents, developmental stimuli, or environmental stimuli.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

Non-limiting examples of promoters that can be included in the nucleic acid constructs provided herein include the cauliflower mosaic virus (CaMV) 35S transcription initiation region, the 1' or 2' promoters derived from T-DNA of *Agrobacterium tumefaciens*, promoters from a maize leaf-specific gene described by Busk ((1997) *Plant J* 11:1285-1295), kn1-related genes from maize and other species, and transcription initiation regions from various plant genes such as the maize ubiquitin-1 promoter.

A 5' untranslated region (UTR) is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA message stability or translation attenuation. Examples of 3' UTRs include, but are not limited to polyadenylation signals and transcription termination sequences. A polyadenylation region at the 3'-end of a coding region can also be operably linked to a coding sequence. The polyadenylation region can be derived from the natural gene, from various other plant genes, or from an *Agrobacterium* T-DNA.

The vectors provided herein also can include, for example, origins of replication, and/or scaffold attachment regions (SARs). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag" tag (Kodak, New Haven, Conn.) sequences typically are expressed as a fusion with the encoded polypeptide. Such tags can be inserted anywhere within the polypeptide, including at either the carboxyl or amino terminus.

It will be understood that more than one regulatory region may be present in a recombinant polynucleotide, e.g., introns, enhancers, upstream activation regions, and inducible elements.

Recombinant nucleic acid constructs can include a polynucleotide sequence inserted into a vector suitable for transformation of cells (e.g., plant cells or animal cells). Recombinant vectors can be made using, for example, standard recombinant DNA techniques (see, e.g., Sambrook et al. (1989) *Molecular Cloning: A Laboratory Manual,* 2nd ed., Cold Spring Harbor Laboratory, Cold Spring Harbor, N.Y.).

Suitable bacterial and eukaryotic promoters are well known in the art and described, e.g., in Sambrook et al., Molecular Cloning, A Laboratory Manual (2nd ed. 1989; 3rd ed., 2001); Kriegler, Gene Transfer and Expression: A Laboratory Manual (1990); and Current Protocols in Molecular Biology (Ausubel et al., supra. Bacterial expression systems for expressing the ZFP are available in, e.g., *E. coli, Bacillus* sp., and *Salmonella* (Palva et al., Gene 22:229-235 (1983)). Kits for such expression systems are commercially available. Eukaryotic expression systems for mammalian cells, yeast, and insect cells are well known by those of skill in the art and are also commercially available.

The promoter used to direct expression of a TAL-cleavage domain fusion protein-encoding nucleic acid depends on the particular application. For example, a strong constitutive promoter is typically used for expression and purification of TAL-cleavage domain fusion proteins. In contrast, when a TAL-cleavage domain fusion protein is administered in vivo for gene regulation, either a constitutive or an inducible promoter is used, depending on the particular use of the TAL-cleavage domain fusion protein. In addition, a preferred promoter for administration of a TAL-cleavage domain fusion protein can be a weak promoter, such as HSV TK or a promoter having similar activity. The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard, PNAS 89:5547 (1992); Oligino et al., Gene Ther. 5:491-496 (1998); Wang et al., Gene Ther. 4:432-441 (1997); Neering et al., Blood 88:1147-1155 (1996); and Rendahl et al., Nat. Biotechnol. 16:757-761 (1998)). The MNDU3 promoter can also be used, and is preferentially active in CD34+ hematopoietic stem cells.

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to a nucleic acid sequence encoding the TAL-cleavage domain fusion protein and signals required, e.g., for efficient polyadenylation of the transcript, transcriptional termination, ribosome binding sites, or translation termination. Additional elements of the cassette may include, e.g., enhancers, and heterologous splicing signals.

The particular expression vector used to transport the genetic information into the cell is selected with regard to the intended use of the TAL-cleavage domain fusion protein, e.g., expression in plants, animals, bacteria, fungus, protozoa, etc. (see expression vectors described below). Standard bacterial expression vectors include plasmids such as pBR322-based plasmids, pSKF, pET23D, and commercially available fusion expression systems such as GST and LacZ. An exemplary fusion protein is the maltose binding protein, “MBP.” Such fusion proteins are used for purification of the TAL-cleavage domain fusion protein. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with a TAL-cleavage domain fusion protein encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce plant, bacterial, mammalian, yeast or insect cell lines that express large quantities of protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983).

Any of the well-known procedures for introducing foreign nucleotide sequences into host cells may be used. These include the use of calcium phosphate transfection, polybrene, protoplast fusion, electroporation, ultrasonic methods (e.g., sonoporation), liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Nucleic Acids Encoding Fusion Proteins and Delivery to Cells

Conventional viral and non-viral based gene transfer methods can be used to introduce nucleic acids encoding engineered TAL-cleavage domain fusion proteins in animal cells (e.g., mammalian cells) and target tissues. Such methods can also be used to administer nucleic acids encoding TAL-cleavage domain fusion proteins to cells in vitro. In certain embodiments, nucleic acids encoding TAL-cleavage domain fusion proteins are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1: 13-26 (1994).

Methods of non-viral delivery of nucleic acids encoding engineered TAL-cleavage domain fusion proteins include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.) and BTX Molecular Delivery Systems (Holliston, Mass.).

The use of RNA or DNA viral based systems for the delivery of nucleic acids encoding engineered TAL-cleavage domain fusion proteins take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of TAL-cleavage domain fusion proteins include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene.

Additionally, high transduction efficiencies have been observed in many different cell types and target tissues.

In applications in which transient expression of a TAL-cleavage domain fusion protein fusion protein is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., Hum. Gene Ther. 7:1083-9 (1998)). Additional examples of the use of adenovirus vectors for gene transfer in clinical trials include Rosenecker et al., Infection 24:1 5-10 (1996); Sterman et al., Hum. Gene Ther. 9:7 1083-1089 (1998); Welsh et al., Hum. Gene Ther. 2:205-18 (1995); Alvarez et al., Hum. Gene Ther. 5:597-613 (1997); Topf et al., Gene Ther. 5:507-513 (1998); Sterman et al., Hum. Gene Ther. 7:1083-1089 (1998).

Packaging cells are used to form virus particles that are capable of infecting a host cell. Such cells include 293 cells, which package adenovirus, and .psi.2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., Proc. Natl. Acad. Sci. USA 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., Culture of Animal Cells, A Manual of Basic Technique (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-$\gamma$ and TNF-$\alpha$ are known (see Inaba et al., J. Exp. Med. 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and lad (differentiated antigen presenting cells) (see Inaba et al., J. Exp. Med. 176:1693-1702 (1992)).

Vectors (e.g., retroviruses, adenoviruses, liposomes, etc.) containing therapeutic TAL-cleavage domain fusion protein nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

With further respect to plants, the polynucleotides and vectors described herein can be used to transform a number of monocotyledonous and dicotyledonous plants and plant cell systems, including dicots such as safflower, alfalfa, soybean, coffee, amaranth, rapeseed (high erucic acid and canola), peanut or sunflower, as well as monocots such as oil palm, sugarcane, banana, sudangrass, com, wheat, rye, barley, oat, rice, millet, or sorghum. Also suitable are gymnosperms such as fir and pine.

Thus, the methods described herein can be utilized with dicotyledonous plants belonging, for example, to the orders Magniolales, Illiciales, Laurales, Piperales, Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violates, Salicales, Capparales, Ericales, Diapensales, Ebenales, Primulales, Rosales, Fabales, Podostemales, Haloragales, Myrtales, Cornales, Proteales, San tales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. The methods described herein also can be utilized with monocotyledonous plants such as those belonging to the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchid ales, or with plants belonging to Gymnospermae, e.g., Pinales, Ginkgoales, Cycadales and Gnetales.

The methods can be used over a broad range of plant species, including species from the dicot genera *Atropa, Alseodaphne, Anacardium, Arachis, Beilschmiedia, Brassica, Carthamus, Cocculus, Croton, Cucumis, Citrus, Citrullus, Capsicum, Catharanthus, Cocos, Coffea, Cucurbita, Daucus, Duguetia, Eschscholzia, Ficus, Fragaria, Glaucium, Glycine, Gossypium, Helianthus, Hevea, Hyoscyamus, Lactuca, Landolphia, Linum, Litsea, Lycopersicon, Lupinus, Manihot, Majorana, Malus, Medicago, Nicotiana, Olea, Parthenium, Papaver, Persea, Phaseolus, Pistacia, Pisum, Pyrus, Prunus, Raphanus, Ricinus, Senecio, Sinomenium, Stephania, Sinapis, Solanum, Theobroma, Trifolium, Trigonella, Vicia, Vinca, Vilis,* and *Vigna*; the monocot genera *Allium, Andropogon, Aragrostis, Asparagus, Avena, Cynodon, Elaeis, Festuca, Festulolium, Heterocallis, Hordeum, Lemna, Lolium, Musa, Oryza, Panicum, Pannesetum, Phleum, Poa, Secale, Sorghum, Triticum*, and *Zea*; or the gymnosperm genera *Abies, Cunninghamia, Picea, Pinus*, and *Pseudotsuga*.

A transformed cell, callus, tissue, or plant can be identified and isolated by selecting or screening the engineered cells for particular traits or activities, e.g., those encoded by marker genes or antibiotic resistance genes. Such screening and selection methodologies are well known to those having ordinary skill in the art. In addition, physical and biochemical methods can be used to identify transformants. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are well known. Polynucleotides that are stably incorporated into plant cells can be introduced into other plants using, for example, standard breeding techniques.

DNA constructs may be introduced into the genome of a desired plant host by a variety of conventional techniques. For reviews of such techniques see, for example, Weissbach & Weissbach Methods for Plant Molecular Biology (1988, Academic Press, N.Y.) Section VIII, pp. 421-463; and Grierson & Corey, Plant Molecular Biology (1988, 2d Ed.), Blackie, London, Ch. 7-9. For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al (1987) Nature 327:70-73). Alternatively, the DNA constructs may be combined with suitable T-DNA flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al (1984) Science 233:496-498, and Fraley et al (1983) Proc. Nat'l. Acad. Sci. USA 80:4803. The virulence functions of the *Agrobacterium tumefaciens* host will direct the insertion of the construct and adjacent marker into the plant cell DNA when the cell is infected by the bacteria using binary T DNA vector (Bevan (1984) Nuc. Acid Res. 12:8711-8721) or the co-cultivation procedure (Horsch et al (1985) Science 227:1229-1231). Generally, the *Agrobacterium* transformation system is used to engineer dicotyledonous plants (Bevan et al (1982) Ann. Rev. Genet 16:357-384; Rogers et al (1986) Methods Enzymol. 118:627-641). The *Agrobacterium* transformation system may also be used to transform, as well as transfer, DNA to monocotyledonous plants and plant cells. See Hernalsteen et al (1984) EMBO J 3:3039-3041; Hooykass-Van Slogteren et al (1984) Nature 311:763-764; Grimsley et al (1987) Nature 325:1677-179; Boulton et al (1989) Plant Mol. Biol. 12:31-40; and Gould et al (1991) Plant Physiol. 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) EMBO J3:2717-2722, Potrykus et al. (1985) Molec. Gen. Genet. 199:169-177; Fromm et al. (1985) Proc. Nat.

Acad. Sci. USA 82:5824-5828; and Shimamoto (1989) Nature 338:274-276) and electroporation of plant tissues (D'Halluin et al. (1992) Plant Cell 4:1495-1505). Additional methods for plant cell transformation include microinjection, silicon carbide mediated DNA uptake (Kaeppler et al. (1990) Plant Cell Reporter 9:415-418), and microprojectile bombardment (see Klein et al. (1988) Proc. Nat. Acad. Sci. USA 85:4305-4309; and Gordon-Kamm et al. (1990) Plant Cell 2:603-618).

The disclosed methods and compositions can be used to insert exogenous sequences into a predetermined location in a plant cell genome. This is useful inasmuch as expression of an introduced transgene into a plant genome depends critically on its integration site. Accordingly, genes encoding, e.g., nutrients, antibiotics or therapeutic molecules can be inserted, by targeted recombination, into regions of a plant genome favorable to their expression.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in Handbook of Plant Cell Culture, pp. 124-176, Macmillian Publishing Company, New York, 1983; and Binding, Regeneration of Plants, Plant Protoplasts, pp. 21-73, CRC Press, Boca Raton, 1985. Regeneration can also be obtained from plant callus, explants, organs, pollens, embryos or parts thereof. Such regeneration techniques are described generally in Klee et al (1987) Ann. Rev. of Plant Phys. 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*).

Thus, the disclosed methods and compositions have use over a broad range of plants, including, but not limited to, species from the genera *Asparagus, Avena, Brassica, Citrus, Citrullus, Capsicum, Cucurbita, Daucus, Glycine, Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna*, and *Zea*. One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection may be performed by growing the engineered plant material on media containing an inhibitory amount of the antibiotic or herbicide to which the transforming gene construct confers resistance. Further, transformed plants and plant cells may also be identified by screening for the activities of any visible marker genes (e.g., the .beta.-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the amount of mRNA has increased, it can be assumed that the corresponding endogenous gene is being expressed at a greater rate than before. Other methods of measuring gene and/or CYP74B activity can be used. Different types of enzymatic assays can be used, depending on the substrate used and the method of detecting the increase or decrease of a reaction product or by-product. In addition, the levels of and/or CYP74B protein expressed can be measured immunochemically, i.e., ELISA, RIA, EIA and other antibody based assays well known to those of skill in the art, such as by electrophoretic detection assays (either with staining or western blotting). The transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

Delivery Vehicles

An important factor in the administration of polypeptide compounds, such as TAL-cleavage domain fusion protein, is ensuring that the polypeptide has the ability to traverse the plasma membrane of a cell, or the membrane of an intracellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as TAL-cleavage domain fusion proteins across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996)). Another subsequence, the h (hydrophobic) domain of signal peptides, was found to have similar cell membrane translocation characteristics (see, e.g., Lin et al., J. Biol. Chem. 270: 14255-14258 (1995)).

Examples of peptide sequences which can be linked to a protein, for facilitating uptake of the protein into cells, include, but are not limited to: an 11 amino acid peptide of the tat protein of HIV; a 20 residue peptide sequence which corresponds to amino acids 84-103 of the p16 protein (see Fahraeus et al., Current Biology 6:84 (1996)); the third helix of the 60-amino acid long homeodomain of Antennapedia (Derossi et al., J. Biol. Chem. 269:10444 (1994)); the h region of a signal peptide such as the Kaposi fibroblast growth factor (K-FGF) h region (Lin et al., supra); or the VP22 translocation domain from HSV (Elliot & O'Hare, Cell 88:223-233 (1997)). Other suitable chemical moieties that provide enhanced cellular uptake may also be chemically linked to ZFPs. Membrane translocation domains (i.e., internalization domains) can also be selected from libraries of randomized peptide sequences. See, for example, Yeh et al. (2003) Molecular Therapy 7(5):S461, Abstract #1191.

Toxin molecules also have the ability to transport polypeptides across cell membranes. Often, such molecules (called "binary toxins") are composed of at least two parts: a translocation/binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used to deliver peptides to the cell cytosol as internal or amino-terminal fusions (Arora et al., J. Biol. Chem., 268:3334-3341 (1993); Perelle et al., Infect. Immun., 61:5147-5156 (1993); Stennark et al., J. Cell Biol. 113:1025-1032 (1991); Donnelly et al., PNAS 90:3530-3534 (1993); Carbonetti et al., Abstr. Annu Meet. Am. Soc. Microbiol. 95:295 (1995); Sebo et al., Infect. Immun. 63:3851-3857 (1995); Klimpel et al., PNAS U.S.A. 89:10277-10281 (1992); and Novak et al., J. Biol. Chem. 267:17186-17193 1992)).

Such peptide sequences can be used to translocate TAL-cleavage domain fusion proteins across a cell membrane. TAL-cleavage domain fusion proteins can be conveniently fused to or derivatized with such sequences. Typically, the translocation sequence is provided as part of a fusion protein. Optionally, a linker can be used to link the TAL-cleavage domain fusion protein and the translocation sequence. Any suitable linker can be used, e.g., a peptide linker.

Targeted cleavage and targeted recombination can also be used to alter non-coding EBE sequences (e.g., regulatory sequences such as promoters, enhancers, initiators, terminators, splice sites) to alter the levels of expression of a gene product. Such methods can be used, for example, for therapeutic purposes, functional genomics and/or target validation studies.

The invention also provides methods for introducing the modified EBEs of the present invention into plants by crossing a plant which lacks the modified EBE with a plant that has the modified EBE, selfing the resulting generations and then selecting the plants exhibiting bacterial blight tolerance.

In another aspect, the invention provides a method for producing a hybrid seed comprising crossing a first plant parent with a second plant parent and harvesting the resultant hybrid seed, wherein either one or both parents contain modified EBEs. The hybrid seeds, plant and parts thereof produced by such method are also part of the invention.

In another aspect, the present invention provides for further single gene converted plants with modified EBEs. The desired further single transferred gene may preferably be a dominant or recessive allele. Preferably, the further single transferred gene will confer such traits as herbicide resistance, insect resistance, resistance for bacterial, fungal, or viral disease, male fertility, male sterility, enhanced nutritional quality, and industrial usage. The single gene may be a naturally occurring gene or a transgene introduced through genetic engineering techniques.

In another aspect, the present invention provides regenerable cells for use in tissue culture of a plant containing a modified EBE. The tissue culture will preferably be capable of regenerating plants having the physiological and morphological characteristics of the foregoing plant, and of regenerating plants having substantially the same genotype as the foregoing plant. Preferably, the regenerable cells in such tissue cultures will be embryos, protoplasts, meristematic cells, callus, pollen, leaves, anthers, pistils, roots, root tips, flowers, seeds, panicles or stems. Still further, the present invention provides plants regenerated from the tissue cultures of the invention.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Thus, many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

TABLE OF SEQUENCES

| | | |
|---|---|---|
| Wild type EBE sequence | nucleotide | SEQ ID NO: 1 |
| −55 mutant | nucleotide | SEQ ID NO: 2 |
| −32 mutant | nucleotide | SEQ ID NO: 3 |
| −18 mutant | nucleotide | SEQ ID NO: 4 |
| −9 mutant | nucleotide | SEQ ID NO: 5 |

-continued

TABLE OF SEQUENCES

| | | |
|---|---|---|
| −5 mutant | nuceotide | SEQ ID NO: 6 |
| −4 mutant | nucleotide | SEQ ID NO: 7 |
| −3 mutant | nucleotide | SEQ ID NO: 8 |
| +9 mutant | nucleotide | SEQ ID NO: 9 |
| −49 mutant | nucleotide | SEQ ID NO: 10 |
| −8 mutant | nucleotide | SEQ ID NO: 11 |
| −6 mutant | nucleotide | SEQ ID NO: 12 |
| −5 mutant A | nucleotide | SEQ ID NO: 13 |
| −4 mutant A | nucleotide | SEQ ID NO: 14 |
| +2 mutant | nucleotide | SEQ ID NO: 15 |
| AvrXa7 EBE | nucleotide | SEQ ID NO: 16 |
| PthXo3 EBE | nucleotide | SEQ ID NO: 17 |
| Os12N3 EBE | nucleotide | SEQ ID NO: 18 |
| Os8N3 EBE | nucleotide | SEQ ID NO: 19 |
| Overlapping AvrXa7 and PthXo3 EBE | nucleotide | SEQ ID NO: 20 |
| dTALEN R1 | nucleotide | SEQ ID NO: 21 |
| dTALEN R2 | nucleotide | SEQ ID NO: 22 |
| dTALEN L1 | nucleotide | SEQ ID NO: 23 |
| dTALEN R1 | amino acid | SEQ ID NO: 24 |
| dTALEN R2 | amino acid | SEQ ID NO: 25 |
| dTALENL1 | amino acid | SEQ ID NO: 26 |
| forward primer of ~550 bp with the target sites | nucleotide | SEQ ID NO: 27 |
| reverse primer of ~550 bp with the target sites | nucleotide | SEQ ID NO:28 |
| internal sequencing primer | nucleotide | SEQ ID NO: 29 |
| Os11N3 primer | nucleotide | SEQ ID NO: 30 |
| OS11N3 primer | nucleotide | SEQ ID NO: 31 |
| Os04g19960 primer | nucleotide | SEQ ID NO: 32 |
| Os04g19960 primer | nucleotide | SEQ ID NO: 33 |
| TFIIAγ5 primer | nucleotide | SEQ ID NO: 34 |
| TFIIAγ5 primer | nucleotide | SEQ ID NO: 35 |
| SWT11-TALEN-L | nucleotide | SEQ ID NO: 36 |
| SWT11-TALEN-L | amino acid | SEQ ID NO: 37 |
| SWT11-TALEN-R | nucleotide | SEQ ID NO: 38 |
| SWT11-TALEN-R | amino acid | SEQ ID NO: 39 |
| SWT11-F primer | nucleotide | SEQ ID NO: 40 |
| SWT11-R primer | nucleotide | SEQ ID NO: 41 |
| PthXo1 EBE | nucleotide | SEQ ID NO: 42 |
| Wild type OS8N3 promoter | nucleotide | SEQ ID NO: 43 |
| Os8N3 −6 | nucleotide | SEQ ID NO: 44 |
| Os8N3 −8 | nucleotide | SEQ ID NO: 45 |
| Os8N3 −21 | nucleotide | SEQ ID NO: 46 |
| Os8N3 −14 | nucleotide | SEQ ID NO: 47 |
| Os11N3 −4b | nucleotide | SEQ ID NO: 48 |
| SWT11-TALEN-L RVD | amino acid | SEQ ID NO: 49 |
| SWT11-TALEN-L RVD target | nucleotide | SEQ ID NO: 50 |
| SWT11-TALEN-R RVD | amino acid | SEQ ID NO: 51 |
| SWT11-TALEN-R RVD target | nucleotide | SEQ ID NO: 52 |

The following examples are offered by way of illustration and not by way of limitation.

EXAMPLE 1

Transcription activator-like effectors (TALEs) of *Xanthomonas oryzae* pv. *oryzae* (Xoo) contribute to pathogen virulence through transcriptionally activating the rice disease susceptibility (S) genes. TALE nucleases (TALENs), the hybrid proteins of native or customized TAL effectors and the DNA cleavage domain of FokI, have been used to create intact yeast and animals whose genomes contain site-specific modifications. TALEN-mediated genome editing has not been demonstrated in plants. Here we exploit the paradigm of TALE/S-gene interaction using TALENs to edit the S gene in a way that renders it no longer responsive to the cognate TAL effector and, thus, confers resistance to bacterial blight of rice, a devastating disease in a crop that feeds half of the world's population.

Figure 1:
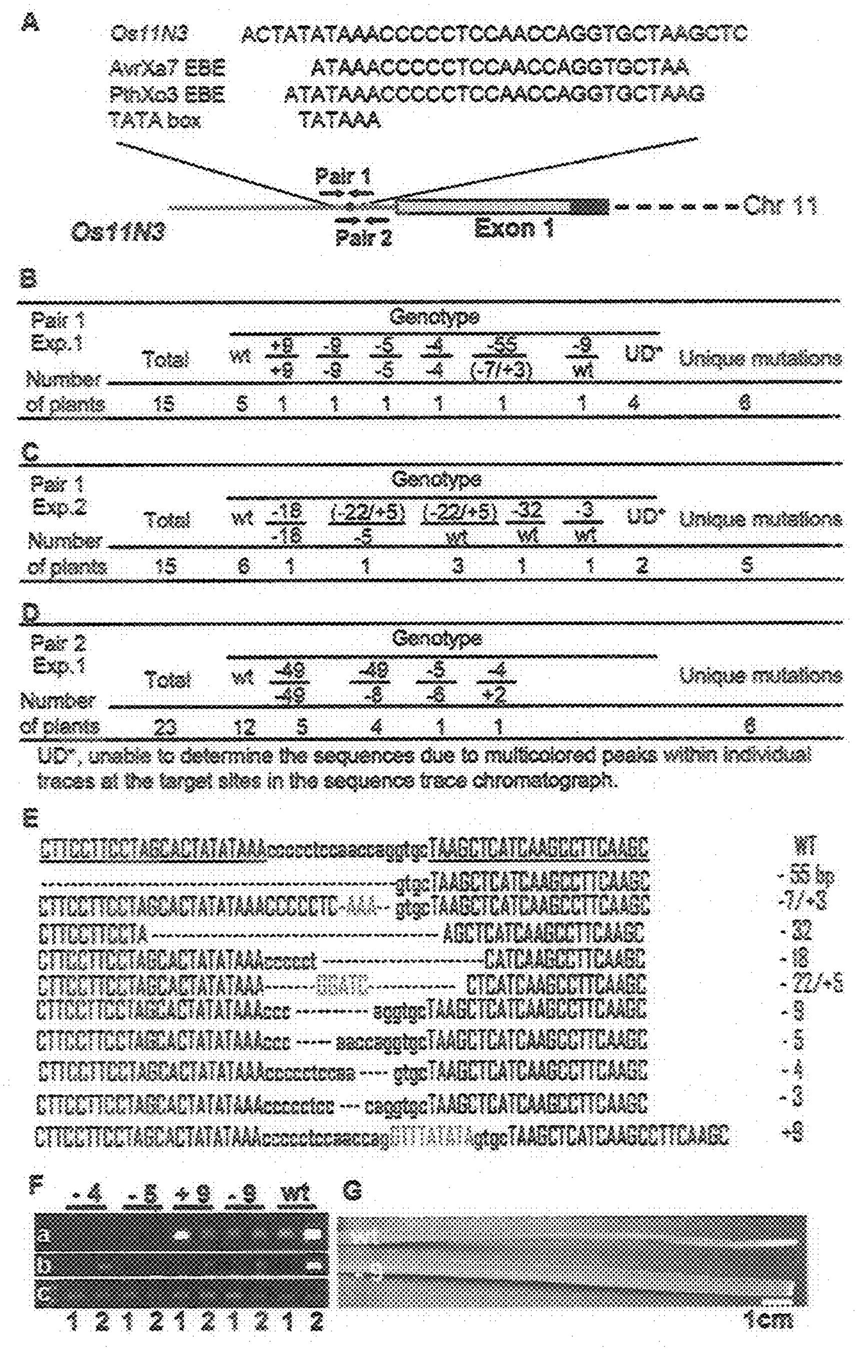
FIG. 1 demonstrates the high efficiency of targeted gene editing with TALENs. (A) Overlapping elements targeted by two pairs (Pair 1 and 2) of TALENs in the Os11N3 promoter. SEQ ID NO: 1 (Os11N3), SEQ ID NO: 16 (avrXa7 EBE) and SEQ ID NO: 17 (PthXo3 EBE) (B)-(D) Genotyping of T1 plants derived from the TALEN-expressed embryonic cells from independent transformation experiments (Exp.). Alleles containing wild type (wt), nucleotide insertion (+) and deletion (−) are separated by "/". (E) Sequences of Os11N3 mutations induced by the Pair 1 nucleases with deletions (dashes) and insertions (red letters) (SEQ ID NOS 1-9 respectively). TALEN-binding sequences are underlined. (F) Os11N3 induction by AvrXa7 in plants of different genotypes. RT-PCR products are Os11N3 (gel a), Os04g19960 (gel b) and TFIIAγ5 (gel c) under treatments of Xoo strain ME2 (lane 1) and ME2 (avrXa7) (lane 2). (G) Resistance phenotype from one of T1 mutant plants.
Figure 2:
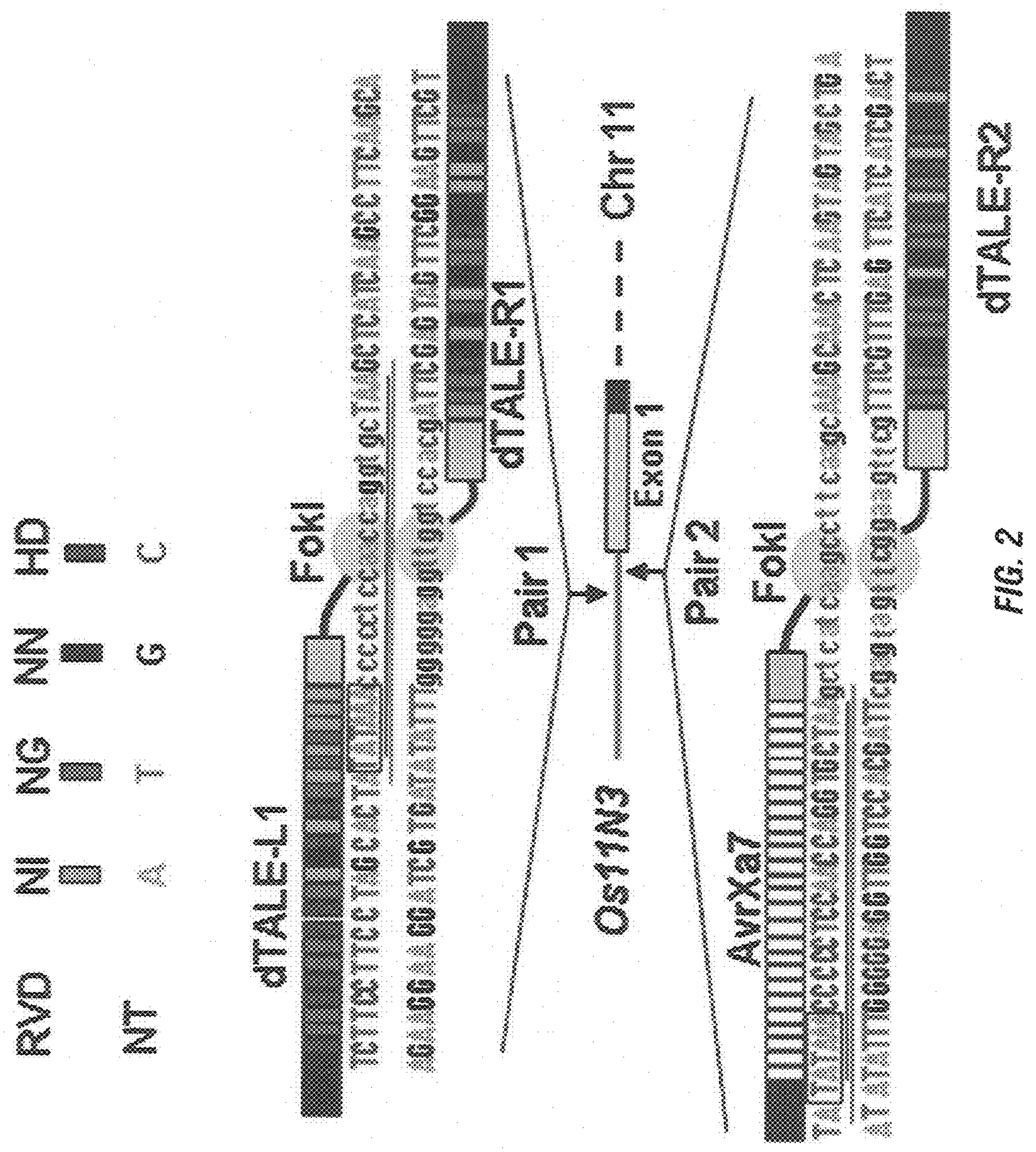
FIG. 2 shows TALENs and their target DNA sequences in the promoter of chromosomal Os11N3 gene. Four basic modular repeats whose repeat variable diresidue (RVD) (colored blocks) recognizing one nucleotide (NT) in the target site are used to assemble the DNA binding domain of each designer TALEN. The two pairs of nucleases (Pair 1 and 2) are fusions between the DNA cleavage domain of Fold (FokI) and the native (AvrXa7) or customized TAL effector (dTALE). The last 40 amino acids at C-terminus of AvrXa7 and dTALE-L1 are truncated to avoid the inappropriate induction of Os11N3 by the activation domain (SEQ ID NO:1 and reverse complement). The other two TAL effectors (dTALE-R1 and dTALE-R2) contain the complete C-terminus. All four TAL effectors contain the complete N-terminus. Os11N3 promoter contains an effector binding element (EBE) for AvrXa7 (underlined in black), an EBE for PthXo3 (underlined in red) and the TATA box (boxed). Lower letters represent regions wherein two FokI domains dimerize and cause a double stranded DNA break.

We sought to target Os11N3, a developmentally regulated S gene, whose induction by TAL effector AvrXa7 or PthXo3 is required for bacterial blight disease in rice. The Os11N3 promoter contains a region wherein the effector binding element (EBE) for AvrXa7, EBE for PthXo3 and the TATA box of the promoter overlap (FIG. 1A). Two pairs of TALENs (Pair 1 and Pair 2) were deployed to induce mutations in the overlapping EBEs of the Os11N3 promoter and thus to interfere with the interaction between Os11N3 and AvrXa7 as well as PthXo3 in rice (FIG. 1A). The TALEs used for nuclease fusions included the AvrXa7 recognition region and three designer TALEs whose central 24 repeat units for recognition of 24 nucleotides in each TALEN were custom-made using our modular assembly method (FIG. 2).

One of the paired nuclease genes was constructed under the 35S promoter of cauliflower mosaic virus and the other under the maize ubiquitin 1 promoter in a single plasmid (FIG. 3). Rice embryonic cells were transformed for nuclease gene expression through *Agrobacterium tumefaciens*; individual transformant cells were selected, propagated and regenerated to transgenic plants (T0). The progeny (T1) of T0 plants were analyzed for site-specific sequence alterations by sequencing the PCR-amplified genomic DNA in the Os11N3 promoter. For Pair 1 nucleases, about two-thirds (63%) of the randomly selected T1 plants (n=30) carried a mono- or bi-allelic mutation from two independent transformation experiments (FIGS. 1B and 1C); about half (48%) of twenty eight T1 plants contained mutations that were induced by Pair 2 TALENs (FIG. 1D). In total, at least 14 distinct mutations including 6 in homozygous lines were detected in 53 T1 plants, and the majority of the mutations were small region deletions, all of which left the TATA box intact, with the exception of two deletions that co-existed with a wild type allele (FIG. 1E and FIG. 4). All mutant plants were morphologically normal compared to the segregating wild type plants.

We next investigated Os11N3 inducibility and susceptibility to the Xoo strain, which is dependent on AvrXa7 for virulence, in plants that were homozygous for mutations in the EBEs for AvrXa7 and PthXo1. As expected, the inducibility of Os11N3 by AvrXa7 was abolished in plants homozygous for the 9, 5, or 4 bp deletion or the 9 bp insertion; the plants also showed concomitant gain of resistance (health vs. curling and dry leaves) to the Xoo strain (FIGS. 1F and 1G). The loss of induction is specific to Os11N3 as the induction of Os04g19960, a transposon coding gene "collaterally" targeted by AvrXa7, was not affected (FIG. 1F). Bacterial infection assays on other T1 plants (n=627) generated from Experiment 1 (Pair 1) and not previously genotyped showed ~49% plants with resistance to the Xoo strain.

Taken together, the results demonstrate that the TALENs are highly capable of mediating site-specific genetic modifications in rice. Based on our results, this TALEN-based technology could be applicable to other plant species and holds great promise in facilitating genome-enabled research and crop improvement.

Materials and Methods

TALEN Design and Construction.

Native AvrXa7 with transcription activation domain truncated was used for fusion to the wild type FokI DNA cleavage domain. Designer TALENs were made using our previously described "modular assembly" method that involved four basic repeats for TAL effector DNA binding domain and the wild type FokI DNA cleavage domain. All four TALENs used the complete N-terminus of TAL effectors; another designer TALEN, like AvrXa7-FokI, used a C-terminus truncated TAL effector. DNA sequences for the open reading frames of TALENs are provided in FIG. 4.

Construction of TALEN Expression Plasmids and Rice Transformation.

Two promoters used to express the paired TALEN genes were the maize ubiquitin 1 promoter (ubi1) and the 35S promoter of cauliflower mosaic virus (35S). Both promoters were modified at the cloning sites (more detail is available upon request). One of the paired TALEN genes was cloned downstream of the 35S promoter by BamHI and SpeI sites in pCAMBIA1300 backbone (Cambia, Australia) and the other under ubi1 promoter also at BamHI and SacI sites. The ubi1-TALEN gene expression cassette was cut out with HindIII and moved into pCAMBIA 1300 derived plasmid that already contained the 35S-TALEN gene expression cassette. The resultant plasmids were mobilized into *Agrobacterium tumefaciens* strain EHA105 by electroporation. *Agrobacterium*-mediated transformation of the rice cultivar Kitake was conducted according to the protocol as described.

Sequencing Analysis of Genomic Regions in Os11N3 Targeted by TALENs.

Individual T1 plants were randomly selected for genomic DNA extraction using the CTAB method as previously described. Forward primer, 5'-TCCCTTAACTAGGACAACTTGGA-3' (SEQ ID NO:27), and reverse primer, 5'-CCGGATCCAGCCATTGCAGCAAGATCTTG-3' (SEQ ID NO:28), were used to amplify a region of ~550 bp with the preselected target sites located in the middle. The PCR products from individual plants were sequenced using an internal primer, 5'-CATGGCTGTGATTGATCAGG-3' (SEQ ID NO:29). Each sequencing chromatogram was manually analyzed for polymorphisms within a trace.

Quantitative RT-PCR Analysis of Os11N3 Inducibility with AvrXa7.

Bacterial inoculums with optical density of 1.0 at 600 nm ($OD_{600}$) were infiltrated by using needleless syringe into rice leaves as described. The bacterial strains are Xoo strain PXO99ME2 (hereinafter as ME2), a PXO99 derivative strain with loss of TAL effector pthXo1 and concomitant loss of strain virulence, and ME2(avrXa7), an ME2 transformant of avrXa7 gene with regain of strain virulence and Os11N3 gene induction. Total RNA of the inoculated portion of leaves was extracted using TRI reagent from Ambion 24 hours after inoculation, and RNA concentration and quality were measured using an ND-1000 Nanodrop spectrophotometer (Nanodrop Technologies). One microgram of RNA from each strain inoculation was treated with amplification grade DNase 1 (Invitrogen) followed by cDNA synthesis using the iScript cDNA synthesis kit (Bio-Rad). cDNA derived from 25 ng of total RNA was used for detection of gene induction by AvrXa7 using semi-quantitative PCR. In addition to inducing Os11N3, AvrXa7 also “collaterally” induced another rice gene Os04g19960, which encodes a putative retrotransposon protein, but is not associated with disease susceptibility in rice (our unpublished data). Gene-specific primers for Os11N3 are 5'-GAGAAGAAGGTAGCTGCATGAGTG-3' (SEQ ID NO:30) and 5'-TCATGGAAGGAACCCTTACAGGTTG-3' (SEQ ID NO:31), while primers for Os04g19960 are 5'-AGAAGGCGTAGGCATTCACAT-3' (SEQ ID NO:32) and 5'-ACATTAACACAGCACACGTCAAC-3' (SEQ ID NO:33). The rice general transcription factor TFIIAγ5 expression was used as an internal control with primers 5'-CTACTCAGCCAATAAATTGATAACTGC-3' (SEQ ID NO:34) and 5'-CAATTTCTACTACTCATCGTTTAG-3' (SEQ ID NO:35).

Disease Resistance Assay.

The fully expanded leaves of rice plants were inoculated by leaf tip clipping with scissors whose blades were immersed in bacterial suspensions ($OD_{600}$=0.5) immediately prior to each clipping as described. Symptoms were scored by measuring lesion length 12-14 days after inoculation and categorized as resistance (R) if lesion lengths were shorter than 3 cm and susceptibility if longer than 5.

References

B. Yang, A. Sugio, F. F. White, *Proc. Natl. Acad. Sci. U.S.A.* 103, 10503 (2006).
G. Antony et al., *Plant Cell* 22, 3864 (2010).
T. Li et al., *Nucleic Acids Res.* 39, 359 (2010).
M. Christian et al., *Genetics* 186, 757 (2010).
J. C. Miller et al., *Nat. Biotechnol.* 29, 143 (2011).
T. Li et al., *Nucleic Acids Res.* 39, 6315(2011).
P. Huang et al., *Nat. Biotechnol.* 29, 699 (2011).
L. Tesson et al., *Nat. Biotechnol.* 29, 695 (2011).
A. J. Wood et al., *Science* 333, 307 (2011).
A. H. Christensen, P. H. Quail, *Transgenic Res.* 5, 213 (1996).
J. T. Odell, F. Nagy, N. H. Chua, *Nature* 313, 810 (1985).
Y. Hiei, S. Ohta, T. Komari, T. Kumashiro, *Plant J.* 6, 271 (1994).
K. Edwards, C. Johnstone, C. Thompson, *Nucleic Acids Res.* 19, 1349 (1991).
H. E. Kauffman, A. P. K. Reddy, S. P. Hsiek, S. D. and Marca, *Plant Dis. Rep.* 57, 537 (1973).

EXAMPLE 2

In the previous example, two pairs of TALENs were employed to modify the overlapping EBEs in the promoter of Os11N3 (also called OsWEET14) bound by two TAL effectors AvrXa7 and PthXo3. Rice plants homozygous for the transmittable OsSWEET14 EBE mutations were resistant to AvrXa7- and PthXo3-dependent Xoo strains, and some rice lines were free of transgenes for TALENs and transformation marker. Those rice lines, however, were susceptible to the PthXo1-dependent Xoo strain PXO99 as the inducibility of OsSWEET11 by PthXo1 retained intact. Thus, we sought to address the questions such as whether TALENs could be useful to edit the function of other genes in rice, whether multiple (at least the two known) SWEET genes vulnerable to blight disease could be all edited sequentially to achieve broad disease resistance but not disrupt their normal functions.

Results

Design and Engineering of TALENs

Figures 5A, 5B:
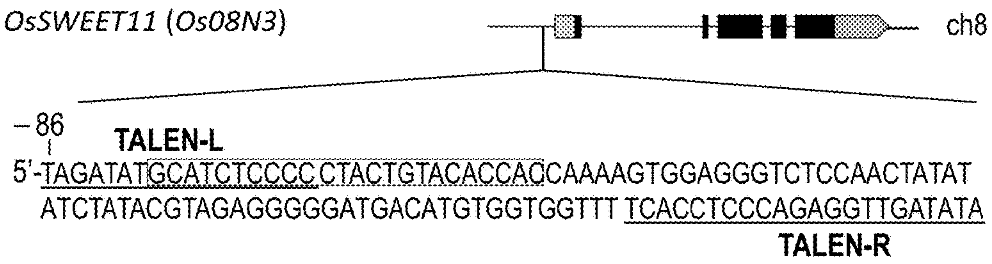

DNA sequence at the PthXo1 EBE of OsSWEET11 was used for screening of two adjacent sites for a pair of TALENs to bind. A sequence of 17 bp starting at 86 bp upstream of the transcription initiation site (NCBI accession number AK070510) was chosen for assembling one TALEN (SWT11-TALEN-L), while a nearby sequence of 22 bp from the complementary strand was based to synthesize another TALEN (SWT11-TALEN-R). The two sites were separated by 19 bp, and the left site partially overlapped with the PthXo1 EBE (FIG. 5A). Four basic 34-amino acid repeats recognizing four nucleotides as represented by the RVD of NI for A, NG for T, NN for G, and HD for C were used to assemble the DNA binding domains of the two TALENs (FIG. 5B) (for DNA sequences see SEQ ID NOS: 36, 38; for amino acid sequences see SEQ ID NOS:37, 39). A modular assembly method modified from our previously developed was used to synthesize the repeats (Li, Huang et al. 2011). To avoid the detrimental induction of OsSWEET11 probably caused by TALEN consisting of a full-length TAL effector, the SWT11-TALEN-L contained a version of TAL effector with the C-terminal 40-amino acid transcription activation domain truncated, while the SWT11-TALEN-R contained the full-length TAL effector as DNA binding domain. The TALENs used a complete TAL effector N-terminus (SEQ ID NOS:36-39). The paired TALENs were active against the target site as measured in our yeast single strand annealing assay (SAA) (data not shown).

Construction of TALEN Gene Expression Cassettes

The two promoters used to express the paired TALEN genes were the maize ubiquitin 1 promoter (ubi1) and the 35S promoter of cauliflower mosaic virus (Christensen, Quail 1996, Odell, Nagy et al. 1985). The SWT11-TALEN-L gene was cloned downstream of the 35S promoter at BamHI and SpeI sites in the binary vector p35S-H3; the SWT11-TALEN-R gene was cloned under the control of the ubi1 promoter similarly but in vector pEH3. The ubi1-TALEN-R gene expression cassette was excised with HindIII and moved into the HindIII site of the binary plasmid containing the 35S-TALEN-L. The resultant plasmid was then transformed into *Agrobacterium tumefaciens* strain EHA105 by electroporation. *Agrobacterium*-mediated transformation of rice cultivar Kitake that already contained OsSWEET14 promoter mutation (FIG. 6A) was performed according to a previously described protocol (Hiei, Ohta et al. 1994).

TALENs Induced OsSWEET11 Promoter Mutations

Figure 6B:
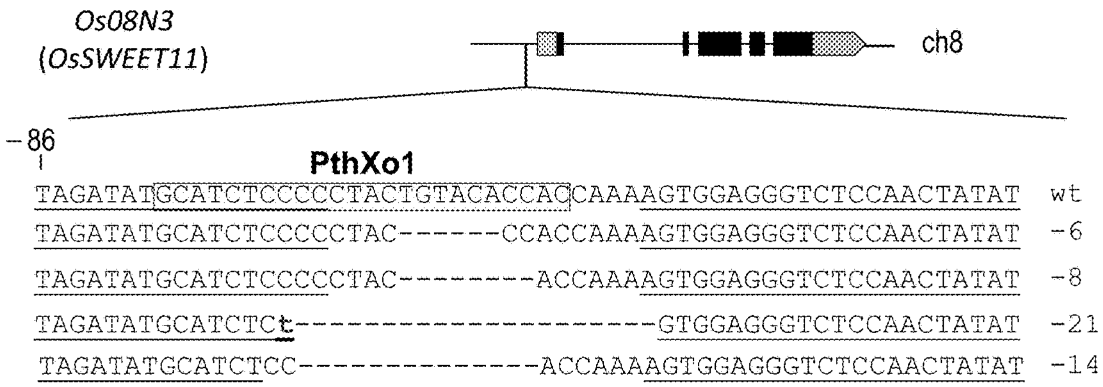

The previously modified rice grew and produced normally, and the seeds could be easily induced into prolific embryonic cells for transformation. Individual transformant cells were selected, propagated and regenerated into whole plants (T0). Twelve independent transformant rice lines were obtained and were self-pollinated to produce seeds. The OsSWEET11 promoter regions were amplified using the polymerase chain reaction (PCR) with a set of primers (SWT11-F and SWT11-R) and the genomic DNA extracted from the T0 plant leaves. The PCR products were sequenced with the primer (SWT11-F). The primer sequences are provided in Table 1. Five out of twelve genotyped lines contained mono-allelic mutations (data not shown). Similarly, the T1 progeny of 4 mutant lines were genotyped (n=22). New mutations (deletions, or substitutions) including those in homozygous forms were revealed in some progeny (FIG. 6B). The mutations deleted partial or whole PthXo1 EBEs in the promoter of OsSWEET11. Representative mutations are shown in FIG. 6B. All mutant plants show no obvious growth defect compared to the wild type plants (data not shown).

TABLE 1

| Primer | Sequence |
|---|---|
| SWT11-F (SEQ ID NO: 40) | caccggtaccTGAGTGGTCAT ACGTGTCATATTG |
| SWT11-R (SEQ ID NO: 41) | CCGGATCCATTGCTACTGGTG ATGAAGGT |

TALEN-Induced OsSWEET11 Mutations Result in Xoo Resistance

Figure 7B:
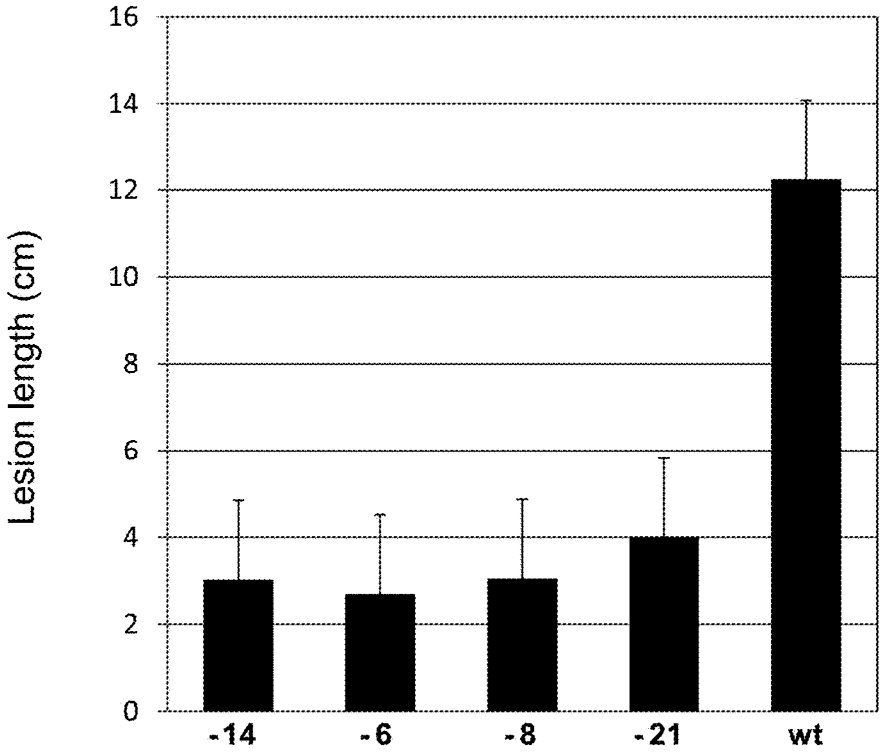

The progeny (T1) homozygous for mutations of 6 bp, 8 bp, and 21 bp deletions within the OsSWEET11 promoter were inoculated with PXO99, a Xoo strain depended on its PthXo1 to induce OsSWEET11 for virulence (Yang, Sugio et al. 2006), and the symptom of leaf blight and lesion lengths were measured 14 days post inoculation in a standard disease assay. The mutants were strongly resistant to bacterial infection compared to the wild type plants in term of symptom (FIG. 7A) and lengths of lesion (FIG. 7B).

The contents of any patents, patent applications, and references cited throughout this specification are hereby incorporated by reference in their entireties.

Those skilled in the art will recognize, or be able to ascertain using no more than routine experimentation, many equivalents to the specific embodiments of the invention described herein. Such equivalents are intended to be encompassed by the following claims.

What is claimed is:

1. A genetically modified plant or plant cell which includes a TAL effector binding element (EBE) of a bacterial pathogen disease susceptibility gene that has been modified with a TALEN fusion protein to prevent induction of expression of said gene by a TAL effectors of essential virulence chosen from the group consisting of AvrXa7 and PthXo3; wherein said TALEN fusion includes one or more of SEQ ID NO: 24, 25 26 and 39, wherein said modified plant or plant cell retains normal plant growth and development; and wherein said disease susceptibility gene has been modified in the EBE region while the TATAAA box remains intact.

2. The plant cell of claim 1, wherein said TAL EBE is selected from the group consisting of SEQ ID NO: 16, 17, and 20.

3. The plant cell of claim 2, wherein said disease susceptibility gene is one of the N3 family of genes in rice.

4. The plant cell of claim 2, wherein said disease susceptibility gene is Os11N3.

5. The plant cell of claim 1, wherein said disease susceptibility gene is Os11N3.

6. The plant cell of claim 5, wherein said Os11N3 gene includes a modification in the PthXo3 and AVrXa7 overlapping EBE region, SEQ ID NO:20.

7. The plant cell of claim 6, wherein said modification is a deletion modification.

8. The plant cell of claim 7, wherein said modification includes a deletion of 9 nucleotides of SEQ ID NO:1 bases 27-35.

9. The plant cell of claim 7, wherein said modification includes deletion of 5 nucleotides or bases 27-31 from wild type SEQ ID NO:1.

10. The plant cell of claim 7, wherein said modification includes deletion of 4 nucleotides or bases 34-38 from wild type SEQ ID NO:1.

11. The plant cell of claim 6, wherein said modification is an insertion.

12. The plant cell of claim 11, wherein said modification is an insertion of 9 bases (gtttatata) between bases 37 and 38 from wild type SEQ ID NO:1.

13. The plant cell of claim 2, wherein said EBE region includes a nucleotide sequence selected from the group consisting of SEQ ID NO: 5, 6, 7 and 9.

14. The plant cell of claim 2, wherein said plant cell includes a heterologous nucleic acid expression construct including a nucleic acid sequence encoding a TALEN fusion protein including one or more of SEQ ID NO: 24, 25, 26 or 39.

15. The plant cell of claim 2 wherein said plant cell includes a heterologous fusion protein of SEQ ID NO: 24, 25, 26 or 39.

16. The plant of claim 2 wherein said plant is resistant to bacterial blight.

17. A genetically modified seed of the plant of claim 2.

18. A method of producing a plant that is resistant to bacterial blight caused by *Xanthomonas oryzae* pv. *Oryzae* comprising: introducing to said plant a modification in an EBE region of a disease susceptibility gene of Osl1N3 so that a TAL effector chosen from the group consisting of AvrXa7 and PthXo3 is prevented from inducing expression of the same and said modification allows for normal plant growth and development; wherein said modification leaves the TATAAA box intact; wherein said introducing is by transforming said plant with a heterologous nucleic acid selected from the group consisting of SEQ ID NO: 21, 22, 23, and 38 that encodes a TALEN fusion protein that creates modifications in a target EBE sequence.

19. The method of claim 18 further including the steps of crossing said modified EBE region plant with a second plant to produce progeny plants, and selecting plants exhibiting bacterial blight tolerance.

20. The method of claim 19 further including the steps of crossing said selected plants with said second plant to produce backcross progeny plants, selecting a first backcross progeny plant that has bacterial blight resistance to produce selected backcross progeny plants, repeating said crossing and selecting steps three or more times in succession to produce a backcross progeny plant that comprises bacterial blight resistance and essentially all of the physiological and morphological characteristics of said original second plant when grown in the same environmental conditions.

21. The method of claim 20, wherein said TALEN fusion protein is SEQ ID NO: 24, 25, 26 or 39.

22. The method of claim 19, wherein said nucleic acid is (a) SEQ ID NO: 21, 22, 23 or 38;

(b) a nucleic acid sequence which encodes SEQ ID NO: 24, 25, 26 or 39

(c) a nucleic acid sequence which has 90% or greater sequence identity to (a) or (b); wherein said TALEN fission protein creates modifications in a target EBE sequence yet retains the ability of the gene to provide normal plant growth.

23. The method of claim 22, wherein said nucleic acid includes a promoter sequence operably linked thereto.

24. A method for producing bacterial blight resistance in plants comprising: introducing a mutation in the EBE region of SEQ ID NO: 16, 17 or 20 of an Osl1N3 gene by transforming said plants with a heterologous nucleic acid selected from the group consisting of SEQ ID NO: 21, 22, 23, and 38, wherein said mutation leaves the TATAAA box intact, and further wherein said mutation prevents AvrXa7 and PthXo3 induction yet still allows for normal plant growth and development.

25. The method of claim 24 wherein said mutation is a deletion mutation.

26. The method of claim 25 wherein said mutation is an insertion mutation.

27. The method of claim 24 wherein said mutation occurs in the region of SEQ ID NO:20, the overlapping AvrXa7 and PthXo3 EBE.

* * * * *